(12) United States Patent
LeBowitz et al.

(10) Patent No.: US 7,858,576 B2
(45) Date of Patent: *Dec. 28, 2010

(54) METHOD FOR TARGETING LYSOSOMAL ENZYMES

(75) Inventors: Jonathan H. LeBowitz, Whitefish Bay, WI (US); Stephen M. Beverley, Clayton, MO (US)

(73) Assignee: ZyStor Therapeutics, Inc., Milwaukee, WI (US)

( * ) Notice: Subject to any disclaimer, the term of this patent is extended or adjusted under 35 U.S.C. 154(b) by 348 days.

This patent is subject to a terminal disclaimer.

(21) Appl. No.: 11/807,729

(22) Filed: May 30, 2007

(65) Prior Publication Data

US 2009/0029467 A1   Jan. 29, 2009

Related U.S. Application Data

(63) Continuation of application No. 10/272,483, filed on Oct. 16, 2002, now Pat. No. 7,560,424, which is a continuation-in-part of application No. 10/136,841, filed on Apr. 30, 2002, now Pat. No. 7,396,811.

(60) Provisional application No. 60/287,531, filed on Apr. 30, 2001, provisional application No. 60/304,609, filed on Jul. 10, 2001, provisional application No. 60/329,461, filed on Oct. 15, 2001, provisional application No. 60/351,276, filed on Jan. 23, 2002, provisional application No. 60/384,452, filed on May 29, 2002, provisional application No. 60/386,019, filed on Jun. 5, 2002, provisional application No. 60/408,816, filed on Sep. 6, 2002.

(51) Int. Cl.
*A61K 38/00* (2006.01)
*A61K 38/16* (2006.01)
*C12N 15/09* (2006.01)
*C12N 9/00* (2006.01)
*C12N 9/96* (2006.01)

(52) U.S. Cl. ............... 514/1.1; 514/128; 514/7.6; 514/8.5; 424/185.1; 536/23.1; 435/69.1; 435/69.7; 435/70.1; 435/183

(58) Field of Classification Search .............. None
See application file for complete search history.

(56) References Cited

U.S. PATENT DOCUMENTS

| | | |
|---|---|---|
| 4,309,776 A | 1/1982 | Berguer ............... 3/1 |
| 4,522,811 A | 6/1985 | Eppstein et al. ......... 514/2 |
| 4,749,570 A | 6/1988 | Poznansky .......... 424/85 |
| 4,801,575 A | 1/1989 | Pardridge ........... 514/4 |
| 4,902,505 A | 2/1990 | Pardridge et al. ...... 424/85 |
| 5,236,838 A | 8/1993 | Rasmussen et al. ...... 435/209 |
| 5,258,453 A | 11/1993 | Kopecek et al. ....... 525/54.1 |
| 5,356,804 A | 10/1994 | Desnick et al. ........ 438/208 |
| 5,399,346 A | 3/1995 | Anderson et al. |
| 5,405,942 A | 4/1995 | Bell et al. ............ 536/23.1 |
| 5,470,828 A | 11/1995 | Ballard et al. ......... 514/12 |
| 5,476,779 A | 12/1995 | Chen et al. .......... 435/325 |
| 5,549,892 A | 8/1996 | Friedman et al. ....... 424/94.61 |
| 5,580,757 A | 12/1996 | Desnick et al. ........ 435/69.7 |
| 5,633,234 A | 5/1997 | August et al. ......... 514/44 |
| 5,633,235 A | 5/1997 | Townsend ............ 514/49 |
| 5,704,910 A | 1/1998 | Humes .............. 604/52 |
| 5,736,363 A | 4/1998 | Edwards et al. ........ 435/69.4 |
| 5,798,366 A | 8/1998 | Platt et al. ........... 514/315 |
| 5,817,623 A | 10/1998 | Ishii ............... 514/3 |
| 5,817,789 A | 10/1998 | Heartlein et al. ....... 536/23.4 |
| 5,827,703 A | 10/1998 | Debs et al. .......... 435/172.3 |
| 5,854,025 A | 12/1998 | Edwards et al. ........ 435/69.4 |
| 5,977,307 A | 11/1999 | Friden et al. ......... 530/350 |
| 5,981,194 A | 11/1999 | Jefferies et al. ....... 435/7.1 |
| 6,020,144 A | 2/2000 | Gueiros-Filho et al. ... 435/7.22 |
| 6,027,921 A | 2/2000 | Heartlein et al. ....... 435/69.7 |
| 6,066,626 A | 5/2000 | Yew et al. .......... 514/44 |
| 6,083,725 A | 7/2000 | Selden et al. ........ 435/69.8 |
| 6,118,045 A | 9/2000 | Reuser et al. ........ 800/14 |
| 6,226,603 B1 | 5/2001 | Freire et al. ......... 703/11 |
| 6,235,874 B1 | 5/2001 | Wu et al. ........... 530/303 |
| 6,262,026 B1 | 7/2001 | Heartlein et al. ...... 514/12 |
| 6,270,989 B1 | 8/2001 | Treco et al. ......... 435/69.1 |
| 6,273,598 B1 | 8/2001 | Keck et al. .......... 364/578 |

(Continued)

FOREIGN PATENT DOCUMENTS

EP   0196056 A2   10/1986

(Continued)

OTHER PUBLICATIONS

Barton et al., Proc Natl Acad Sci U S A. Mar. 1990;87(5):1913-1916.*

(Continued)

*Primary Examiner*—Gary B. Nickol
*Assistant Examiner*—Daniel C Gamett
(74) *Attorney, Agent, or Firm*—Choate, Hall & Stewart LLP; Fangli Chen

(57) ABSTRACT

Targeted therapeutics that localize to a specific subcellular compartment such as the lysosome are provided. The targeted therapeutics include a therapeutic agent and a targeting moiety that binds a receptor on an exterior surface of the cell, permitting proper subcellular localization of the targeted therapeutic upon internalization of the receptor. Nucleic acids, cells, and methods relating to the practice of the invention are also provided.

15 Claims, 15 Drawing Sheets

U.S. PATENT DOCUMENTS

| | | |
|---|---|---|
| 6,281,010 B1 | 8/2001 | Gao et al. .................... 435/325 |
| 6,284,875 B1 | 9/2001 | Turpen et al. ............... 530/427 |
| 6,329,501 B1 | 12/2001 | Smith et al. |
| 6,344,436 B1 | 2/2002 | Smith et al. ..................... 514/2 |
| 6,348,194 B1 | 2/2002 | Huse et al. .................. 424/143 |
| 6,441,147 B1 | 8/2002 | Turpen et al. ............... 530/427 |
| 6,451,600 B1 | 9/2002 | Rasmussen et al. ......... 435/358 |
| 6,455,494 B1 | 9/2002 | Jefferies et al. ................. 514/2 |
| 6,472,140 B1 | 10/2002 | Tanzi et al. |
| 6,537,785 B1 | 3/2003 | Canfield ................... 424/94.61 |
| 6,566,099 B1 | 5/2003 | Selden et al. .............. 435/69.8 |
| 6,569,661 B1 | 5/2003 | Qin et al. .................... 435/200 |
| 6,596,500 B1 | 7/2003 | Kang et al. .................. 435/7.2 |
| 7,396,811 B2 | 7/2008 | LeBowitz et al. |
| 2001/0006635 A1 | 7/2001 | Bennett et al. ............. 424/94.1 |
| 2001/0025026 A1 | 9/2001 | Heartlein et al. .............. 514/12 |
| 2002/0013953 A1 | 1/2002 | Reuser et al. ................. 800/14 |
| 2002/0081654 A1 | 6/2002 | Sandrin et al. ............. 435/69.1 |
| 2002/0110551 A1 | 8/2002 | Chen ....................... 424/94.61 |
| 2002/0142299 A1 | 10/2002 | Davidson et al. ................ 435/6 |
| 2003/0004236 A1 | 1/2003 | Meade ......................... 524/98 |
| 2003/0021787 A1 | 1/2003 | Hung et al. .............. 424/155.1 |
| 2003/0077806 A1 | 4/2003 | Selden et al. ............... 435/207 |
| 2003/0082176 A1 | 5/2003 | LeBowitz et al. |
| 2004/0005309 A1 | 1/2004 | LeBowitz et al. |
| 2004/0006008 A1 | 1/2004 | LeBowitz et al. |
| 2004/0029779 A1 | 2/2004 | Zhu et al. ........................ 514/3 |
| 2004/0081645 A1 | 4/2004 | Van Bree et al. ......... 424/94.61 |
| 2004/0248262 A1 | 12/2004 | Koeberl et al. |
| 2005/0026823 A1 | 2/2005 | Zankel et al. ................. 514/12 |
| 2005/0058634 A1 | 3/2005 | Zhu ........................ 424/94.61 |
| 2005/0281805 A1 | 12/2005 | LeBowitz et al. |

FOREIGN PATENT DOCUMENTS

| | | |
|---|---|---|
| EP | 0466222 A1 | 1/1992 |
| EP | 0599303 A2 | 6/1994 |
| WO | WO-9104014 A1 | 4/1991 |
| WO | WO-9114438 A1 | 10/1991 |
| WO | WO-9222332 A2 | 12/1992 |
| WO | WO 93/06216 | 4/1993 |
| WO | WO-9310819 A1 | 6/1993 |
| WO | WO-9402178 A1 | 2/1994 |
| WO | WO-9502421 A1 | 1/1995 |
| WO | WO 00/53730 | 9/2000 |
| WO | WO 01/19955 | 3/2001 |
| WO | WO-0153730 A1 | 7/2001 |
| WO | WO-0256907 A2 | 7/2002 |
| WO | WO-02087510 A2 | 11/2002 |
| WO | WO-03032727 A1 | 4/2003 |
| WO | WO-03032913 A2 | 4/2003 |
| WO | WO 03/057179 | 7/2003 |
| WO | WO-03102583 A1 | 12/2003 |
| WO | WO-2005078077 A2 | 8/2005 |
| WO | WO 02/44355 | 6/2006 |

OTHER PUBLICATIONS

Achord, et al., "Human β-Glucuronidase: In Vivo Clearance and in Vitro Uptake by a Glycoprotein Recognition System on Reticuloendothelial Cells," *Cell*, 15: 269-278 (Sep. 1978).

Achord et al., "Human β-Glucuronidase. II. Fate of Infused Human Placental β-Glucuronidase in the Rat," *Pediat. Res.*, 11: 816-822 (1977).

Allen et al., "Metabolic Correction of Fucosidosis Lymphoid Cells by Galaptin-α-L-Fucosidase Conjugates," *Biochemical and Biophysical Research Communications*, 172(1):335-340 (Oct. 15, 1990).

Authier et al., "In vitro endosome-lysosome transfer of dephosphorylated EGF receptor and Shc in rat liver," *FEBS Letters*, 00:25-31 (1999).

Bach et al., "Binding of Mutants of Human Insulin-like Growth Factor II to Insulin-like Growth Factor Binding Proteins 1-6," *The Journal of Biological Chemistry*, 268(12):9246-9254 (May 5, 1993).

Bartlett et al., "CAVEAT: A Program to Facilitate the Structure-derived Design of Biologically Active Molecules," in *Molecular Recognition: Chemical and Biological Problems*, 182-196 (1989).

Baxter, R.C., "Insulin-like growth factor (IGF)-binding proteins: interactions with IGFs and intrinsic bioactivities." *Am. J. Physiol. Endocrinol. Metab.*, 278:E967-E976 (2000).

Beutler et al., "Gaucher Disease," in *The Metabolic and Molecular Bases of Inherited Disease*, 8th ed., 3635-3668 (2001).

Bickel et al., "Delivery of peptides and proteins through the blood-brain barrier," *Advanced Drug Delivery Reviews*, 46(1-3):247-279 (2001).

Bijsterbosch et al., "Native and modified lipoproteins as drug delivery systems," *Advanced Drug Delivery Reviews*, 5:231-251 (1990).

Birkenmeier et al., "Increased Life span and Correction of Metabolic Defects in Murine Mucopolysaccharidosis Type VII After Syngeneic Bone Marrow Transplantation," *Blood*, 78(11):3081-3092 (1991).

Birkenmeier et al., "Murine Mucopolysaccharidosis Type VII, Characterization of a Mouse with β-Glucuronidase Deficiency," *J. Clin. Invest.*, 83(4):1258-1266 (Apr. 1989).

Blakey et al., "Effect of Chemical Deglycosylation of Ricin A Chain on the in Vivo Fate and Cytotoxic Activity of an Immunotoxin Composed of Ricin A Chain and Anti-Thy 1.1 Antibody," *Cancer Research*, 47: 947-952 (Feb. 1987).

Braulke, T., "Type-2 IGF Receptor: A Multi-Ligand Binding Protein," *Horm. Metab. Res.*, 31:242-248 (1999).

Brooks, "Immune Response to Enzyme Replacement Therapy in Lysosomal Storage Disorder Patients and Animal Models," *Molec. Genet. And Metab.*, 68: 268-275 (1999).

Brown et al., "Structure of a functional IGF2R fragment determined from the anomalous scattering of sulfur," *The EMBO Journal*, 21(5):1054-1062 (2002).

Bürgisser et al., "Mutants of Human Insulin-like Growth Factor II with Altered Affinities for the Type 1 and Type 2 Insulin-like Growth Factor Receptor," *The Journal of Biological Chemistry*, 266(2):1029-1033 (Jan. 15, 1991).

Cacciari et al., "Somatomedin C in Pediatric Pathophysiology," *Pediatrician*, 14: 146-153 (1987).

Calhoun et al., "Fabry disease: Isolation of a cDNA clone encoding human α-galactosidase A," *Proc. Natl. Acad. Sci. USA*, 82:7364-7368 (Nov. 1985)..

Cascieri et al., "Structural Analogs of Human Insulin-like Growth Factor (IGF) I with Altered Affinity for Type 2 IGF Receptors," *The Journal of Biological Chemistry*, 264(4):2199-2202 (Feb. 5, 1999).

Connolly-Martin, Y., "Computer-Assisted Rational Drug Design," *Methods in Enzymology*, 203: 587-613 (1991).

Daly et al., "Neonatal gene transfer leads to widespread correction of pathology in a murine model of lysosomal storage disease," *Proc. Natl. Acad. Sci. USA*, 96(5):2296-2300 (Mar. 1999).

Diment et al., "Generation of Macrophage Variants With 5-Azacytidine: Selection for Mannose Receptor Expression," *J. Leukocyte Biol.*, 42: 485-490 (1987).

Dixon, J.S., "Computer-aided drug design: getting the best results," *Tibtech*, 10: 357-363 (1992).

Dobrenis et al., "Neuronal Lysosomal Enzyme Replacement Using Fragment C of Tetanus Toxin," *Proc. Natl. Acad. Sci. USA*, 89:2297-2301 (Mar. 1992).

Douglass et al., "Chemical Deglycosylation Can Induce Methylation, Succinimide Formation, and Isomerization," *J. Protein Chem.*, 20(7): 571-576 (2001).

Eisen et al., "HOOK: A Program for Finding Novel Molecular Architectures That Satisfy the Chemical and Steric Requirements of a Macromolecule Binding Site," *Proteins: Structure, Function, and Genetics*, 19: 199-221 (1994).

Forbes et al., "Contribution of Residues A54 and L55 of the Human Insulin-like Growth Factor-II (IGF-II) A Domain to Type 2 IGF Receptor Binding Specificity," *Growth Factors*, 19:163-173 (2001).

Foxwell, et al., "The preparation of deglycosylated ricin by recombination of glycosidase-treated A-and B-chains: effects of deglycosylation on toxicity and in vivo distribution," *Biochemica et Biophysica Acta*, 923: 59-65 (1987).

Friden et al., "Anti-transferrin receptor antibody and antibody-drug conjugates cross the blood-brain barrier," *Proc. Natl. Acad. Sci. USA*, 88:4771-4775 (Jun. 1991).

Fukuta et al., "Insulin Fragments as a Carrier for Peptide Delivery Across the Blood-Brain Barrier," *Pharmaceutical Research*, 11(12):1681-1688 (1994).

Godar et al., "M6P/IGFII-receptor complexes urokinase receptor and plasminogen for activation of transforming growth factor-β1," *European Journal of Immunology*, 29:1004-1013 (1999).

Grimme et al., "Endocytosis of Insulin-like Growth Factor II by a Mini-receptor Based on Repeat 11 of the Mannose 6-Phosphate/Insulin-like Growth Factor II Receptor," *The Journal of Biological Chemistry*, 275(43):33697-33703 (Oct. 27, 2000).

Grubb et al., "Large scale purification of phosphorylated recombinant β-glucuronidase from over-expressing mouse L cells," *Fed. Am. Soc. Exp. Biol.*, 7: 1255a (1993).

Hashimoto et al., "N-terminal Deletion Mutants of Insulin-like Growth Factor-II (IGF-II) Show Thr$^7$ and Leu$^8$ Important for Binding to Insulin and IGF-I Receptors and Leu$^8$ Critical for All IGF-II Functions," *The Journal of Biological Chemistry*, 270(30):18013-18018 (Jul. 28, 1995).

Hickman et al., "A Recognition Marker Required for Uptake of a Lysosomal Enzyme by Cultured Fibroblasts," *BBRC*, 57: 55-61 (1974).

Houba et al., "Improved Characteristics of a Human β-Glucuronidase—Antibody Conjugate after Deglycosylation for Use in Antibody-Directed Enzyme Prodrug Therapy," *Bioconjugate Chem.*, 7: 606-611 (1996).

Ishibashi et al., "Asialoglycoprotein Receptor Deficiency in Mice Lacking the Minor Receptor Subunit," *J. Biol. Chem.*, 269(45): 27803-27806 (1994).

Islam et al., "C-terminal Processing of Human β-Glucuronidase," *J. Biol. Chem.*, 268(30): 22627-22633 (Oct. 1993).

Juuti-Uusitalo et al., "Selective targeting of avidin/mannose 6-phosphate receptor chimeras to early or late endosomes," *European Journal of Cell Biology*, 79:458-468 (Jul. 2000).

Kang et al., "Mannose 6-Phosphate/Insulin-like Growth Factor II Receptor Mediates the Growth-Inhibitory Effects of Retinoids," *Cell Growth & Differentiation*, 10:591-600 (Aug. 1999).

Kang et al., "Mannose-6-phosphate/insulin-like growth factor-II receptor is a receptor for retinoic acid," *Proc. Natl. Acad. Sci. USA*, 95:13671-13676 (Dec. 1998).

Kang et al., "Retinoic acid alters the intracellular trafficking of the mannose-6-phosphate/insulin-like growth factor II receptor and lysosomal enzymes," *Proc. Natl. Acad. Sci. USA*, 95:13687-13691 (Nov. 1998).

Körner et al., "Mannose 6-Phosphate/Insulin-like Growth Factor II Receptor Fails to Interact with G-proteins," *The Journal of Biological Chemistry*, 270(1):287-295 (Jan. 6, 1995).

Kundra et al., "Asparagine-linked Oligosaccharides Protect Lamp-1 and Lamp-2 from Intracellular Proteolysis," *J. Biol. Chem.*, 274(43): 31039-31046 (Oct. 1999).

Langford et al., "Leishmania: Codon Utilization of Nuclear Genes," *Experimental Parasitology*, 74:360-361 (1992).

Lau et al., "Loss of the imprinted IGF2/cation-independent mannose 6—phosphate receptor results in fetal overgrowth and perinatal lethality," *Genes & Development*, 8(24):2953-2963 (1994).

Lee et al., "Mannose Receptor—Mediated Regulation of Serum Glycoprotein Homeostasis," *Science*, 295: 1898-1901 (Mar. 2002).

Linnell et al., "Real Time Kinetics of Insulin-like Growth Factor II (IGF-II) Interaction with the IGF-II/Mannose 6-Phosphate Receptor," *The Journal of Biological Chemistry*, 276(26):23986-23991, (Jun. 29, 2001).

Ludwig et al., "Mouse Mutants Lacking the Type 2 IGF Receptor (IGF2R) Are Rescued from Perinatal Lethality in Igf2 and Igf1r Null Backgrounds," *Developmental Biology*, 177(2):517-535 (1996).

Ludwig et al., "Roles for mannose-6-phosphate receptors in lysosomal enzyme sorting, IGF-II binding and clathrin-coat assembly," *Trends in Cell Biology*, 5:202-206 (May 1995).

Lüthi et al., "Mutants of Human Insulin-like Growth Factor II (IGF II) Expression and Characterization of Truncated IGF II and of Two Naturally Occurring Variants," *Eur. J. Biochem.*, 205(2):483-490 (1992).

Magee et al., "Insulin-like Growth Factor I and Its Binding Proteins: A Study of the Binding Interface Using B-Domain Analogues," *Biochemistry*, 38(48):15863-15870 (1999).

Morgan et al., "Insulin-like growth factor II receptor as a multifunctional binding protein,." *Nature*, 329(6137):301-307 (Sep. 1987).

Niwa et al., "Efficient selection for high-expression transfectants with a novel eukaryotic vector," *Gene*, 108: 193-200 (1991).

Nykjær et al., "Mannose 6-Phosphate/Insulin-like Growth Factor-II Receptor Targets the Urokinase Receptor to Lysosomes via a Novel Binding Interaction," *The Journal of Cell Biology*, 141(3):815-828 (May 4, 1998).

O'Connor et al., "Enzyme replacement therapy for murine mucopolysaccharidosis type VII leads to improvements in behavior and auditory function," *J. Clin. Invest.*, 101: 1394-1400 (1998).

O'Dell et al., "Molecules in focus Insulin-like growth factor II (IGF-II)," *The International Journal of Biochemistry & Cell Biology*, 30(7):767-771 (1998).

Oksche et al., "Late Endosomal/Lysosomal Targeting and Lack of Recycling of the Ligand-Occupied Endothelin B Receptor," *Molecular Pharmacology*, 57:1104-1113 (2000).

Paasche et al., "Mechanisms of Endothelin Receptor Subtype-specific Targeting to Distinct Intracellular Trafficking Pathways," *The Journal of Biological Chemistry*, 276(36):34041-34050 (Sep. 7, 2001).

Pine, Stanley H., *Organic Chemistry*, 5$^{th}$ ed. (1987), McGraw Hill, p. 770.

Poznansky et al., "Enzyme Replacement Therapy in Fibroblasts from a Patient with Cholesteryl Ester Storage Disease," *FASEB J.*, 3:152-156 (Feb. 1989).

"Purification," *The QIAexpressionist*, pp. 63-107 (Mar. 2001).

"QIAexpress Protein Purification System," *QIAexpress—The Complete System for 6xHis Technology*, pp. 7-12.

Ramalingam et al., "Binding to the transferrin receptor is required for endocytosis of HFE and regulation of iron homeostasis," *Nature Cell Biology*, 2(12):953-957 (2000).

Rocca et al., "Involvement of the Ubiquitin/Proteasome System in Sorting of the Interleukin 2 Receptor β Chain to Late Endocytic Compartments," *Molecular Biology of the Cell*, 12:1293-1301 (May 2001).

Rohyt, J.F., *Essentials of carbohydrate chemistry*, (1998), Springer-Verlag: New York, p. 34-35.

Rohyt, J.F., *Essentials of carbohydrate chemistry*, (1998), Springer-Verlag: New York, p. 350.

Rosenberg, et al., "Immunosurveillance of Alglucerase Enzyme Therapy for Gaucher Patients: Induction of Humoral Tolerance in Seroconverted Patients After Repeat Administration," *Blood*, 93(6): 2081-2088 (Mar. 1999).

Roth et al., "Mutants of Human Insulin-like Growth Factor II: Expression and Characterization of Analogs With a Substitution of TYR$^{27}$ and/or a Deletion of Residues 62-67," *Biochem. Biophys. Res. Commun.*, 181(2):907-914 (1991).

Sakano et al., "The Design, Expression, and Characterization of Human Insulin-like Growth Factor II (IGF-II) Mutants Specific for Either the IGF-II/Cation-independent Mannose 6-Phosphate Receptor or IGF-I Receptor," *The Journal of Biological Chemistry*, 266(31):20626-20635 (Nov. 5, 1991).

Sands et al., "Biodistribution, Kinetics, and Efficacy of Highly Phosphorylated and Non-phosphorylated β-Glucuronidase in the Murine Model of Mucopolysaccharidosis VII," *J. Biol. Chem.*, 276(46): 43160-43165 (Nov. 2001).

Sands et al., "Enzyme Replacement Therapy for Murine Mucopolysaccharidosis Type VII," *J. Clin. Invest.*, 93(6):2324-2331 (Jun. 1994).

Sands et al., "Murine Mucopolysaccharidosis Type VII: Long Term Therapeutic Effects of Enzyme Replacement and Enzyme Replacement Followed by Bone Marrow Transplantation," *J. Clin. Invest.*, 99: 1596-1605 (1997).

Shipley et al., "The Role of Glycosylation and Phosphorylation in the Expression of Active Human β-Glucuronidase," *J. Biol. Chem.*, 268(16): 12193-12198 (1993).

Sly et al., "Active site mutant transgene confers tolerance to human β-glucuronidase without affecting the phenotype of MPS VII mice," *PNAS*, 98(5): 2205-2210 (Feb. 2001).

Smith et al., "Structure and Activity Dependence of Recombinant Human Insulin-like Growth Factor II on Disulfide Bond Pairing," *The Journal of Biological Chemistry*, 264(16):9314-9321 (Jun. 5, 1989).

Sojar et al., "Characterization of Rat Ovarian Lutropin Receptor," *J. Biol. Chem.*, 264(5): 2552-2559 (1989).

Sojar et al., "Chemical Deglycosylation of Glycoproteins," *Methods in Enzymology*, 138: 341-350 (1987).

Soper et al, "Enzyme replacement therapy improves reproductive performance in mucopolysaccharidosis type VII mice, but does not prevent postnatal losses," *Pediatr. Res.*, 45(2): 180-186 (1999).

Souriau et al., "Direct Selection of EGF Mutants Displayed on Filamentous Phage Using Cells Overexpressing EGF Receptor," *Biol. Chem.*, 380(4): pp. 451-458 (Apr. 1999).

Spiro et al., "Characterization of carbohydrate units of glycoproteins," *Methods Enzymol.*, 8: 44-49 (1966).

Stahl et al., "Evidence for specific recognition sites mediating clearance of lysosomal enzymes in vivo," *PNAS*, 73(11): 4045-4049 (Nov. 1976).

Terasawa et al., "Solution structure of human insulin-like growth factor II; recognition sites for receptors and binding proteins," *The EMBO Journal*, 13(23):5590-5597 (1994).

Thorpe et al., "Modification of the carbohydrate in ricin with metaperiodate—cyanoborohydride mixtures," *Eur. J. Biochem.*, 147: 197-206 (1985).

Thotakura et al., "Enzymatic Deglycosylation of Glycoproteins," *Methods in Enzymology*, 138: 350-359 (1987).

Timmermans et al., "Angiotensin II Receptors and Angiotensin II Receptor Antagonists," *Pharmacological Reviews*, 45(2):205-251 (1993).

Tong et al., "The Cation-independent Mannose 6-Phosphate Receptor Binds Insulin-like Growth Factor II," *The Journal of Biological Chemistry*, 263(6):2585-2588 (1988).

Torres et al., "Solution Structure of Human Insulin-like Growth Factor II. Relationship to Receptor and Binding Protein Interactions," *J. Mol. Biol.*, 248(2):385-401 (1995).

Tschinke et al., "The NEWLEAD Program: A New Method for the Design of Candidate Structures from Pharmacophoric Hypotheses," *J. Med. Chem.*, 36: 3863-3870 (1993).

Tsuji et al., "Lysosomal Enzyme Replacement using $\alpha_2$—Macroglobulin as a Transport Vehicle," *J. Biochem.*, 115:937-944 (1994).

Ulmasov et al., "Purification and kinetic analysis of recombinant CA XII, a membrane carbonic anhydrase overexpressed in certain cancers," *PNAS*, 97(26): 14212-14217 (Dec. 2000).

Vogler et al., "A Murine Model of Mucopolysaccharidosis VII," *Am. J. Pathol.*, 136(1): 207-217 (Jan. 1990).

Vogler et al., "Enzyme Replacement with Recombinant B-glucuronidase in the Newborn Mucopolysaccharidosis Type VII Mouse," *Pediatric Research*, 34(6): 837-840 (1993).

Vyas et al., "Ligand-Receptor-Mediated Drug Delivery: An Emerging Paradigm in Cellular Drug Targeting," *Critical Reviews™ in Therapeutic Drug Carrier Systems*, 18(1):1-76 (2001).

Wadensten et al., "Purification and Characterization of Recombinant Human Insulin-like Growth Factor II (IGF-II) Expressed as a Secreted Fusion Protein in *Escherichia coli*," *Biotechnology and Applied Biochemistry*, 13(3):412-421 (1991).

Waheed et al., "Regulation of transferrin-mediated iron uptake by HFE, the protein defective in hereditary hemochromatosis," *PNAS*, 99(5): 3117-3122 (Mar. 2002).

Wang et al., "Regulation of embryonic growth and lysosomal targeting by the imprinted *Igf2/Mpr* gene," *Nature*, 372(6505):464-467 (Dec. 1994).

Wang et al., "The insulin A and B chains contain sufficient structural information to form the native molecule," *Trends in Biochemical Sciences*, 16: 279-281 (Aug. 1991).

Waszkowycz et al., "PRO_LIGAND: An Approach to de Novo Molecular Design. 2. Design of Novel Molecules from Molecular Field Analysis (MFA) Models and Pharmacophores," *J. Med. Chem.*, 37: 3994-4002 (1994).

Willingham et al., "The Receptosome: an Intermediate Organelle of Receptor-Mediated Endocytosis in Cultured Fibroblasts," *Cell*, 21(1):67-77 (Aug. 1980).

Wolfe et al., "Murine Mucopolysaccharidosis Type VII: A Model System for Somatic Gene Therapy of the Central Nervous System," in *Protocols for Gene Transfer in Neuroscience: Towards Gene Therapy of Neurological Disorders*, Lowenstein et al., eds., John Wiley & Sons Ltd., Chap. 20, pp. 263-274 (1996).

Yamashiro et al., "Acidification of Endocytic Compartments and the Intracellular Pathways of Ligands and Receptors," *Journal of Cellular Biochemistry*, 26:231-246 (1984).

Yang et al., "Probing the Folding Pathways of Long $R^3$ Insulin-like Growth Factor-1 ($LR^3IGF$-1) and IGF-1 via Capture and Identification of Disulfide Intermediates by Cyanylation Methodology and Mass Spectrometry," *The Journal of Biological Chemistry*, 274(53):37598-37604 (Dec. 31, 1999).

York et al., "The Rate of Internalization of the Mannose 6-Phosphate/ Insulin-like Growth Factor II Receptor Is Enhanced by Multivalent Ligand Binding," *The Journal of Biological Chemistry*, 274(2):1164-1171 (1999).

Yu et al., "Insulin-Like Growth Factors (IGF-I, Free IGF-I, and IGF-II) and Insulin-Like Growth Factor Binding Proteins (IGFPB-2, IGFBP-3, IGFBP-6, and ALS) in Blood Circulation," *J. Clin. Lab. Anal.*, 13(4):166-172 (1999).

Zarn et al., "A mutant of human insulin-like growth factor II (IGF II) with the processing sites of proinsulin," *Eur. J. Biochem.*, 210:665-669 (1992).

Aerts et al., "Efficient Routing of Glucocerebrosidase to Lysosomes Requires Complex Oligosaccharide Chain Formation," *Biochem. Biophys. Res. Commun.*, 141(2): 452-458 (1986).

Amalfitano et al., "Recombinant Human Acid Alpha-Glucosidase Enzyme Therapy for Infantile Glycogen Storage Disease Type II: Results of a Phase I/II Clinical Trial," *Genet. Med.*, 3(2): 132-138 (2001).

Bijvoet et al, "Expression of cDNA-Encoded Human Acid Alpha-Glucosidase in Milk of Transgenic Mice," *Biochim. Biophys. Acta*, 1308(2): 93-96 (1996).

Bijvoet et al., "Human Acid Alpha-Glucosidase from Rabbit Milk Has Therapeutic Effect in Mice with Glycogen Storage Disease Type II," *Hum. Mol. Genet.*, 8(12): 2145-2153 (1999).

Bijvoet et al., "Recombinant Human Acid Alpha-Glucosidase: High Level Production in Mouse Milk, Biochemical Characteristics, Correction of Enzyme Deficiency in GSDII KO Mice," *Hum. Mol. Genet.*, 7(11): 1815-1824 (1998).

Hirschhorn et al., "Glycogen Storage Disease Type II: Acid α-Glucosidase (Acid Maltase) Deficiency," in *The Metabolic and Molecular Basis of Inherited Disease*, 8th ed., 3389-3420 (2001).

Hoefsloot et al., "Expression and Routeing of Human Lysosomal Alpha-Glucosidase in Transiently Transfected Mammalian Cells," *Biochem. J.*, 272(2): 485-492 (1990).

Kikuchi et al., "Clinical and Metabolic Correction of Pompe Disease by Enzyme Therapy in Acid Maltase-Deficient Quail," *J. Clin. Invest.*, 101(4): 827-833 (1998).

Martiniuk et al., "Correction of Glycogen Storage Disease Type II by Enzyme Replacement with a Recombinant Human Acid Maltase Produced by Over-Expression in a CHO-DHFR(neg) Cell Line," *Biochem. Biophys. Res. Commun.*, 276(3): 917-923 (2000).

Reuser et al., "Biochemical, Immunological, and Cell Genetic Studies in Glycogenosis Type II," *Am. J. Hum. Genet.* 30(2): 132-143 (1978).

Shin et al., "Functional Properties of Antibody Insulin-like Growth Factor Fusion Proteins," *J. Biol. Chem.*, 269(7): 4979-4985 (1994).

Stanley et al., "Chinese Hamster Ovary Cells Selected for Resistance to the Cytotoxicity of Phytohemagglutinin are Deficient in a UDP-N-Acetylglucosamine—Glycoprotein N-Acetylglucosaminyltransferase Activity," *Proc. Natl. Acad. Sci. USA*, 72(9): 3323-3327 (1975).

Stanley et al., "Selection and Characterization of Eight Phenotypically Distinct Lines of Lectin-Resistant Chinese Hamster Ovary Cell," *Cell*, 6(2): 121-128 (1975).

Tsuji et al., "Intracellular Transport of Acid Involvement of Acid Alpha-Glucosidase in Human Fibroblasts: Evidence for Involvement of Phosphomannosyl Receptor-Independent System," *J. Biochem.*, 104(2): 276-278 (1988).

Tsuji et al., "The Precursor of Acid Alpha-Glucosidase is Synthesized as a Membrane-Bound Enzyme," *Biochem. Int.*, 15(5): 945-952 (1987).

Van den Hout et al., "Enzyme Therapy for Pompe Disease with Recombinant Human Alpha-Glucosidase from Rabbit Milk," *J. Inherit. Metab. Dis.*, 24(2): 266-274 (2001).

Van den Hout et al., "Recombinant Human Alpha-Glucosidase from Rabbit Milk in Pompe Patients," *Lancet*, 356(9227): 397-398 (2000).

Van Hove et al., "High-Level Production of Recombinant Human Lysosomal Acid alpha-Glucosidase in Chinese Hamster Ovary Cells which Targets to Heart Muscle and Corrects Glycogen Accumulation in Fibroblasts from Patients with Pompe Disease," *Proc. Natl. Acad. Sci. USA*, 93(1): 65-70 (1996).

Waheed et al., "Human Lysosomal Acid Phosphatase is Transported as a Transmembrane Protein to Lysosomes in Transfected Baby Hamster Kidney Cells," *EMBO J.*, 7(8): 2351-2358 (1988).

Wisselaar et al., "Structural and Functional Changes of Lysosomal Acid Alpha-Glucosidase during Intracellular Transport and Maturation," *J. Biol. Chem.*, 268(3): 2223-2231 (1993).

Arai et al., "Conformations of Variably Linked Chimeric Proteins Evaluated by Synchrotron X-ray Small-Angle Scattering," *PROTEINS: Structure, Function, and Bioinformatics*, 57:829-838 (2004).

Armstrong et al., "Uptake of Circulating Insulin-Like Growth Factor-I Into the Cerebrospinal Fluid of Normal and Diabetic Rats and Normalization of IGF-II mRNA Content in Diabetic Rat Brain," *Journal of Neuroscience Research*, 59:649-660 (2000).

Beljaars et al., "Characteristics of the hepatic stellate cell-selective carrier mannose 6-phosphate modified albumin (M6P28-HSA)," *LIVER*, 21:320-328 (2001).

Brooks et al., "Functional correction of established central nervous system deficits in an animal model of lysosomal storage disease with feline immunodeficiency virus-based vectors," *PNAS Early Edition*, 1-6 (2002).

Chodobski et al., "Choroid Plexus: Target for Polypeptides and Site of Their Synthesis," *Microscopy Research and Technique*, 52:65-82 (2001).

Dahms et al., "Mannose 6-Phosphate Receptors and Lysosomal Enzyme Targeting," *The Journal of Biological Chemistry*, 264(21):12115-12118 (1989).

Dahms et al., "Mannose 6-Phosphate Receptors and Lysosomal Enzyme Targeting," *The Journal of Biological Chemistry*, 264(21):12115-12118 (1989).

Devedjian et al., "Transgenic mice overexpressing insulin-like growth factor-II in β cells develop type 2 diabetes," *The Journal of Clinical Investigation*, 105(6):731-740 (2000).

Devi et al., "An Insulin-Like Growth Factor II (IGF-II) Affinity-Enhancing Domain Localized within Extracytoplasmic Repeat 13 of the IGF-II/Mannose 6-Phosphate Receptor," *Molecular Endocrinology*, 12(11):1661-1672 (1998).

DiFalco et al., "Preparation of a recombinant chimaera of insulin-like growth factor II and interleukin 3 with high proliferative potency for haemopoietic cells," *Biochem. J.*, 326:407-413 (1997).

DiFalco et al., "Efficacy of an Insulin-Like Growth Factor-Interleukin-3 Fusion Protein in Reversing the Hematopoietic Toxicity Associated with Azidothymidine in Mice," *The Journal of Pharmacology and Experimental Therapeutics*, 284:449-454 (1998).

Duguay et al., "Post-translational Processing of the Insulin-like Growth Factor-2 Precursor," *J. Biol. Chem.*, 273(29):18443-18451 (1998).

Dziegielewska et al., "The ins and outs of brain-barrier mechanisms," *TRENDS in Neurosciences*, 25(2):69-71 (2002).

Golden et al., "Human Blood-Brain Barrier Leptin Receptor," *J. Clin. Invest.*, 99(1):14-18 (1997).

Gozes et al., "Neuropeptides: brain messengers of many faces," *TRENDS in Neurosciences*, 24(12):687-690 (2001).

Kiess et al., "Insulin-like Growth Factor II (IGF-II) and the IGF-II/Mannose-6-Phosphate Receptor: The Myth Continues," *Horm. Res.*, vol. 41 (suppl. 2):66-73 (1994).

Kim et al., "High-level expression and simple purification of recombinant human insulin-like growth factor I," *Journal of Biotechnology*, vol. 48:97-105 (1996).

LeBowitz et al., "Glycosylation-independent targeting enhances enzyme delivery to lysosomes and decreases storage in mucopolysaccharidosis type VII mice," *PNAS USA*, 101:3083-3088 (2004).

Liu et al., "Intranasal administration of insulin-like growth factor-I bypasses the blood-brain barrier and protects against focal cerebral ischemic damage," *Journal of the Neurological Sciences*, 187: 91-97 (2001).

Mazzolla et al., "Enhanced Resistance to *Cryptococcus neoformans* Infection Induced by Chloroquine in a Murine Model of Meningoencephalitis," *Antimicrobial Agents and Chemotherapy*, 41:802-807 (1997).

Nissley et al., "Reciprocal Modulation of Binding of Lysosomal Enzymes and Insulin-like Growth Factor-II (IGF-II) to the Mannose 6-Phosphate/IGF-II Receptor," *Adv. Exp. Med. Biol.*, vol. 293:311-324 (1991).

Pardridge, "Targeting Neurotherapeutic Agents Through the Blood-Brain Barrier," *Arch Neurol.*, 59: 35-40 (2002).

Pardridge, "Drug Delivery to the Brain," *Journal of Cerebral Blood Flow and Metabolism*, 17:713-731 (1997).

Prince et al., "Lipoprotein Receptor Binding, Cellular Uptake, and Lysosomal Delivery of Fusions between the Receptor-associated Protein (RAP) and α-L-Iduronidase or Acid α-Glucosidase," *J. Biol. Chem.*, 279(33):35037-35046 (2004).

Pulford et al., "Uptake of Circulating Insulin-Like Growth Factors (IGFs) into Cerebrospinal Fluid Appears to Be Independent of the IGF Receptors as Well as IGF-Binding Proteins," *Endocrinology*, 142(1):213-220 (2001).

Reinhardt et al., "Insulin-Like Growth Factors Cross the Blood-Brain Barrier," *Endocrinology*, 135: 1753-1761 (1994).

Sandoval et al., "Enhanced proliferative effects of a baculovirus-produced fusion protein of insulin-like growth factor and $\alpha_1$-proteinase inhibitor and improved anti-elastase activity of the inhibitor with glutamate at position 351," *Protein Engineering*, 15(5):413-418 (2002).

Sandoval et al., "The fusion of IGF I with stromal cell-derived factor I or α1 proteinase inhibitor alters their mitogenic or chemotactic activities while keeping their ability to inhibit HIV-1-gp120 binding," *Biochemical Pharmacology*, 65:2055-2063 (2003).

Sohar et al., "Mouse mutants lacking the cation-independent mannose 6-phosphate/insulin-like growth factor II receptor are impaired in lysosomal enzyme transport: comparison of cation-independent and cation-dependent mannose 6-phosphate receptor-deficient mice," *Biochem. J.*, vol. 330:903-908 (1998).

Sly et al., "Active site mutant transgene confers tolerance to human β-glucuronidase without affecting the phenotype of MPS VII mice," *PNAS*, 98(5):2205-2210 (2001).

Urayama et al., "Developmentally regulated mannose 6-phosphate receptor-mediated transport of a lysosomal enzyme across the blood-brain barrier," *PNAS*, 101(34):12658-12663 (2004).

Valenzano et al., "Soluble Insulin-like Growth Factor II/Mannose 6-Phosphate Receptor Carries Multiple High Molecular Weight Forms of Insulin-like Growth Factor II in Fetal Bovine Serum," *J. Biol. Chem.*, 270(27):16441-16448 (1995).

Valenzano et al., "Biophysical and Biological Properties of Naturally Occurring High Molecular Weight Insulin-like Growth Factor II Variants," *J. Biol. Chem.*, 272(8):4804-4813 (1997).

Van Doorn et al., "Antibodies Directed against the E Region of Pro-Insulin-like Growth Factor-II Used to Evaluate Non-Islet Cell Tumor-induced Hypoglycemia," *Clinical Chemistry*, 48(10):1739-1750 (2002).

Wang et al., "A study of protein-protein interactions in living cells using luminescence resonance energy transfer (LRET) from *Renilla* luciferase to *Aequorea* GFP," *Mol. Gen. Genet.*, 264:578-587 (2001).

Wilczak et al., "Insulin-like growth factor system in serum and cerebrospinal fluid in patients with multiple sclerosis," *Neuroscience letters*, 257:168-170 (1998).

Williams et al, "Enzyme Replacement in Pompe Disease With an α-Glucosidase-Low Density Lipoprotein Complex," *Birth Defects: Original Article Series*, vol. XVI, No. 1:415-423 (1980).

Zhu et al., "Conjugation of Mannose 6-Phosphate-containing Oligosaccharides to Acid α-Glucosidase Improves the Clearance of Glycogen in Pompe Mice," The Journal of Biological Chemistry, 279(48):50336-50341 (2004).

Zhu et al., "Carbohydrate-remodeled acid α-glucosidase with higher affinity for the cation-independent mannose 6-phosphate receptor demonstrates improved delivery to muscles of Pompe mice," Biochemical Journal, 36 pages (2005).

PCT International Search Report for International Application No. PCT/US02/13835 (2002).

PCT International Search Report for International Application No. PCT/US02/32968 (2002).

PCT International Search Report for International Application No. PCT/US02/32996 (2002).

PCT International Search Report for International Application No. PCT/US03/17211 (2003).

Kerr et al., "Comparison of recombinant and synthetically formed monoclonal antibody beta lactamase conjugates for anticancer prodrug activation", Bioconjugate Chemistry, 10, 1084-1089 (1999).

Russell et al. "Recombinant proteins for genetic disease", Clinical Genetics, 389-394 (1999).

Aeed and Elhammer, "Glycosylation of recombinant prorenin in insect cells: the insect cell line Sf9 does not express the mannose 6-phosphate recognition signal. Glycosylation of recombinant prorenin in insect cells: the insect cell line Sf9 does not express the mannose", Biochemistry, 33(29):8793-0797 (1994).

Anand, "The Cure", HarperCollins, New York, NY, Chapter 23, pp. 257-268 (2006).

Auletta et at, "Receptor-mediated endocytosis and degradation of insulin-like growth factor I and II in neonatal rat astrocytes", Journal of Neuroscience Research, 31:14-20 (1992).

Authier et al., "In vitro endosome-lysosome transfer of dephosphorylated EGF receptor and Shc in rat liver," FEBS Letters, 00:25-31 (1999).

Becker et al., "HLA and Mate Choice," J. Hum. Genet., 62:991 (1998).

Bishop et al., "Human $_a$-Galactosidase Characterization and Eukaryotic Expression of the Full-length cDNA and Structural Organization of the Gene," in Lipid Storage Disorders Biological and Medical Aspects, vol. 150:809-822 (1987).

Brady et al., "Enzyme replacement therapy in Fabry disease," J. Inherit, Metab. Dis., 24:18-24 (2001).

Bungard, Design of Prodrugs, pp. 7-9, 21-24, Elsevier, Amsterdam (1985).

Desnick et al., "Enzyme Replacement and Enhancement Therapies: Lessons from Lysosomal Disorders", Nature Reviews Genetics, 3:954-966 (Dec. 2002).

European Search Report for EP02801739 (2005).

European Search Report for EP08000935 (2008).

European Supplementary Partial Search Report for European Application No. EP 03 73 6779 (Date of mailing Apr. 5, 2007).

Fukuda et al., "Dysfunction of Endocytic and Autophagic Pathways in a Lysosomal Storage Disease," Ann. Neurol., 59(4):700-708 (2006).

Fukuda et al., "Autophagy and Lysosomes in Pompe Disease," Autophagy, 2(4):318-320 (2006).

Fukuda et al., "Autophagy and Mistargeting of Therapeutic Enzyme in Skeletal Muscle in Pompe Disease," Mol. Therapy, 14(6):831-839 (2006).

Hashimoto et al., "Binding Sites and Binding Proteins of Binary and Ternary Complexes of Insuline-like Growth Factor II (IGF-II), IGF-binding Protein-3, and Acid-labile Subunit," J. Biol. Chem., 272(44):27936-42 (1997).

Haskell et al., "Intracellular Trafficking of the JNCL Protein CLN3," Molecular Genetics and Metabolism, 66:253-260 (1999).

Henikoff and Henikoff, "Amino acid substitution matrices from protein blocks," PNAS, 89:10915-10919 (1992).

International Search Report for PCT/US2007/023881 (2009).

Jacob et al., "Sucrase Is an Intramolecular Chaperone Located at the C-terminal End of the Sucrase-Isomaltase Enzyme Complex," J. Biol. Chem., 277:32141 (2002).

Journet et al., Proteomic analysis of human lysosomes: Application to monocytic and breast cancer cells, Proteomics 2, 1026-1040 (2002).

Kiess et al., "Biochemical Evidence that the Type II Insulin-like Growth Factor Receptor Is Identical to the Cation-independent Mannose 6-Phosphate Receptor," J. Biol. Chem., 263:9339-9344 (1988).

Kishani et al., "Recombinant human acid α-glucosidase, Major Clinical Benefits in Infantile-Onset Pompe Disease," Neurology, 68:99-109 (2007).

Kishnani et al., "A Retrospective, Multilational, Multicenter Study on the Natural History of Infantile-Onset Pompe Disease," J Pediatr, 148:671-6 (2006).

Kishnani et al., "Chinese Hamster Ovary Cell-Derived Recombinant Human Acid α-Glucosidase in Infantile-Onset Pompe Disease," J Pediatr, 148:671-6 (2006).

Lebowitz, "A breach in the blood-brain barrier," PNAS, 102(41):14485-14486 (2005).

Lemansky et al., "Synthesis and Processing of a-Galactosidase A in Human Fibroblasts," J. Biol. Chem., 262:2062-2065 (1987).

Lynch et al., "High-resolution Light Microscopy (HRLM) and Digital Analysis of Pompe Disease Pathology," J. Histochem. Cytochem., 53:63-73 (2005).

Mah et al., "Physiological Correction of Pompe Disease by Systemic Delivery of Adeno-associated Virus Serotype 1 Vectors," Molecular Thereapy (online publication) (2007).

Mahuran et al., "Proteolytic Processing of Pro-a and Pro-B Precursors from Human B-Hexosaminidase," J. Biol. Chem., 263:4612-4618 (1988).

Martiniuk et al., "Recombinant Human Acid α-Glucosidase Generated in Bacteria: Antigenic, but Enzymatically Inactive," DNA and Cell Biology, 11(9):701-706 (1992).

Meynial-Salles et al., "In vitro glycosylation of proteins: An enzymatic approach," J. Biotechnology, 1-14 (1996).

Moreland et al., "Lysosomal Acid α-Glucosidase Consists of Four Different Peptides Processed from a Single Chain Precursor," J. Biol. Chem, 280:6780-6791 (2005).

Myszka, "Kinetic, Equilibrium, and Thermodynamic Analysis of Macromolecular Interactins with BIACORE," Methods Enzymol., 323:325-340 (2000).

Newrzella et al., "Functional analysis of the glycosylaton of murine acid sphingomyenlinase," J. Biol. Chem., 271:32089-32095 (1996).

Nilsson et al., N. Engl. J. Med., 318:947-50 (1988).

Nolan et al., "Binding of Insulin-Like Growth Factor II (IGF-II) by Human Cation-Independent Mannose 6-Phosphate Receptor/IGS-II Receptor Express in Receptor-Deficient Mouse L Cells," Cell Regulation, 1(2):197-213 (Jan. 1990).

Novazyme Website printouts (2001).

Pauly et al., "Complete correction of acid α-glucosidase deficiency in Pompe disease fibroblasts in vitro, and lysosomally targeted expression in neonatalrat cardiac and skeletal muscle," Gene Therapy, 5:473-480 (1998).

PCT International Preliminary Report on Patentability for International Application No. PCT/US05/004286 (Date of issuance Aug. 14, 2006).

PCT International Search Report for International Application No. PCT/US05/004286 (Date of mailing Aug. 31, 2005).

Raben et al., "Acid α-Glucosidase Deficiency (Glycogenosis Type II, Pompe Disease)," Current Molecular Medicine, 2:145-166 (2002).

Raben, JBC, 273:19086-19092 (1998).

Samoylova et al., "Elucidation of Muscle-Binding Peptides by Phage Display Screening," Muscle and Nerve, 22:460 (1999).

Silverman, The Organic Chemistry of Drug Design and Drug Action, pp. 352-401, Academic Press, San. Diego, Calif. (1992).

Smith and Waterman, "Identification of Common Molecular Subsequences," Journal of Molecular Biology, 147:195-197 (1981).

Sperr et al., "Rituximab for the treatment of acquired antibodies to factor VIII," Haematologica, 92(1):66-71 (Jan. 2007).

Spodsberg, "Molecular Basis of Aberrant Apical Protein Transport in an Instestinal Enzyme Disorder," J. Biol. Chem., 276:23506 (2001).

Standley et al., "The role of glycosylation in ionotropic glutamate receptor ligand binding, function, and trafficking," Cellular and Molecular Life Sciences, 57:1508-1516 (1998).

Summary of the Boston IPA Board Meeting Apr. 16-17, 2002, Association for Glycogen Storage Disease (UK) Bulletin, Issue 9, May 2002, p. 14.

Supplementary European Search Report for EP 02 72 5886 (2004).

The Cytokine Facts Book (Second Ed. Academic Press, 2001). pp. 301-305; the page cited is included in form 892 and as 'appendix A'.

Thim, "A new family of growth factor-like peptides Trefoil disulphide loop structures as a common feature in breast cancer associated peptide (pS2), pancreatic spasmolytic polypeptide (PSP), and frog skin peptides (spasmolysins)," FEBS Lett., 250:85 (1989).

Thurgerg et al., "Characterization of pre- and post-treatment pathology after enzyme replacement therapy for pompe disease," Lab. Invest., 86:1208-1220 (2006).

Vaccaro, Karen, email dated Feb. 20, 2002.

Van Der Ploeg et al., "Intravenous Administration of Phosphorylated Acid a-Glucosidase Leads to Uptake of Enzyme in Heart and Skeletal Muscle of Mice," J. Clin. Invest., 87:513-518 (1991).

Vogler et al, "Overcoming the blood-brain barier with high-dose enzyme replacement therapy in murine mucopolysaccharidosis VII," PNAS USA 10.1073/pnas.0506892102, 6 pages, (2005).

Written Opinion for PCT/US2005/004286 (2005).

Written Opinion for PCT/US2007/023881 (2009).

Zubieta et al., "Response: Measuring our natural painkiller," TRENDS in Neurosciences, 25(2):69-71 (2002).

Rhee et al., "High-level expression of human insulin-like growth factor II in *Escherichia coli*," J. of Biotech., 13:293-304 (1990).

Kiess et al. "Insulin-like Growth Factor II (IGF-II) Inhibits Both the Cellular Uptake of β-Galactosidase and the Binding of to β-Galactosidase to Purified IGF-II/Mannose-6-Phosphate Receptor," J. Biol Chem., 264(8):4710-4714 (1989).

\* cited by examiner

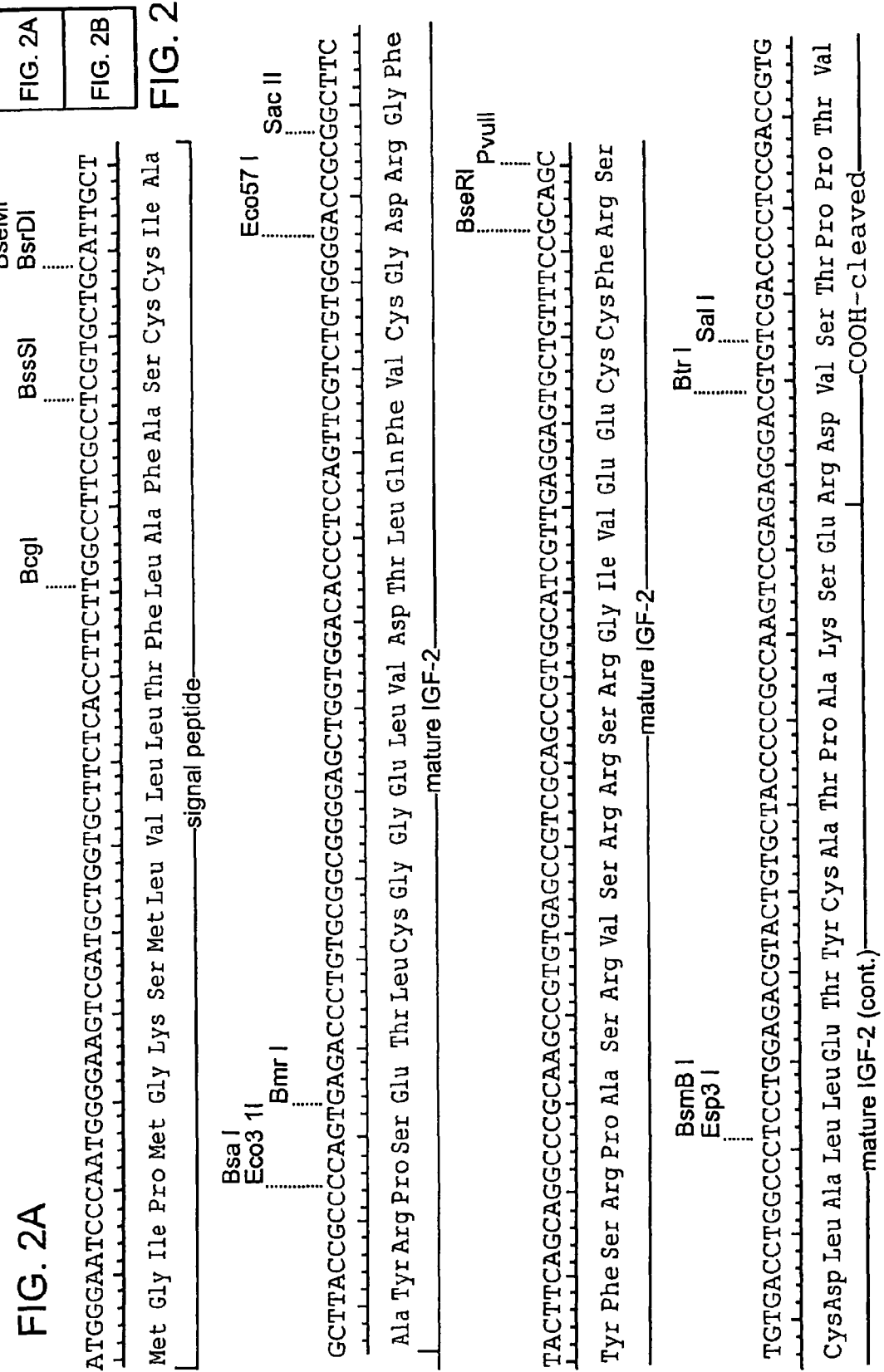

| FIG. 4A |
| FIG. 4B |
| FIG. 4C |
| FIG. 4D |
| FIG. 4E |

ATGGCCTCTAGGCTCGTCGTGTGCTGGCGGCCGCCATGCTGGTTGCAGCGGCCGTGTCGGTCGACGCGCTGCAGGGC
Met Ala Ser Arg Leu Val Arg Val Leu Ala Ala Ala Met Leu Val Ala Ala Ala Val Ser Val Asp Ala Leu Gln Gly
├──────────────────────── SAP signal peptide ────────────────────────┤

GGGATGCTGTACCCCCAGGAGAGCCCGTCGCGGGAGTGCAAGGAGCTGGACGGCCTCTGGAGCTTCCGCGCC                150
Gly Met Leu Tyr Pro Gln Glu Ser Pro Ser Arg Glu Cys Lys Glu Leu Asp Gly Leu Trp Ser Phe Arg Ala
                                           ├──────── mature β-GUS ────────

GACTTCTCTGACAACCGACGCGGGGCTTCGAGGAGCAGTGGTACCGGGCCGTGTGGGAGTCAGGCCCCACCGTG
Asp Phe Ser Asp Asn Arg Arg Gly Phe Glu Glu Gln Trp Tyr Arg Ala Val Trp Glu Ser Gly Pro Thr Val
──────── mature β-GUS ────────┤

GACATGCCAGTTCCCTCCAGCTTCAATGACATCAGCCAGGACTGGCGTCTGCGGCATTTTGTCGGCTGGGTG        300
Asp Met Pro Val Pro Ser Ser Phe Asn Asp Ile Ser Gln Asp Trp Arg Leu Arg His Phe Val Gly Trp Val
──────── mature β-GUS ────────┤

TGGTACGAACGGGAGGTGATCCTGCCGGAGCGATGGACCCAGGACCTGGCGCACAAGAGTGGTGCTGAGGATTGGCAGT

Trp Tyr Glu Arg Gly Val Ile Leu Pro Glu Arg Trp Thr Gln Asp Leu Arg Thr Arg Val Val Leu Arg Ile Gly Ser
——————————————————————————————————— mature β-GUS ———————————————————————————————————

GCCCATTCCTATGCCATCGTGTGGGTGAATGGGGTCGACACGCTAGAGCATGAGGGGGCTACCTCCCCTTC   450

Ala His Ser Tyr Ala Ile Val Trp Val Asn Gly Val Asp Thr Leu Glu His Glu Gly Gly Tyr Leu Pro Phe
——————————————————————————————————— mature β-GUS ———————————————————————————————————

GAGGCCGACATCAGCAACCTGGTGGGCCCCTGCCCTCCCGGCTCCGAATCACTATCGCCATCAACAACACA

Glu Ala Asp Ile Ser Asn Leu Val Gly Pro Ser Arg Leu Arg Ile Thr Ile Ala Ile Asn Asn Thr
——————————————————————————————————— mature β-GUS ———————————————————————————————————

CTCACCCCCACCCCTGCCACCAGGACCATCCAATACCTGACTGACACCTCCAAGTATCCCAAGGGTTAC   600

Leu Thr Pro Thr Thr Leu Pro Pro Gly Thr Thr Ile Gln Tyr Leu Thr Asp Thr Ser Lys Tyr Pro Lys Gly Tyr
——————————————————————————————————— mature β-GUS ———————————————————————————————————

TTTGTCCAGAACACATATTTTGACTTTTTCAACTACGCTGGACTGCAGCGGTCTGTACTTCTGTACACGACACCCACC

Phe Val Gln Asn Thr Tyr Phe Asp Phe Phe Asn Tyr Ala Gly Leu Gln Arg Ser Val Leu Leu Tyr Thr Thr Pro Thr
——————————————————————————————————— mature β-GUS ———————————————————————————————————

ACCTACATCGATGACATCACCGTCACCACCAGCGTGGAGCAAGACAGTGGGCTGGTGAATTACCAGATCTCT   750

Thr Tyr Ile Asp Asp Ile Thr Val Thr Thr Ser Val Glu Gln Asp Ser Gly Leu Val Asn Tyr Gln Ile Ser

FIG. 4B

```
GTCAAGGGCAGTAACCTGTTCAAGTTGGAAGTGCGTCTTTTGGATGCAGAAAACAAAGTCTGTGGCGAATGGGACTGGG
         |———————————— mature β-GUS ————————————————————————————————————————————
Val Lys Gly Ser Asn Leu Phe Lys Leu Glu Val Arg Leu Leu Asp Ala Glu Asn Lys Val Val Ala Asn Gly Thr Gly ACCCAGGGCCAACTTAAGGTGCCAGGTGTCAGCCTCTGGTGGCCGTACCTGATGCACGAACGCCCTGCCTAT  900
—————————————————————————————————— mature β-GUS ———————————————————————
Thr Gln Gly Gln Leu Lys Val Pro Gly Val Ser Leu Trp Trp Pro Tyr Leu Met His Glu Arg Pro Ala Tyr CTGTATTCATTGGAGGTGCAGCTGACTGCACAGAGTCCAGTCCTGTGTCTGACTTCTACACACTCCCTGTGGGG
————————————————————————————————— mature β-GUS —————————————————————
Leu Tyr Ser Leu Glu Val Gln Leu Thr Ala Gln Ser Pro Val Ser Asp Phe Tyr Thr Leu Pro Val Gly ATCCGCACTGTGGCTGTCACCAAGAGCCAGTTCCTCATCAATGGGAAACCTTTCTATTCCACGGTGTCAAC  1050
————————————————————————————————— mature β-GUS —————————————————————
Ile Arg Thr Val Ala Val Thr Lys Ser Gln Phe Leu Ile Asn Gly Lys Pro Phe Tyr Phe His Gly Val Asn AAGCATGAGGATGCGGACATCCGAGGAAGGGCTTCGACTGGCCGCTGCTGGTGAAGGACTTCAACCTGCTTCGCTGG
————————————————————————————————— mature β-GUS —————————————————————
Lys His Glu Asp Ala Asp Ile Arg Gly Lys Gly Phe Asp Trp Pro Leu Leu Val Lys Asp Phe Asn Leu Arg Trp CTTGGTGCCAACGCTTTCCGTACCAGCCACTACCCCTATGCAGAGGAAGTGATGCAGATGTGTGACCGCTAT  1200
—————————————————————————————————— mature β-GUS ————————————————————
Leu Gly Ala Asn Ala Phe Arg Thr Ser His Tyr Pro Tyr Ala Glu Glu Val Met Gln Met Cys Asp Arg Tyr
```

FIG. 4C

GGGATTGTGGTCATCGATGAGTGTCCCGGCGTGGGTCTGGCGCTGCCGCTGCCGGCAGTTCTTCAACAACGTTTCTCTGCATCAC
                                  —————————————mature β-GUS—————————————
Gly  Ile  Val  Val  Ile  Asp Glu Cys Pro Gly Val Gly Leu Ala Leu Pro Gln Phe Phe Asn Asn Val Ser Leu His His CACATGCAGGTGATGGAAGAAGTGGTGCGTAGGACAAGAACCACCCCGGTCGTGATGTGGTCTGTGGCC 1350
                                  —————————————mature β-GUS—————————————
His Met Gln Val Met Glu Glu Val Val  Arg Arg Asp Lys Asn His Pro Ala Val Val Met Trp Ser Val Ala AACGAGCCTGCGTCCCACCTAGAATCTGCTGGCTACTACTTGAAGATGGTGATCGCTCACACCAAATCCTTGGACCCC
                                    —————————————mature β-GUS—————————————
Asn Glu Pro Ala Ser His Leu Glu Ser Ala Gly Tyr Tyr Leu Lys Met Val Ile Ala His  Thr Lys Ser Leu Asp Pro TCCCGGCCTGTGACCTTTGTGAGCAACTCTAACTATGCAGCAGCAGACAAGGGGCTCCGTATGTGGATGTGATC 1500
                                    —————————————mature β-GUS—————————————
Ser Arg Pro Val Thr Phe Val  Ser Asn Ser Asn Tyr Ala  Ala Ala Asp Lys Gly Ala Pro  Tyr Val Asp Val  Ile TGTTTGAACAGCTACTACTCTTGGTATCACGACTACGGCCACCTGGAGTTGATTCAGCTGCAGCTGGCCACCCAGTTT
                                  —————————————mature β-GUS—————————————
Cys Leu Asn Ser  Tyr Tyr Ser Trp Tyr  His Asp Tyr  Gly His  Leu Glu Leu Ile   Gln Leu Gln Leu Ala  Thr  Gln Phe GAGAACTGGTATAAGAAGTATCAGAAGCCCATTATTCAGAGCGAGTATGGAGCAGAAACGATTGCAGGGTTT 1650
                                  —————————————mature β-GUS—————————————
Glu Asn Trp Tyr Lys Lys Tyr  Gln Lys Pro  Ile   Ile  Gln Ser Glu Tyr  Gly Ala Glu Thr  Ile  Ala Gly Phe

FIG. 4D

```
CACCAGGATCCACCTCTGATGTTCACTGAAGAGTACCAGAAAAGTCTGCTAGAGCAGTACCATCTGGGTCTGGATCAA
                                  |———————————————————— mature β-GUS ————————————————————
His Gln Asp Pro Pro Leu Met Phe Thr Glu Glu Tyr Gln Lys Ser Leu Leu Glu Gln Tyr His Leu Gly Leu Asp Gln
                                                                                                      1800
AAACGCGAGAAAATATGTGGTTTGGAGAGCTCATTTGCCGATTTCATGACTGAACAGTCACCGACG
———————————————————————————— mature β-GUS ————————————————————————————
Lys Arg Arg Lys Tyr Val Val Gly Glu Leu Ile Trp Asn Phe Ala Asp Phe Met Thr Glu Gln Ser Pro Thr
AGAGTGCTGGGGAATAAAAAGGGGATCTTCACTCGGCAGAGACAACCAAAAAGTGCAGGCGTTCCTTTTGCGAGAGAGA
———————————————————————————— mature β-GUS ————————————————————————————               1950
Arg Val Leu Gly Asn Lys Lys Gly Ile Phe Thr Arg Gln Arg Gln Pro Lys Ser Ala Ala Phe Leu Leu Arg Glu Arg
TACTGGAAGATTGCCAATGAAACCAGGTATCCCCACTCAGTAGCCAAGTCACAATGTTTGGAAAACAGCCCG
——————————————————————————— mature β-GUS ——————————————————————————————
Tyr Trp Lys Ile Ala Asn Glu Thr Arg Tyr Pro His Ser Val Ala Lys Ser Gln Cys Leu Glu Asn Ser Pro
TTTACTGGCGCGGGCTACCGCCCGAGCGAGACGCTGTGCGGCGAGCTGGTGGACACGCTGCAGTTCGTGTGC
|——bridge——|———————————————————————— IGF-II —————————————————————————————
Phe Thr Gly Ala Pro Ala Tyr Arg Pro Ser Glu Thr Leu Cys Gly Gly Glu Leu Val Asp Thr Leu Gln Phe Val Cys
GGCGACCGCGGCTTCTACTTCAGCCGCCCCGCCAGCCGCGTGAGCCGCCGCAGCCGCGGCATCGTGGAGGAG  2100
—————————————————————————————— IGF-II ——————————————————————————————————
Gly Asp Arg Gly Phe Tyr Phe Ser Arg Pro Ala Ser Arg Val Ser Arg Arg Ser Arg Gly Ile Val Glu Glu
TGCTGCTTCCGCAGCTGCGACCTGGCGCTGCTGGAGACGTACTGCGCGACGCCGGCGAAGTCGGAGTAA   2169
—————————————————————————————— IGF-II ——————————————————————————————|
Cys Cys Phe Arg Ser Cys Asp Leu Ala Leu Leu Glu Thr Tyr Cys Ala Thr Pro Ala Lys Ser Glu  .
```

FIG. 4E

METHOD FOR TARGETING LYSOSOMAL ENZYMES

REFERENCE TO RELATED APPLICATIONS

This application is a continuation of U.S. Ser. No. 10/272,483, filed Oct. 16, 2002, U.S. Pat. No. 7,560,424 which claims the benefit of U.S. Ser. No. 60/287,531, filed Apr. 30, 2001; U.S. Ser. No. 60/304,609, filed Jul. 10, 2001; U.S. Ser. No. 60/329,461, filed Oct. 15, 2001, U.S. Ser. No. 60/351,276, filed Jan. 23, 2002; U.S. Ser. No. 10/136,841, filed Apr. 30, 3002; U.S. Ser. No. 60/384,452, filed May 29, 2002; U.S. Ser. No. 60/386,019, filed Jun. 5, 2002; and U.S. Ser. No. 60/408,816, filed Sep. 6, 2002; the contents of which are incorporated by reference.

This invention provides a means for specifically delivering proteins to a targeted subcellular compartment of a mammalian cell. The ability to target proteins to a subcellular compartment is of great utility in the treatment of metabolic diseases such as lysosomal storage diseases, a class of over 40 inherited disorders in which particular lysosomal enzymes are absent or deficient.

BACKGROUND

Enzyme deficiencies in cellular compartments such as the golgi, the endoplasmic reticulum, and the lysosome cause a wide variety of human diseases. For example, lysyl hydroxylase, an enzyme normally in the lumen of the endoplasmic reticulum, is required for proper processing of collagen; absence of the enzyme causes Ehlers-Danlos syndrome type VI, a serious connective tissue disorder. GnT II, normally found in the golgi, is required for normal glycosylation of proteins; absence of GnT II causes leads to defects in brain development. More than forty lysosomal storage diseases (LSDs) are caused, directly or indirectly, by the absence of one or more proteins in the lysosome.

Mammalian lysosomal enzymes are synthesized in the cytosol and traverse the ER where they are glycosylated with N-linked, high mannose type carbohydrate. In the golgi, the high mannose carbohydrate is modified on lysosomal proteins by the addition of mannose-6-phosphate (M6P) which targets these proteins to the lysosome. The M6P-modified proteins are delivered to the lysosome via interaction with either of two M6P receptors. The most favorable form of modification is when two M6Ps are added to a high mannose carbohydrate.

Enzyme replacement therapy for lysosomal storage diseases (LSDs) is being actively pursued. Therapy, except in Gaucher's disease, generally requires that LSD proteins be taken up and delivered to the lysosomes of a variety of cell types in an M6P-dependent fashion. One possible approach involves purifying an LSD protein and modifying it to incorporate a carbohydrate moiety with M6P. This modified material may be taken up by the cells more efficiently than unmodified LSD proteins due to interaction with M6P receptors on the cell surface. However, because of the time and expense required to prepare, purify and modify proteins for use in subcellular targeting, a need for new, simpler, more efficient, and more cost-effective methods for targeting therapeutic agents to a cellular compartment remains.

SUMMARY OF THE INVENTION

The present invention facilitates the treatment of metabolic diseases by providing targeted protein therapeutics that localize to a subcellular compartment of a cell where the therapeutic is needed. The invention simplifies preparation of targeted protein therapeutics by reducing requirements for posttranslational or postsynthesis processing of the protein. For example, a targeted therapeutic of the present invention can be synthesized as a fusion protein including a therapeutic domain and a domain that targets the fusion protein to a correct subcellular compartment. ("Fusion protein," as used herein, refers to a single polypeptide having at least two domains that are not normally present in the same polypeptide. Thus, naturally occurring proteins are not "fusion proteins" as used herein.) Synthesis as a fusion protein permits targeting of the therapeutic domain to a desired subcellular compartment without complications associated with chemical crosslinking of separate therapeutic and targeting domains, for example.

The invention also permits targeting of a therapeutic to a lysosome in an M6P-independent manner. Accordingly, the targeted therapeutic need not be synthesized in a mammalian cell, but can be synthesized chemically or in a bacterium, yeast, protozoan, or other organism regardless of glycosylation pattern, facilitating production of the targeted therapeutic with high yield and comparatively low cost. The targeted therapeutic can be synthesized as a fusion protein, further simplifying production, or can be generated by associating independently-synthesized therapeutic agents and targeting moieties.

The present invention permits lysosomal targeting of therapeutics without the need for M6P addition to high mannose carbohydrate. It is based in part on the observation that one of the 2 M6P receptors also binds other ligands with high affinity. For example, the cation-independent mannose-6-phosphate receptor is also known as the insulin-like growth factor 2 (IGF-II) receptor because it binds IGF-II with high affinity. This low molecular weight polypeptide interacts with three receptors, the insulin receptor, the IGF-I receptor and the M6P/IGF-II receptor. It is believed to exert its biological effect primarily through interactions with the former two receptors while interaction with the cation-independent M6P receptor is believed to result predominantly in the IGF-II being transported to the lysosome where it is degraded.

Accordingly, the invention relates in one aspect to a targeted therapeutic including a targeting moiety and a therapeutic agent that is therapeutically active in a mammalian lysosome. "Therapeutically active," as used herein, encompasses at least polypeptides or other molecules that provide an enzymatic activity to a cell or a compartment thereof that is deficient in that activity. "Therapeutically active" also encompasses other polypeptides or other molecules that are intended to ameliorate or to compensate for a biochemical deficiency in a cell, but does not encompass molecules that are primarily cytotoxic or cytostatic, such as chemotherapeutics.

In one embodiment, the targeting moiety is a means (e.g. a molecule) for binding the extracellular domain of the human cation-independent M6P receptor in an M6P-independent manner when the receptor is present in the plasma membrane of a target cell. In another embodiment, the targeting moiety is an unglycosylated lysosomal targeting domain that binds the extracellular domain of the human cation-independent M6P receptor. In either embodiment, the targeting moiety can include, for example, IGF-II; retinoic acid or a derivative thereof; a protein having an amino acid sequence at least 70% identical to a domain of urokinase-type plasminogen activator receptor; an antibody variable domain that recognizes the receptor; or variants thereof. In some embodiments, the targeting moiety binds to the receptor with a submicromolar dissociation constant (e.g. less than $10^{-8}$ M, less than $10^{-9}$ M, less than $10^{-10}$ M, or between $10^{-7}$ M and $10^{-11}$ M) at or about pH 7.4 and with an dissociation constant at or about pH 5.5 of at least $10^{-6}$ M and at least ten times the dissociation constant at or about pH 7.4. In particular embodiments, the means for binding binds to the extracellular domain at least 10-fold less avidly (i.e. with at least a ten-fold greater dissociation constant) at or about pH 5.5 than at or about pH 7.4; in one embodiment, the dissociation constant at or about pH 5.5 is at least $10^{-6}$ M. In a further embodiment, association of the targeted therapeutic with the means for binding is destabilized by a pH change from at or about pH 7.4 to at or about pH 5.5.

In another embodiment, the targeting moiety is a lysosomal targeting domain that binds the extracellular domain of the human cation-independent M6P receptor but does not bind a mutein of the receptor in which amino acid 1572 is changed from isoleucine to threonine, or binds the mutein with at least ten-fold less affinity (i.e. with at least a ten-fold greater dissociation constant). In another embodiment, the targeting moiety is a lysosomal targeting domain capable of binding a receptor domain consisting essentially of repeats 10-15 of the human cation-independent M6P receptor: the lysosomal targeting domain can bind a protein that includes repeats 10-15 even if the protein includes no other moieties that bind the lysosomal targeting domain. Preferably, the lysosomal targeting domain can bind a receptor domain consisting essentially of repeats 10-13 of the human cation-independent mannose-6-phosphate receptor. More preferably, the lysosomal targeting domain can bind a receptor domain consisting essentially of repeats 11-12, repeat 11, or amino acids 1508-1566 of the human cation-independent M6P receptor. In each of these embodiments, the lysosomal targeting domain preferably binds the receptor or receptor domain with a submicromolar dissociation constant at or about pH 7.4. In one preferred embodiment, the lysosomal targeting domain binds with an dissociation constant of about $10^{-7}$ M. In another preferred embodiment, the dissociation constant is less than about $10^{-7}$ M.

In another embodiment, the targeting moiety is a binding moiety sufficiently duplicative of human IGF-II such that the binding moiety binds the human cation-independent M6P receptor. The binding moiety can be sufficiently duplicative of IGF-II by including an amino acid sequence sufficiently homologous to at least a portion of IGF-II, or by including a molecular structure sufficiently representative of at least a portion of IGF-II, such that the binding moiety binds the cation-independent M6P receptor. The binding moiety can be an organic molecule having a three-dimensional shape representative of at least a portion of IGF-II, such as amino acids 48-55 of human IGF-II, or at least three amino acids selected from the group consisting of amino acids 8, 48, 49, 50, 54, and 55 of human IGF-II. A preferred organic molecule has a hydrophobic moiety at a position representative of amino acid 48 of human IGF-II and a positive charge at or about pH 7.4 at a position representative of amino acid 49 of human IGF-II. In one embodiment, the binding moiety is a polypeptide including a polypeptide having antiparallel alpha-helices separated by not more than five amino acids. In another embodiment, the binding moiety includes a polypeptide with the amino acid sequence of IGF-I or of a mutein of IGF-I in which amino acids 55-56 are changed and/or amino acids 1-4 are deleted or changed. In a further embodiment, the binding moiety includes a polypeptide with an amino acid sequence at least 60% identical to human IGF-II; amino acids at positions corresponding to positions 54 and 55 of human IGF-II are preferably uncharged or negatively charged at or about pH 7.4.

In one embodiment, the targeting moiety is a polypeptide comprising the amino acid sequence phenylalanine-arginine-serine. In another embodiment, the targeting moiety is a polypeptide including an amino acid sequence at least 75% homologous to amino acids 48-55 of human IGF-II. In another embodiment, the targeting moiety includes, on a single polypeptide or on separate polypeptides, amino acids 8-28 and 41-61 of human IGF-II. In another embodiment, the targeting moiety includes amino acids 41-61 of human IGF-II and a mutein of amino acids 8-28 of human IGF-II differing from the human sequence at amino acids 9, 19, 26, and/or 27.

In some embodiments, the association of the therapeutic agent with the targeting moiety is labile at or about pH 5.5. In a preferred embodiment, association of the targeting moiety with the therapeutic agent is mediated by a protein acceptor (such as imidazole or a derivative thereof such as histidine) having a pKa between 5.5 and 7.4. Preferably, one of the therapeutic agent or the targeting moiety is coupled to a metal, and the other is coupled to a pH-dependent metal binding moiety.

In another aspect, the invention relates to a therapeutic fusion protein including a therapeutic domain and a subcellular targeting domain. The subcellular targeting domain binds to an extracellular domain of a receptor on an exterior surface of a cell. Upon internalization of the receptor, the subcellular targeting domain permits localization of the therapeutic domain to a subcellular compartment such as a lysosome, an endosome, the endoplasmic reticulum (ER), or the golgi complex, where the therapeutic domain is therapeutically active. In one embodiment, the receptor undergoes constitutive endocytosis. In another embodiment, the therapeutic domain has a therapeutic enzymatic activity. The enzymatic activity is preferably one for which a deficiency (in a cell or in a particular compartment of a cell) is associated with a human disease such as a lysosomal storage disease.

In further aspects, the invention relates to nucleic acids encoding therapeutic proteins and to cells (e.g. mammalian cells, insect cells, yeast cells, protozoans, or bacteria) comprising these nucleic acids. The invention also provides methods of producing the proteins by providing these cells with conditions (e.g. in the context of in vitro culture or by maintaining the cells in a mammalian body) permitting expression of the proteins. The proteins can be harvested thereafter (e.g. if produced in vitro) or can be used without an intervening harvesting step (e.g. if produced in vivo in a patient). Thus, the invention also provides methods of treating a patient by administering a therapeutic protein (e.g. by injection, in situ synthesis, or otherwise), by administering a nucleic acid encoding the protein (thereby permitting in vivo protein synthesis), or by administering a cell comprising a nucleic acid encoding the protein. In one embodiment, the method includes synthesizing a targeted therapeutic including a therapeutic agent that is therapeutically active in a mammalian lysosome and a targeting moiety that binds human cation-independent mannose-6-phosphate receptor in a mannose-6-phosphate-independent manner, and administering the targeted therapeutic to a patient. The method can also include identifying the targeting moiety (e.g. by a recombinant display technique such as phage display, bacterial display, or yeast two-hybrid or by screening libraries for requisite binding properties). In another embodiment, the method includes providing (e.g. on a computer) a molecular model defining a three-dimensional shape representative of at least a portion of human IGF-II; identifying a candidate IGF-II analog having a three-dimensional shape representative of at least a portion of IGF-II (e.g. amino acids 48-55), and producing a therapeutic agent that is active in a mammalian lysosome and directly or indirectly bound to the candidate IGF-II analog. The method can also include determining whether the candidate IGF-II analog binds to the human cation-independent M6P receptor.

This invention also provides methods for producing therapeutic proteins that are targeted to lysosomes and/or across the blood-brain barrier and that possess an extended half-life in circulation in a mammal. The methods include producing an underglycosylated therapeutic protein. As used herein, "underglycosylated" refers to a protein in which one or more carbohydrate structures that would normally be present if the protein were produced in a mammalian cell (such as a CHO cell) has been omitted, removed, modified, or masked, thereby extending the half-life of the protein in a mammal. Thus, a protein may be actually underglycosylated due to the absence of one or more carbohydrate structures, or functionally underglycosylated by modification or masking of one or more carbohydrate structures that promote clearance from circulation. For example, a structure could be masked (i) by the addition of one or more additional moieties (e.g. carbohydrate groups, phosphate groups, alkyl groups, etc.) that interfere with recognition of the structure by a mannose or asialoglycoprotein receptor, (ii) by covalent or noncovalent association of the glycoprotein with a binding moiety, such as a lectin or an extracellular portion of a mannose or asialoglycoprotein receptor, that interferes with binding to those receptors in vivo, or (iii) any other modification to the polypeptide or carbohydrate portion of a glycoprotein to reduce its clearance from the blood by masking the presence of all or a portion of the carbohydrate structure.

In one embodiment, the therapeutic protein includes a peptide targeting moiety (e.g. IGF-I, IGF-II, or a portion thereof effective to bind a target receptor) that is produced in a host (e.g. bacteria or yeast) that does not glycosylate proteins as conventional mammalian cells (e.g. Chinese hamster ovary (CHO) cells) do. For example, proteins produced by the host cell may lack terminal mannose, fucose, and/or N-acetylglucosamine residues, which are recognized by the mannose receptor, or may be completely unglycosylated. In another embodiment, the therapeutic protein, which may be produced in mammalian cells or in other hosts, is treated chemically or enzymatically to remove one or more carbohydrate residues (e.g. one or more mannose, fucose, and/or N-acetylglucosamine residues) or to modify or mask one or more carbohydrate residues. Such a modification or masking may reduce binding of the therapeutic protein to the hepatic mannose and/or asialoglycoprotein receptors. In another embodiment, one or more potential glycosylation sites are removed by mutation of the nucleic acid encoding the targeted therapeutic protein, thereby reducing glycosylation of the protein when synthesized in a mammalian cell or other cell that glycosylates proteins.

BRIEF DESCRIPTION OF THE DRAWINGS

FIG. 4 is a depiction of a preferred embodiment of the invention, incorporating a signal peptide sequence, the mature human β-glucuronidase sequence, a bridge of three amino acids, and an IGF-II sequence. The depicted nucleic acid is SEQ ID NO:5, and the encoded protein is SEQ ID NO:6.

DETAILED DESCRIPTION OF THE INVENTION

Figure 1:
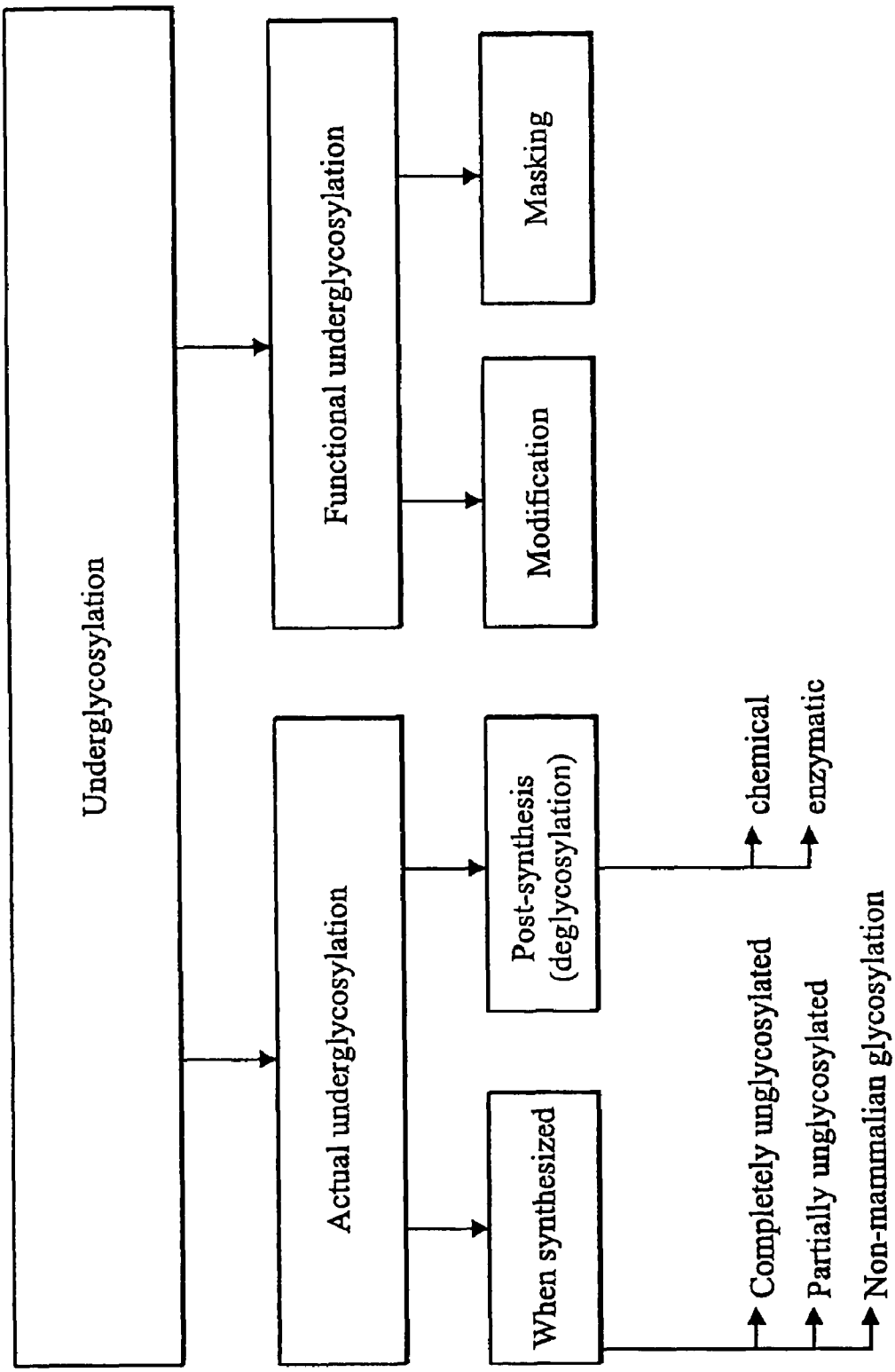
FIG. 1 depicts several types of underglycosylation.

As used herein, "glycosylation independent lysosomal targeting" and "GILT" refer to lysosomal targeting that is mannose-6-phosphate-independent.

As used herein, "GILT construct" refers to a construct including a mannose-6-phosphate-independent lysosomal targeting portion and a therapeutic portion effective in a mammalian lysosome.

As used herein, "GUS" refers to β-glucuronidase, an exemplary therapeutic portion.

As used herein, "GUSΔC18" refers to GUS with a deletion of the C-terminal 18 amino acids, removing a potential proteolysis site.

As used herein, "GUS-GILT" refers to a GILT construct with GUS coupled to an IGF-II targeting portion.

All references to amino acid positions in IGF-II refer to the positions in mature human IGF-II. Thus, for example, positions 1, 2, and 3 are occupied by alanine, tyrosine, and arginine, respectively.

As used herein, GILTΔ1-7 refers to an IGF-II targeting portion with a deletion of the N-terminal 7 amino acids.

As used herein, GUSΔC18-GILTΔ1-7 refers to a fusion protein in which GUSΔC18 is fused to the N-terminus of GILTΔ1-7.

The present invention facilitates treatment of metabolic diseases by providing targeted therapeutics that, when provided externally to a cell, enter the cell and localize to a subcellular compartment where the targeted therapeutic is active. The targeted therapeutic includes at least a therapeutic agent and a targeting moiety, such as a subcellular targeting domain of a protein, or, for lysosomal targeting, a means (e.g. a protein, peptide, peptide analog, or organic chemical) for binding the human cation-independent mannose-6-phosphate receptor.

Association Between Therapeutic Agent and Targeting Moiety

The therapeutic agent and the targeting moiety are necessarily associated, directly or indirectly. In one embodiment, the therapeutic agent and the targeting moiety are non-covalently associated. The association is preferably stable at or about pH 7.4. For example, the targeting moiety can be biotinylated and bind avidin associated with the therapeutic agent. Alternatively, the targeting moiety and the therapeutic agent can each be associated (e.g. as fusion proteins) with different subunits of a multimeric protein. In another embodiment, the targeting moiety and the therapeutic agent are crosslinked to each other (e.g. using a chemical crosslinking agent).

In a preferred embodiment, the therapeutic agent is fused to the targeting moiety as a fusion protein. The targeting moiety can be at the amino-terminus of the fusion protein, the carboxy-terminus, or can be inserted within the sequence of the therapeutic agent at a position where the presence of the targeting moiety does not unduly interfere with the therapeutic activity of the therapeutic agent.

Where the therapeutic agent is a heteromeric protein, one or more of the subunits can be associated with a targeting portion. Hexosaminidase A, for example, a lysosomal protein affected in Tay-Sachs disease, includes an alpha subunit and a beta subunit. The alpha subunit, the beta subunit, or both can be associated with a targeting moiety in accordance with the present invention. If, for example, the alpha subunit is associated with a targeting moiety and is coexpressed with the beta subunit, an active complex is formed and targeted appropriately (e.g. to the lysosome).

For targeting a therapeutic to the lysosome, the therapeutic agent can be connected to the targeting moiety through an interaction that is disrupted by decreasing the pH from at or about 7.4 to at or about 5.5. The targeting moiety binds a receptor on the exterior of a cell; the selected receptor is one that undergoes endocytosis and passes through the late endosome, which has a pH of about 5.5. Thus, in the late endosome, the therapeutic agent dissociates from the targeting moiety and proceeds to the lysosome, where the therapeutic agent acts. For example, a targeting moiety can be chemically modified to incorporate a chelating agent (e.g. EDTA, EGTA, or trinitrilotriacetic acid) that tightly binds a metal ion such as nickel. The targeting moiety (e.g. GUS) can be expressed as a fusion protein with a six-histidine tag (e.g. at the amino-terminus, at the carboxy-terminus, or in a surface-accessible flexible loop). At or about pH 7.4, the six-histidine tag is substantially deprotonated and binds metal ions such as nickel with high affinity. At or about pH 5.5, the six-histidine tag is substantially protonated, leading to release of the nickel and, consequently, release of the therapeutic agent from the targeting moiety.

Therapeutic Agent

While methods and compositions of the invention are useful for producing and delivering any therapeutic agent to a subcellular compartment, the invention is particularly useful for delivering gene products for treating metabolic diseases.

Preferred LSD genes are shown in Table 1, and preferred genes associated with golgi or ER defects are shown in Table 2. In a preferred embodiment, a wild-type LSD gene product is delivered to a patient suffering from a defect in the same LSD gene. In alternative embodiments, a functional sequence or species variant of the LSD gene is used. In further embodiments, a gene coding for a different enzyme that can rescue an LSD gene defect is used according to methods of the invention.

TABLE 1

Lysosomal Storage Diseases and associated enzyme defects

| Disease Name | Enzyme Defect | Substance Stored |
|---|---|---|
| A. Glycogenosis Disorders | | |
| Pompe Disease | Acid-α1, 4-Glucosidase | Glycogen α 1-4 linked Oligosaccharides |
| B. Glycolipidosis Disorders | | |
| GM1 Gangliodsidosis | β-Galactosidase | $GM_1$ Ganliosides |
| Tay-Sachs Disease | β-Hexosaminidase A | $GM_2$ Ganglioside |
| GM2 Gangliosidosis: AB Variant | $GM_2$ Activator Protein | $GM_2$ Ganglioside |
| Sandhoff Disease | β-Hexosaminidase A&B | $GM_2$ Ganglioside |
| Fabry Disease | α-Galactosidase A | Globosides |
| Gaucher Disease | Glucocerebrosidase | Glucosylceramide |
| Metachromatic Leukodystrophy | Arylsulfatase A | Sulphatides |
| Krabbe Disease | Galactosylceramidase | Galactocerebroside |
| Niemann-Pick, Types A and B | Acid Sphingomyelinase | Sphingomyelin |
| Niemann-Pick, Type C | Cholesterol Esterification Defect | Sphingomyelin |
| Nieman-Pick, Type D | Unknown | Sphingomyelin |
| Farber Disease | Acid Ceramidase | Ceramide |
| Wolman Disease | Acid Lipase | Cholesteryl Esters |
| C. Mucopolysaccharide Disorders | | |
| Hurler Syndrome (MPS IH) | α-L-Iduronidase | Heparan & Dermatan Sulfates |
| Scheie Syndrome (MPS IS) | α-L-Iduronidase | Heparan & Dermatan, Sulfates |
| Hurler-Scheie (MPS IH/S) | α-L-Iduronidase | Heparan & Dermatan Sulfates |
| Hunter Syndrome (MPS II) | Iduronate Sulfatase | Heparan & Dermatan Sulfates |
| Sanfilippo A (MPS IIIA) | Heparan N-Sulfatase | Heparan Sulfate |
| Sanfilippo B (MPS IIIB) | α-N-Acetylglucosaminidase | Heparan Sulfate |
| Sanfilippo C (MPS IIIC) | Acetyl-CoA-Glucosaminide Acetyltransferase | Heparan Sulfate |
| Sanfilippo D (MPS IIID) | N-Acetylglucosamine-6-Sulfatase | Heparan Sulfate |
| Morquio A (MPS IVA) | Galactosamine-6-Sulfatase | Keratan Sulfate |
| Morquio B (MPS IVB) | β-Galactosidase | Keratan Sulfate |
| Maroteaux-Lamy (MPS VI) | Arylsulfatase B | Dermatan Sulfate |
| Sly Syndrome (MPS VII) | β-Glucuronidase | |
| D. Oligosaccharide/Glycoprotein Disorders | | |
| α-Mannosidosis | α-Mannosidase | Mannose/Oligosaccharides |
| β-Mannosidosis | β-Mannosidase | Mannose/Oligosaccharides |
| Fucosidosis | α-L-Fucosidase | Fucosyl Oligosaccharides |
| Asparylglucosaminuria | N-Aspartyl-β-Glucosaminidase | Asparylglucosamine Asparagines |
| Sialidosis (Mucolipidosis I) | α-Neuraminidase | Sialyloligosaccharides |
| Galactosialidosis (Goldberg Syndrome) | Lysosomal Protective Protein Deficiency | Sialyloligosaccharides |
| Schindler Disease | α-N-Acetyl-Galactosaminidase | |

TABLE 1-continued

Lysosomal Storage Diseases and associated enzyme defects

| Disease Name | Enzyme Defect | Substance Stored |
|---|---|---|
| E. Lysosomal Enzyme Transport Disorders | | |
| Mucolipidosis II (I-Cell Disease) | N-Acetylglucosamine-1-Phosphotransferase | Heparan Sulfate |
| Mucolipidosis III (Pseudo-Hurler Polydystrophy) | Same as ML II | |
| F. Lysosomal Membrane Transport Disorders | | |
| Cystinosis | Cystine Transport Protein | Free Cystine |
| Salla Disease | Sialic Acid Transport Protein | Free Sialic Acid and Glucuronic Acid |
| Infantile Sialic Acid Storage Disease | Sialic Acid Transport Protein | Free Sialic Acid and Glucuronic Acid |
| G. Other | | |
| Batten Disease (Juvenile Neuronal Ceroid Lipofuscinosis) | Unknown | Lipofuscins |
| Infantile Neuronal Ceroid Lipofuscinosis | Palmitoyl-Protein Thioesterase | Lipofuscins |
| Mucolipidosis IV | Unknown | Gangliosides & Hyaluronic Acid |
| Prosaposin | Saposins A, B, C or D | |

TABLE 2

Diseases of the golgi and ER

| Disease Name | Gene and Enzyme Defect | Features |
|---|---|---|
| Ehlers-Danlos Syndrome Type VI | PLOD1 lysyl hydroxylase | Defect in lysyl hydroxylation of Collagen; located in ER lumen |
| Type Ia glycoge storage disease | glucose6 phosphatase | Causes excessive accumulation of Glycogen in the liver, kidney, and Intestinal mucosa; enzyme is transmembrane but active site is ER lumen |
| Congenital Disorders of Glycosylation | | |
| CDG Ic | ALG6 α1,3 glucosyltransferase | Defects in N-glycosylation ER lumen |
| CDG Id | ALG3 α1,3 mannosyltransferase | Defects in N-glycosylation ER transmembrane protein |
| CDG IIa | MGAT2 N-acetylglucosaminyl-transferase II | Defects in N-glycosylation golgi transmembrane protein |
| CDG IIb | GCS1 α1,2-Glucosidase I | Defect in N glycosylation ER membrane bound with lumenal catalytic domain releasable by proteolysis |

One particularly preferred therapeutic agent is glucocerebrosidase, currently manufactured by Genzyme as an effective enzyme replacement therapy for Gaucher's Disease. Currently, the enzyme is prepared with exposed mannose residues, which targets the protein specifically to cells of the macrophage lineage. Although the primary pathology in type 1 Gaucher patients are due to macrophage accumulating glucocerebroside, there can be therapeutic advantage to delivering glucocerebrosidase to other cell types. Targeting glucocerebrosidase to lysosomes using the present invention would target the agent to multiple cell types and can have a therapeutic advantage compared to other preparations.

Subcellular Targeting Domains

The present invention permits targeting of a therapeutic agent to a lysosome using a protein, or an analog of a protein, that specifically binds a cellular receptor for that protein. The exterior of the cell surface is topologically equivalent to endosomal, lysosomal, golgi, and endoplasmic reticulum compartments. Thus, endocytosis of a molecule through interaction with an appropriate receptor(s) permits transport of the molecule to any of these compartments without crossing a membrane. Should a genetic deficiency result in a deficit of a particular enzyme activity in any of these compartments, delivery of a therapeutic protein can be achieved by tagging it with a ligand for the appropriate receptor(s).

Multiple pathways directing receptor-bound proteins from the plasma membrane to the golgi and/or endoplasmic reticulum have been characterized. Thus, by using a targeting portion from, for example, SV40, cholera toxin, or the plant toxin ricin, each of which coopt one or more of these subcellular trafficking pathways, a therapeutic can be targeted to the desired location within the cell. In each case, uptake is initiated by binding of the material to the exterior of the cell. For example, SV40 binds to MHC class I receptors, cholera toxin binds to GM1 ganglioside molecules and ricin binds to glycolipids and glycoproteins with terminal galactose on the surface of cells. Following this initial step the molecules reach the ER by a variety of pathways. For example, SV40 undergoes caveolar endocytosis and reaches the ER in a two step process that bypasses the golgi whereas cholera toxin undergoes caveolar endocytosis but traverses the golgi before reaching the ER.

If a targeting moiety related to cholera toxin or ricin is used, it is important that the toxicity of cholera toxin or ricin be avoided. Both cholera toxin and ricin are heteromeric proteins, and the cell surface binding domain and the catalytic activities responsible for toxicity reside on separate polypeptides. Thus, a targeting moiety can be constructed that includes the receptor-binding polypeptide, but not the polypeptide responsible for toxicity. For example, in the case of ricin, the B subunit possesses the galactose binding activity responsible for internalization of the protein, and can be fused to a therapeutic protein. If the further presence of the A subunit improves subcellular localization, a mutant version (mutein) of the A chain that is properly folded but catalytically inert can be provided with the B subunit-therapeutic agent fusion protein.

Proteins delivered to the golgi can be transported to the endoplasmic reticulum (ER) via the KDEL receptor, which retrieves ER-targeted proteins that have escaped to the golgi. Thus, inclusion of a KDEL motif at the terminus of a targeting domain that directs a therapeutic protein to the golgi permits subsequent localization to the ER. For example, a targeting moiety (e.g. an antibody, or a peptide identified by high-throughput screening such as phage display, yeast two hybrid, chip-based assays, and solution-based assays) that binds the cation-independent M6P receptor both at or about pH 7.4 and at or about pH 5.5 permits targeting of a therapeutic agent to the golgi; further addition of a KDEL motif permits targeting to the ER.

Lysosomal Targeting Moieties

The invention permits targeting of a therapeutic agent to a lysosome. Targeting may occur, for example, through binding of a plasma membrane receptor that later passes through a lysosome. Alternatively, targeting may occur through binding of a plasma receptor that later passes through a late endosome; the therapeutic agent can then travel from the late endosome to a lysosome. A preferred lysosomal targeting mechanism involves binding to the cation-independent M6P receptor.

Cation-Independent M6P Receptor

The cation-independent M6P receptor is a 275 kDa single chain transmembrane glycoprotein expressed ubiquitously in mammalian tissues. It is one of two mammalian receptors that bind M6P: the second is referred to as the cation-dependent M6P receptor. The cation-dependent M6P receptor requires divalent cations for M6P binding; the cation-independent M6P receptor does not. These receptors play an important role in the trafficking of lysosomal enzymes through recognition of the M6P moiety on high mannose carbohydrate on lysosomal enzymes. The extracellular domain of the cation-independent M6P receptor contains 15 homologous domains ("repeats") that bind a diverse group of ligands at discrete locations on the receptor.

The cation-independent M6P receptor contains two binding sites for M6P: one located in repeats 1-3 and the other located in repeats 7-9. The receptor binds monovalent M6P ligands with a dissociation constant in the µM range while binding divalent M6P ligands with a dissociation constant in the nM range, probably due to receptor oligomerization. Uptake of IGF-II by the receptor is enhanced by concomitant binding of multivalent M6P ligands such as lysosomal enzymes to the receptor.

The cation-independent M6P receptor also contains binding sites for at least three distinct ligands that can be used as targeting moieties. The cation-independent M6P receptor binds IGF-II with a dissociation constant of about 14 nM at or about pH 7.4, primarily through interactions with repeat 11. Consistent with its function in targeting IGF-II to the lysosome, the dissociation constant is increased approximately 100-fold at or about pH 5.5 promoting dissociation of IGF-II in acidic late endosomes. The receptor is capable of binding high molecular weight O-glycosylated IGF-II forms.

An additional useful ligand for the cation-independent M6P receptor is retinoic acid. Retinoic acid binds to the receptor with a dissociation constant of 2.5 nM. Affinity photolabeling of the cation-independent M6P receptor with retinoic acid does not interfere with IGF-II or M6P binding to the receptor, indicating that retinoic acid binds to a distinct site on the receptor. Binding of retinoic acid to the receptor alters the intracellular distribution of the receptor with a greater accumulation of the receptor in cytoplasmic vesicles and also enhances uptake of M6P modified β-glucuronidase. Retinoic acid has a photoactivatable moiety that can be used to link it to a therapeutic agent without interfering with its ability to bind to the cation-independent M6P receptor.

The cation-independent M6P receptor also binds the urokinase-type plasminogen receptor (uPAR) with a dissociation constant of 9 µM. uPAR is a GPI-anchored receptor on the surface of most cell types where it functions as an adhesion molecule and in the proteolytic activation of plasminogen and TGF-β. Binding of uPAR to the CI-M6P receptor targets it to the lysosome, thereby modulating its activity. Thus, fusing the extracellular domain of uPAR, or a portion thereof competent to bind the cation-independent M6P receptor, to a therapeutic agent permits targeting of the agent to a lysosome.

IGF-II

In a preferred embodiment, the lysosomal targeting portion is a protein, peptide, or other moiety that binds the cation independent M6P/IGF-II receptor in a mannose-6-phosphate-independent manner. Advantageously, this embodiment mimics the normal biological mechanism for uptake of LSD proteins, yet does so in a manner independent of mannose-6-phosphate.

For example, by fusing DNA encoding the mature IGF-II polypeptide to the 3' end of LSD gene cassettes, fusion proteins are created that can be taken up by a variety of cell types and transported to the lysosome. Alternatively, DNA encoding a precursor IGF-II polypeptide can be fused to the 3' end of an LSD gene cassette; the precursor includes a carboxy-terminal portion that is cleaved in mammalian cells to yield the mature IGF-II polypeptide, but the IGF-II signal peptide is preferably omitted (or moved to the 5' end of the LSD gene cassette). This method has numerous advantages over methods involving glycosylation including simplicity and cost effectiveness, because once the protein is isolated, no further modifications need be made.

IGF-II is preferably targeted specifically to the M6P receptor. Particularly useful are mutations in the IGF-II polypeptide that result in a protein that binds the M6P receptor with high affinity while no longer binding the other two receptors with appreciable affinity. IGF-II can also be modified to minimize binding to serum IGF-binding proteins (Baxter (2000) *Am. J. Physiol Endocrinol Metab.* 278(6):967-76) to avoid sequestration of IGF-II/GILT constructs. A number of studies have localized residues in IGF-1 and IGF-II necessary for binding to IGF-binding proteins. Constructs with mutations at these residues can be screened for retention of high affinity binding to the M6P/IGF-II receptor and for reduced affinity for IGF-binding proteins. For example, replacing PHE 26 of IGF-II with SER is reported to reduce affinity of IGF-II for IGFBP-1 and -6 with no effect on binding to the M6P/IGF-II receptor (Bach et al. (1993) *J. Biol. Chem.* 268(13):9246-54). Other substitutions, such as SER for PHE 19 and LYS for GLU 9, can also be advantageous. The analogous mutations, separately or in combination, in a region of IGF-I that is highly conserved with IGF-II result in large decreases in IGF-BP binding (Magee et al. (1999) *Biochemistry* 38(48): 15863-70).

An alternate approach is to identify minimal regions of IGF-II that can bind with high affinity to the M6P/IGF-II receptor. The residues that have been implicated in IGF-II binding to the M6P/IGF-II receptor mostly cluster on one face of IGF-II (Terasawa et al. (1994) *EMBO J.* 13(23):5590-7). Although IGF-II tertiary structure is normally maintained by three intramolecular disulfide bonds, a peptide incorporating the amino acid sequence on the M6P/IGF-II receptor binding surface of IGF-II can be designed to fold properly and have binding activity. Such a minimal binding peptide is a highly preferred targeting portion. Designed peptides based on the region around amino acids 48-55 can be tested for binding to the M6P/IGF-II receptor. Alternatively, a random library of peptides can be screened for the ability to bind the M6P/IGF-II receptor either via a yeast two hybrid assay, or via a phage display type assay.

Blood Brain Barrier

One challenge in therapy for lysosomal storage diseases is that many of these diseases have significant neurological involvement. Therapeutic enzymes administered into the blood stream generally do not cross the blood brain barrier and therefore cannot relieve neurological symptoms associated with the diseases. IGF-II, however, has been reported to promote transport across the blood brain barrier via transcytosis (Bickel et al. (2001) *Adv. Drug Deliv. Rev.* 46(1-3):247-79). Thus, appropriately designed GILT constructs should be capable of crossing the blood brain barrier, affording for the first time a means of treating neurological symptoms associated with lysosomal storage diseases. The constructs can be tested using GUS minus mice as described in Example 12. Further details regarding design, construction and testing of targeted therapeutics that can reach neuronal tissue from blood are disclosed in U.S. Ser. No. 60/329,650, filed Oct. 16, 2001, and in U.S. Ser. No. 10/136,639, filed Apr. 30, 2002.

Structure of IGF-II

NMR structures of IGF-II have been solved by two groups (Terasawa et al. (1994) *EMBO J.* 13(23):5590-7; Torres et al. (1995) *J. Mol. Biol.* 248(2):385-401) (see, e.g., Protein Data Bank record 1IGL). The general features of the IGF-II structure are similar to IGF-I and insulin. The A and B domains of IGF-II correspond to the A and B chains of insulin. Secondary structural features include an alpha helix from residues 11-21 of the B region connected by a reverse turn in residues 22-25 to a short beta strand in residues 26-28. Residues 25-27 appear to form a small antiparallel beta sheet; residues 59-61 and residues 26-28 may also participate in intermolecular beta-sheet formation. In the A domain of IGF-II, alpha helices spanning residues 42-49 and 53-59 are arranged in an antiparallel configuration perpendicular to the B-domain helix. Hydrophobic clusters formed by two of the three disulfide bridges and conserved hydrophobic residues stabilize these secondary structure features. The N and C termini remain poorly defined as is the region between residues 31-40.

IGF-II binds to the IGF-II/M6P and IGF-I receptors with relatively high affinity and binds with lower affinity to the insulin receptor. IGF-II also interacts with a number if serum IGFBPs.

Binding to the IGF-II/M6P Receptor

Substitution of IGF-II residues 48-50 (Phe Arg Ser) with the corresponding residues from insulin, (Thr Ser Ile), or substitution of residues 54-55 (Ala Leu) with the corresponding residues from IGF-I (Arg Arg) result in diminished binding to the IGF-II/M6P receptor but retention of binding to the IGF-I and insulin receptors (Sakano et al. (1991) *J. Biol. Chem.* 266(31):20626-35).

IGF-I and IGF-II share identical sequences and structures in the region of residues 48-50 yet have a 1000-fold difference in affinity for the IGF-II receptor. The NMR structure reveals a structural difference between IGF-I and IGF-II in the region of IGF-II residues 53-58 (IGF-I residues 54-59): the alpha-helix is better defined in IGF-II than in IGF-I and, unlike IGF-I, there is no bend in the backbone around residues 53 and 54 (Torres et al. (1995) *J. Mol. Biol.* 248(2):385-401). This structural difference correlates with the substitution of Ala 54 and Leu 55 in IGF-II with Arg 55 and Arg 56 in IGF-I. It is possible either that binding to the IGF-II receptor is disrupted directly by the presence of charged residues in this region or that changes in the structure engendered by the charged residues yield the changes in binding for the IGF-II receptor. In any case, substitution of uncharged residues for the two Arg residues in IGF-I resulted in higher affinities for the IGF-II receptor (Cacciari et al. (1987) *Pediatrician* 14(3): 146-53). Thus the presence of positively charged residues in these positions correlates with loss of binding to the IGF-II receptor.

IGF-II binds to repeat 11 of the cation-independent M6P receptor. Indeed, a minireceptor in which only repeat 11 is fused to the transmembrane and cytoplasmic domains of the cation-independent M6P receptor is capable of binding IGF-II (with an affinity approximately one tenth the affinity of the full length receptor) and mediating internalization of IGF-II and its delivery to lysosomes (Grimme et al. (2000) *J. Biol. Chem.* 275(43):33697-33703). The structure of domain 11 of the M6P receptor is known (Protein Data Base entries 1GP0 and 1 GP3; Brown et al. (2002) *EMBO J.* 21(5):1054-1062). The putative IGF-II binding site is a hydrophobic pocket believed to interact with hydrophobic amino acids of IGF-II; candidate amino acids of IGF-II include leucine 8, phenylalanine 48, alanine 54, and leucine 55. Although repeat 11 is sufficient for IGF-II binding, constructs including larger portions of the cation-independent M6P receptor (e.g. repeats 10-13, or 1-15) generally bind IGF-II with greater affinity and with increased pH dependence (see, for example, Linnell et al. (2001) *J. Biol. Chem.* 276(26):23986-23991).

Binding to the IGF-I Receptor

Substitution of IGF-II residues Tyr 27 with Leu, Leu 43 with Val or Ser 26 with Phe diminishes the affinity of IGF-II for the IGF-I receptor by 94-, 56-, and 4-fold respectively (Torres et al. (1995) *J. Mol. Biol.* 248(2):385-401). Deletion of residues 1-7 of human IGF-II resulted in a 30-fold decrease in affinity for the human IGF-I receptor and a concomitant 12 fold increase in affinity for the rat IGF-II receptor (Hashimoto et al. (1995) *J. Biol. Chem.* 270(30):18013-8). The NMR structure of IGF-II shows that Thr 7 is located near residues 48 Phe and 50 Ser as well as near the 9 Cys-47 Cys disulfide bridge. It is thought that interaction of Thr 7 with these residues can stabilize the flexible N-terminal hexapeptide required for IGF-I receptor binding (Terasawa et al. (1994) *EMBO J.* 13(23)5590-7). At the same time this interaction can modulate binding to the IGF-II receptor. Truncation of the C-terminus of IGF-II (residues 62-67) also appear to lower the affinity of IGF-II for the IGF-I receptor by 5 fold (Roth et al. (1991) *Biochem. Biophys. Res. Commun.* 181(2):907-14).

Deletion Mutants of IGF-II

The binding surfaces for the IGF-I and cation-independent M6P receptors are on separate faces of IGF-II. Based on structural and mutational data, functional cation-independent M6P binding domains can be constructed that are substantially smaller than human IGF-II. For example, the amino terminal amino acids 1-7 and/or the carboxy terminal residues 62-67 can be deleted or replaced. Additionally, amino acids 29-40 can likely be eliminated or replaced without altering the folding of the remainder of the polypeptide or binding to the cation-independent M6P receptor. Thus, a targeting moiety including amino acids 8-28 and 41-61 can be constructed. These stretches of amino acids could perhaps be joined directly or separated by a linker. Alternatively, amino acids 8-28 and 41-61 can be provided on separate polypeptide chains. Comparable domains of insulin, which is homologous to IGF-II and has a tertiary structure closely related to the structure of IGF-II, have sufficient structural information to permit proper refolding into the appropriate tertiary structure, even when present in separate polypeptide chains (Wang et al. (1991) *Trends Biochem. Sci.* 279-281). Thus, for example, amino acids 8-28, or a conservative substitution variant thereof, could be fused to a therapeutic agent; the resulting fusion protein could be admixed with amino acids 41-61, or a conservative substitution variant thereof, and administered to a patient.

Binding to IGF Binding Proteins

IGF-II and related constructs can be modified to diminish their affinity for IGFBPs, thereby increasing the bioavailability of the tagged proteins.

Substitution of IGF-II residue phenylalanine 26 with serine reduces binding to IGFBPs 1-5 by 5-75 fold (Bach et al. (1993) *J. Biol. Chem.* 268(13):9246-54). Replacement of IGF-II residues 48-50 with threonine-serine-isoleucine reduces binding by more than 100 fold to most of the IGFBPs (Bach et al. (1993) *J. Biol. Chem.* 268(13):9246-54); these residues are, however, also important for binding to the cation-independent mannose-6-phosphate receptor. The Y27L substitution that disrupts binding to the IGF-I receptor interferes with formation of the ternary complex with IGFBP3 and acid labile subunit (Hashimoto et al. (1997) *J. Biol. Chem.* 272(44):27936-42); this ternary complex accounts for most of the IGF-II in the circulation (Yu et al. (1999) *J. Clin. Lab Anal.* 13(4):166-72). Deletion of the first six residues of IGF-II also interferes with IGFBP binding (Luthi et al. (1992) *Eur. J. Biochem.* 205(2):483-90).

Studies on IGF-I interaction with IGFBPs revealed additionally that substitution of serine for phenylalanine 16 did not effect secondary structure but decreased IGFBP binding by between 40 and 300 fold (Magee et al. (1999) *Biochemistry* 38(48):15863-70). Changing glutamate 9 to lysine also resulted in a significant decrease in IGFBP binding. Furthermore, the double mutant lysine 9/serine 16 exhibited the lowest affinity for IGFBPs. Although these mutations have not previously been tested in IGF-II, the conservation of sequence between this region of IGF-I and IGF-II suggests that a similar effect will be observed when the analogous mutations are made in IGF-II (glutamate 12 lysine/phenylalanine 19 serine).

IGF-II Homolops

The amino acid sequence of human IGF-II, or a portion thereof affecting binding to the cation-independent M6P receptor, may be used as a reference sequence to determine whether a candidate sequence possesses sufficient amino acid similarity to have a reasonable expectation of success in the methods of the present invention. Preferably, variant sequences are at least 70% similar or 60% identical, more preferably at least 75% similar or 65% identical, and most preferably 80% similar or 70% identical to human IGF-II.

To determine whether a candidate peptide region has the requisite percentage similarity or identity to human IGF-II, the candidate amino acid sequence and human IGF-II are first aligned using the dynamic programming algorithm described in Smith and Waterman (1981) *J. Mol. Biol.* 147:195-197, in combination with the BLOSUM62 substitution matrix described in FIG. 2 of Henikoff and Henikoff (1992) *PNAS* 89:10915-10919. For the present invention, an appropriate value for the gap insertion penalty is −12, and an appropriate value for the gap extension penalty is −4. Computer programs performing alignments using the algorithm of Smith-Waterman and the BLOSUM62 matrix, such as the GCG program suite (Oxford Molecular Group, Oxford, England), are commercially available and widely used by those skilled in the art.

Once the alignment between the candidate and reference sequence is made, a percent similarity score may be calculated. The individual amino acids of each sequence are compared sequentially according to their similarity to each other. If the value in the BLOSUM62 matrix corresponding to the two aligned amino acids is zero or a negative number, the pairwise similarity score is zero; otherwise the pairwise similarity score is 1.0. The raw similarity score is the sum of the pairwise similarity scores of the aligned amino acids. The raw score is then normalized by dividing it by the number of amino acids in the smaller of the candidate or reference sequences. The normalized raw score is the percent similarity. Alternatively, to calculate a percent identity, the aligned amino acids of each sequence are again compared sequentially. If the amino acids are non-identical, the pairwise identity score is zero; otherwise the pairwise identity score is 1.0. The raw identity score is the sum of the identical aligned amino acids. The raw score is then normalized by dividing it by the number of amino acids in the smaller of the candidate or reference sequences. The normalized raw score is the percent identity. Insertions and deletions are ignored for the purposes of calculating percent similarity and identity. Accordingly, gap penalties are not used in this calculation, although they are used in the initial alignment.

IGF-II Structural Analogs

The known structures of human IGF-II and the cation-independent M6P receptors permit the design of IGF-II analogs and other cation-independent M6P receptor binding proteins using computer-assisted design principles such as those discussed in U.S. Pat. Nos. 6,226,603 and 6,273,598. For example, the known atomic coordinates of IGF-II can be provided to a computer equipped with a conventional computer modeling program, such as INSIGHTII, DISCOVER, or DELPHI, commercially available from Biosym, Technologies Inc., or QUANTA, or CHARMM, commercially available from Molecular Simulations, Inc. These and other software programs allow analysis of molecular structures and simulations that predict the effect of molecular changes on structure and on intermolecular interactions. For example, the software can be used to identify modified analogs with the ability to form additional intermolecular hydrogen or ionic bonds, improving the affinity of the analog for the target receptor.

The software also permits the design of peptides and organic molecules with structural and chemical features that mimic the same features displayed on at least part of the surface of the cation-independent M6P receptor binding face of IGF-II. Because a major contribution to the receptor binding surface is the spatial arrangement of chemically interactive moieties present within the sidechains of amino acids which together define the receptor binding surface, a preferred embodiment of the present invention relates to designing and producing a synthetic organic molecule having a framework that carries chemically interactive moieties in a spatial relationship that mimics the spatial relationship of the chemical moieties disposed on the amino acid sidechains which constitute the cation-independent M6P receptor binding face of IGF-II. Preferred chemical moieties, include but are not limited to, the chemical moieties defined by the amino acid side chains of amino acids constituting the cation-independent M6P receptor binding face of IGF-II. It is understood, therefore, that the receptor binding surface of the IGF-II analog need not comprise amino acid residues but the chemical moieties disposed thereon.

For example, upon identification of relevant chemical groups, the skilled artisan using a conventional computer program can design a small molecule having the receptor interactive chemical moieties disposed upon a suitable carrier framework. Useful computer programs are described in, for example, Dixon (1992) Tibtech 10: 357-363; Tschinke et al. (1993) J. Med. Chem 36: 3863-3870; and Eisen et al. (1994) Proteins: Structure, Function, and Genetics 19: 199-221, the disclosures of which are incorporated herein by reference.

One particular computer program entitled "CAVEAT" searches a database, for example, the Cambridge Structural Database, for structures which have desired spatial orientations of chemical moieties (Bartlett et al. (1989) in "Molecular Recognition: Chemical and Biological Problems" (Roberts, S. M., ed) pp 182-196). The CAVEAT program has been used to design analogs of tendamistat, a 74 residue inhibitor of α-amylase, based on the orientation of selected amino acid side chains in the three-dimensional structure of tendamistat (Bartlett et al. (1989) supra).

Alternatively, upon identification of a series of analogs which mimic the cation-independent M6P receptor binding activity of IGF-II, the skilled artisan may use a variety of computer programs which assist the skilled artisan to develop quantitative structure activity relationships (QSAR) and further to assist in the de novo design of additional morphogen analogs. Other useful computer programs are described in, for example, Connolly-Martin (1991) Methods in Enzymology 203:587-613; Dixon (1992) supra; and Waszkowycz et al. (1994) J. Med. Chenm. 37: 3994-4002.

Targeting Moiety Affinities

Preferred targeting moieties bind to their target receptors with a submicromolar dissociation constant. Generally speaking, lower dissociation constants (e.g. less than $10^{-7}$ M, less than $10^{-8}$ M, or less than $10^{-9}$ M) are increasingly preferred. Determination of dissociation constants is preferably determined by surface plasmon resonance as described in Linnell et al. (2001) *J. Biol. Chem.* 276(26):23986-23991. A soluble form of the extracellular domain of the target receptor (e.g. repeats 1-15 of the cation-independent M6P receptor) is generated and immobilized to a chip through an avidin-biotin interaction. The targeting moiety is passed over the chip, and kinetic and equilibrium constants are detected and calculated by measuring changes in mass associated with the chip surface.

Nucleic Acids and Expression Systems

Chimeric fusion proteins can be expressed in a variety of expression systems, including in vitro translation systems and intact cells. Since M6P modification is not a prerequisite for targeting, a variety of expression systems including yeast, baculovirus and even prokaryotic systems such as *E. coli* that do not glycosylate proteins are suitable for expression of targeted therapeutic proteins. In fact, an unglycosylated protein generally has improved bioavailability, since glycosylated proteins are rapidly cleared from the circulation through binding to the mannose receptor in hepatic sinusoidal endothelium.

Alternatively, production of chimeric targeted lysosomal enzymes in mammalian cell expression system produces proteins with multiple binding determinants for the cation-independent M6P receptor. Synergies between two or more cation-independent M6P receptor ligands (e.g. M6P and IGF-II, or M6P and retinoic acid) can be exploited: multivalent ligands have been demonstrated to enhance binding to the receptor by receptor crosslinking.

In general, gene cassettes encoding the chimeric therapeutic protein can be tailored for the particular expression system to incorporate necessary sequences for optimal expression including promoters, ribosomal binding sites, introns, or alterations in coding sequence to optimize codon usage. Because the protein is preferably secreted from the producing cell, a DNA encoding a signal peptide compatible with the expression system can be substituted for the endogenous signal peptide. For example, for expression of β-glucuronidase and α-galactosidase A tagged with IGF-II in *Leishmania*, DNA cassettes encoding *Leishmania* signal peptides (GP63 or SAP) are inserted in place of the DNA encoding the endogenous signal peptide to achieve optimal expression. In mammalian expression systems the endogenous signal peptide may be employed but if the IGF-II tag is fused at the 5' end of the coding sequence, it could be desirable to use the IGF-II signal peptide.

CHO cells are a preferred mammalian host for the production of therapeutic proteins. The classic method for achieving high yield expression from CHO cells is to use a CHO cell line deficient in dihydrofolate reductase (DHFR), for example CHO line DUKX (O'Dell et al. (1998) *Int. J. Biochem. Cell Biol.* 30(7):767-71). This strain of CHO cells requires hypoxanthine and thymidine for growth. Co-transfection of the gene to be overexpressed with a DHFR gene cassette, on separate plasmids or on a single plasmid, permits selection for the DHFR gene and generally allows isolation of clones that also express the recombinant protein of choice. For example, plasmid pcDNA3 uses the cytomegalovirus (CMV) early region regulatory region promoter to drive expression of a gene of interest and pSV2DHFR to promote DHFR expression. Subsequent exposure of cells harboring the recombinant gene cassettes to incrementally increasing concentrations of the folate analog methotrexate leads to amplification of both the gene copy number of the DHFR gene and of the co-transfected gene.

A preferred plasmid for eukaryotic expression in this system contains the gene of interest placed downstream of a strong promoter such as CMV. An intron can be placed in the 3' flank of the gene cassette. A DHFR cassette can be driven by a second promoter from the same plasmid or from a separate plasmid. Additionally, it can be useful to incorporate into the plasmid an additional selectable marker such as neomycin phosphotransferase, which confers resistance to G418.

Another CHO expression system (Ulmasov et al. (2000) *PNAS* 97(26):14212-14217) relies on amplification of the gene of interest using G418 instead of the DHFR/methotrexate system described above. A pCXN vector with a slightly defective neomycin phosphotransferase driven by a weak promoter (see, e.g., Niwa et al. (1991) *Gene* 108:193-200) permits selection for transfectants with a high copy number (>300) in a single step.

Alternatively, recombinant protein can be produced in the human HEK 293 cell line using expression systems based on the Epstein-Barr Virus (EBV) replication system. This consists of the EBV replication origin oriP and the EBV ori binding protein, EBNA-1. Binding of EBNA-1 to oriP initiates replication and subsequent amplification of the extrachromosomal plasmid. This amplification in turn results in high levels of expression of gene cassettes housed within the plasmid. Plasmids containing oriP can be transfected into EBNA-1 transformed HEK 293 cells (commercially available from Invitrogen) or, alternatively, a plasmid such as pCEP4 (commercially available from Invitrogen) which drives expression of EBNA-1 and contains the EBV oriP can be employed.

In *E. coli*, the therapeutic proteins are preferably secreted into the periplasmic space. This can be achieved by substituting for the DNA encoding the endogenous signal peptide of the LSD protein a nucleic acid cassette encoding a bacterial signal peptide such as the ompA signal sequence. Expression can be driven by any of a number of strong inducible promoters such as the lac, trp, or tac promoters. One suitable vector is pBAD/gIII (commercially available from Invitrogen) which uses the Gene III signal peptide and the araBAD promoter.

In Vitro Refolding

One useful IGF-II targeting portion has three intramolecular disulfide bonds. GILT fusion proteins (for example GUS-GILT) in *E. coli* can be constructed that direct the protein to the periplasmic space. IGF-II, when fused to the C-terminus of another protein, can be secreted in an active form in the periplasm of *E. coli* (Wadensten et al. (1991) *Biotechnol. Appl. Biochem.* 13(3):412-21). To facilitate optimal folding of the IGF-II moiety, appropriate concentrations of reduced and oxidized glutathione are preferably added to the cellular milieu to promote disulfide bond formation. In the event that a fusion protein with disulfide bonds is incompletely soluble, any insoluble material is preferably treated with a chaotropic agent such as urea to solubilize denatured protein and refolded in a buffer having appropriate concentrations of reduced and oxidized glutathione, or other oxidizing and reducing agents, to facilitate formation of appropriate disulfide bonds (Smith et al. (1989) *J. Biol. Chem.* 264(16):9314-21). For example, IGF-I has been refolded using 6 M guanidine-HCl and 0.1 M tris(2-carboxyethyl)phosphine reducing agent for denaturation and reduction of IGF-II (Yang et al. (1999) *J. Biol. Chem.* 274(53):37598-604). Refolding of proteins was accomplished in 0.1 M Tris-HCl buffer (pH8.7) containing 1 mM oxidized glutathione, 10 mM reduced glutathione, 0.2M KCl and 1 mM EDTA.

Underglycosylation

Targeted therapeutic proteins are preferably underglycosylated: one or more carbohydrate structures that would normally be present if the protein were produced in a mammalian cell is preferably omitted, removed, modified, or masked, extending the half-life of the protein in a mammal. Underglycosylation can be achieved in many ways, several of which are diagrammed in FIG. 1. As shown in FIG. 1, a protein may be actually underglycosylated, actually lacking one or more of the carbohydrate structures, or functionally underglycosylated through modification or masking of one or more of the carbohydrate structures. A protein may be actually underglycosylated when synthesized, as discussed in Example 14, and may be completely unglycosylated (as when synthesized in *E. coli*), partially unglycosylated (as when synthesized in a mammalian system after disruption of one or more glycosylation sites by site-directed mutagenesis), or may have a non-mammalian glycosylation pattern. Actual underglycosylation can also be achieved by deglycosylation of a protein after synthesis. As discussed in Example 14, deglycosylation can be through chemical or enzymatic treatments, and may lead to complete deglycosylation or, if only a portion of the carbohydrate structure is removed, partial deglycosylation.

In Vivo Expression

A nucleic acid encoding a therapeutic protein, preferably a secreted therapeutic protein, can be advantageously provided directly to a patient suffering from a disease, or may be provided to a cell ex vivo, followed by administration of the living cell to the patient. In vivo gene therapy methods known in the art include providing purified DNA (e.g. as in a plasmid), providing the DNA in a viral vector, or providing the DNA in a liposome or other vesicle (see, for example, U.S. Pat. No. 5,827,703, disclosing lipid carriers for use in gene therapy, and U.S. Pat. No. 6,281,010, providing adenoviral vectors useful in gene therapy).

Methods for treating disease by implanting a cell that has been modified to express a recombinant protein are also well known. See, for example, U.S. Pat. No. 5,399,346, disclosing methods for introducing a nucleic acid into a primary human cell for introduction into a human. Although use of human cells for ex vivo therapy is preferred in some embodiments, other cells such as bacterial cells may be implanted in a patient's vasculature, continuously releasing a therapeutic agent. See, for example, U.S. Pat. Nos. 4,309,776 and 5,704,910.

Methods of the invention are particularly useful for targeting a protein directly to a subcellular compartment without requiring a purification step. In one embodiment, an IGF-II fusion protein is expressed in a symbiotic or attenuated parasitic organism that is administered to a host. The expressed IGF-II fusion protein is secreted by the organism, taken up by host cells and targeted to their lysosomes.

In some embodiments of the invention, GILT proteins are delivered in situ via live *Leishmania* secreting the proteins into the lysosomes of infected macrophage. From this organelle, it leaves the cell and is taken up by adjacent cells not of the macrophage lineage. Thus, the GILT tag and the therapeutic agent necessarily remain intact while the protein resides in the macrophage lysosome. Accordingly, when GILT proteins are expressed in situ, they are preferably modified to ensure compatibility with the lysosomal environment. Human β-glucuronidase (human "GUS"), an exemplary therapeutic portion, normally undergoes a C-terminal peptide cleavage either in the lysosome or during transport to the lysosome (e.g. between residues 633 and 634 in GUS). Thus, in embodiments where a GUS-GILT construct is to be expressed by *Leishmania* in a macrophage lysosome human GUS is preferably modified to render the protein resistant to cleavage, or the residues following residue 633 are preferably simply omitted from a GILT fusion protein. Similarly, IGF-II, an exemplary targeting portion, is preferably modified to increase its resistance to proteolysis, or a minimal binding peptide (e.g. as identified by phage display or yeast two hybrid) is substituted for the wildtype IGF-II moiety.

Administration

The targeted therapeutics produced according to the present invention can be administered to a mammalian host by any route. Thus, as appropriate, administration can be oral or parenteral, including intravenous and intraperitoneal routes of administration. In addition, administration can be by periodic injections of a bolus of the therapeutic or can be made more continuous by intravenous or intraperitoneal administration from a reservoir which is external (e.g., an i.v. bag). In certain embodiments, the therapeutics of the instant invention can be pharmaceutical-grade. That is, certain embodiments comply with standards of purity and quality control required for administration to humans. Veterinary applications are also within the intended meaning as used herein.

The formulations, both for veterinary and for human medical use, of the therapeutics according to the present invention typically include such therapeutics in association with a pharmaceutically acceptable carrier therefor and optionally other ingredient(s). The carrier(s) can be "acceptable" in the sense of being compatible with the other ingredients of the formulations and not deleterious to the recipient thereof. Pharmaceutically acceptable carriers, in this regard, are intended to include any and all solvents, dispersion media, coatings, antibacterial and antifungal agents, isotonic and absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified according to the invention and/or known in the art) also can be incorporated into the compositions. The formulations can conveniently be presented in dosage unit form and can be prepared by any of the methods well known in the art of pharmacy/microbiology. In general, some formulations are prepared by bringing the therapeutic into association with a liquid carrier or a finely divided solid carrier or both, and then, if necessary, shaping the product into the desired formulation.

A pharmaceutical composition of the invention is formulated to be compatible with its intended route of administration. Examples of routes of administration include oral or parenteral, e.g., intravenous, intradermal, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. Ph can be adjusted with acids or bases, such as hydrochloric acid or sodium hydroxide.

Useful solutions for oral or parenteral administration can be prepared by any of the methods well known in the pharmaceutical art, described, for example, in Remington's Pharmaceutical Sciences, (Gennaro, A., ed.), Mack Pub., 1990. Formulations for parenteral administration also can include glycocholate for buccal administration, methoxysalicylate for rectal administration, or cutric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions that are solid at room temperature and liquid at body temperatures. Formulations also can include, for example, polyalkylene glycols such as polyethylene glycol, oils of vegetable origin, hydrogenated naphthalenes, and the like. Formulations for direct administration can include glycerol and other compositions of high viscosity. Other potentially useful parenteral carriers for these therapeutics include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present invention suitable for oral administration can be in the form of discrete units such as capsules, gelatin capsules, sachets, tablets, troches, or lozenges, each containing a predetermined amount of the drug; in the form of a powder or granules; in the form of a solution or a suspension in an aqueous liquid or non-aqueous liquid; or in the form of an oil-in-water emulsion or a water-in-oil emulsion. The therapeutic can also be administered in the form of a bolus, electuary or paste. A tablet can be made by compressing or moulding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Molded tablets can be made by molding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like clan contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition can be sterile and can be fluid to the extent that easy syringability exists. It can be stable under the conditions of manufacture and storage and can be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the therapeutic which can be in microcrystalline form, for example, in the form of an aqueous microcrystalline suspension. Liposomal formulations or biodegradable polymer systems can also be used to present the therapeutic for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pasts; or solutions or suspensions such as drops. Formulations for topical administration to the skin surface can be prepared by dispersing the therapeutic with a dermatologically acceptable carrier such as a lotion, cream, ointment or soap. In some embodiments, useful are carriers capable of forming a film or layer over the skin to localize application and inhibit removal. Where adhesion to a tissue surface is desired the composition can include the therapeutic dispersed in a fibrinogen-thrombin composition or other bioadhesive. The therapeutic then can be painted, sprayed or otherwise applied to the desired tissue surface. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, such as for asthma, inhalation of powder (self-propelling or spray formulations) dispensed with a spray can, a nebulizer, or an atomizer can be used. Such formulations can be in the form of a finely comminuted powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the therapeutics also can be delivered in the form of an aerosol spray from a pressured container or dispenser which contains a suitable propellant, e.g., a gas such as carbon dioxide, or a nebulizer. Nasal drops also can be used.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents, bile salts, and filsidic acid derivatives. Transmucosal administration can be accomplished through the use of nasal sprays or suppositories. For transdermal administration, the therapeutics typically are formulated into ointments, salves, gels, or creams as generally known in the art.

In one embodiment, the therapeutics are prepared with carriers that will protect against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials also can be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811. Microsomes and microparticles also can be used.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Generally, the therapeutics identified according to the invention can be formulated for parenteral or oral administration to humans or other mammals, for example, in therapeutically effective amounts, e.g., amounts which provide appropriate concentrations of the drug to target tissue for a time sufficient to induce the desired effect. Additionally, the therapeutics of the present invention can be administered alone or in combination with other molecules known to have a beneficial effect on the particular disease or indication of interest. By way of example only, useful cofactors include symptom-alleviating cofactors, including antiseptics, antibiotics, antiviral and antifungal agents and analgesics and anesthetics.

The effective concentration of the therapeutics identified according to the invention that is to be delivered in a therapeutic composition will vary depending upon a number of factors, including the final desired dosage of the drug to be administered and the route of administration. The preferred dosage to be administered also is likely to depend on such variables as the type and extent of disease or indication to be treated, the overall health status of the particular patient, the relative biological efficacy of the therapeutic delivered, the formulation of the therapeutic, the presence and types of excipients in the formulation, and the route of administration. In some embodiments, the therapeutics of this invention can be provided to an individual using typical dose units deduced from the earlier-described mammalian studies using non-human primates and rodents. As described above, a dosage unit refers to a unitary, i.e. a single dose which is capable of being administered to a patient, and which can be readily handled and packed, remaining as a physically and biologically stable unit dose comprising either the therapeutic as such or a mixture of it with solid or liquid pharmaceutical diluents or carriers.

In certain embodiments, organisms are engineered to produce the therapeutics identified according to the invention. These organisms can release the therapeutic for harvesting or can be introduced directly to a patient. In another series of embodiments, cells can be utilized to serve as a carrier of the therapeutics identified according to the invention.

Therapeutics of the invention also include the "prodrug" derivatives. The term prodrug refers to a pharmacologically inactive (or partially inactive) derivative of a parent molecule that requires biotransformation, either spontaneous or enzymatic, within the organism to release or activate the active component. Prodrugs are variations or derivatives of the therapeutics of the invention which have groups cleavable under metabolic conditions. Prodrugs become the therapeutics of the invention which are pharmaceutically active in vivo, when they undergo solvolysis under physiological conditions or undergo enzymatic degradation. Prodrug of this invention can be called single, double, triple, and so on, depending on the number of biotransformation steps required to release or activate the active drug component within the organism, and indicating the number of functionalities present in a precursor-type form. Prodrug forms often offer advantages of solubility, tissue compatibility, or delayed release in the mammalian organism (see, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif., 1992). Moreover, the prodrug derivatives according to this invention can be combined with other features to enhance bioavailability.

EXAMPLES

Example 1

GILT Constructs

IGF-II cassettes have been synthesized by ligation of a series of overlapping oligos and cloned into Pir1-SAT, a standard *Leishmania* expression vector. 4 IGF-II cassettes have been made: one that encodes the wildtype mature polypeptide, one with a Δ1-7 deletion, one with a Y27L mutation, and one with both mutations. These mutations are reported to reduce binding of IGF-II to the other receptors while not affecting binding to the M6P receptor.

Figure 2B:
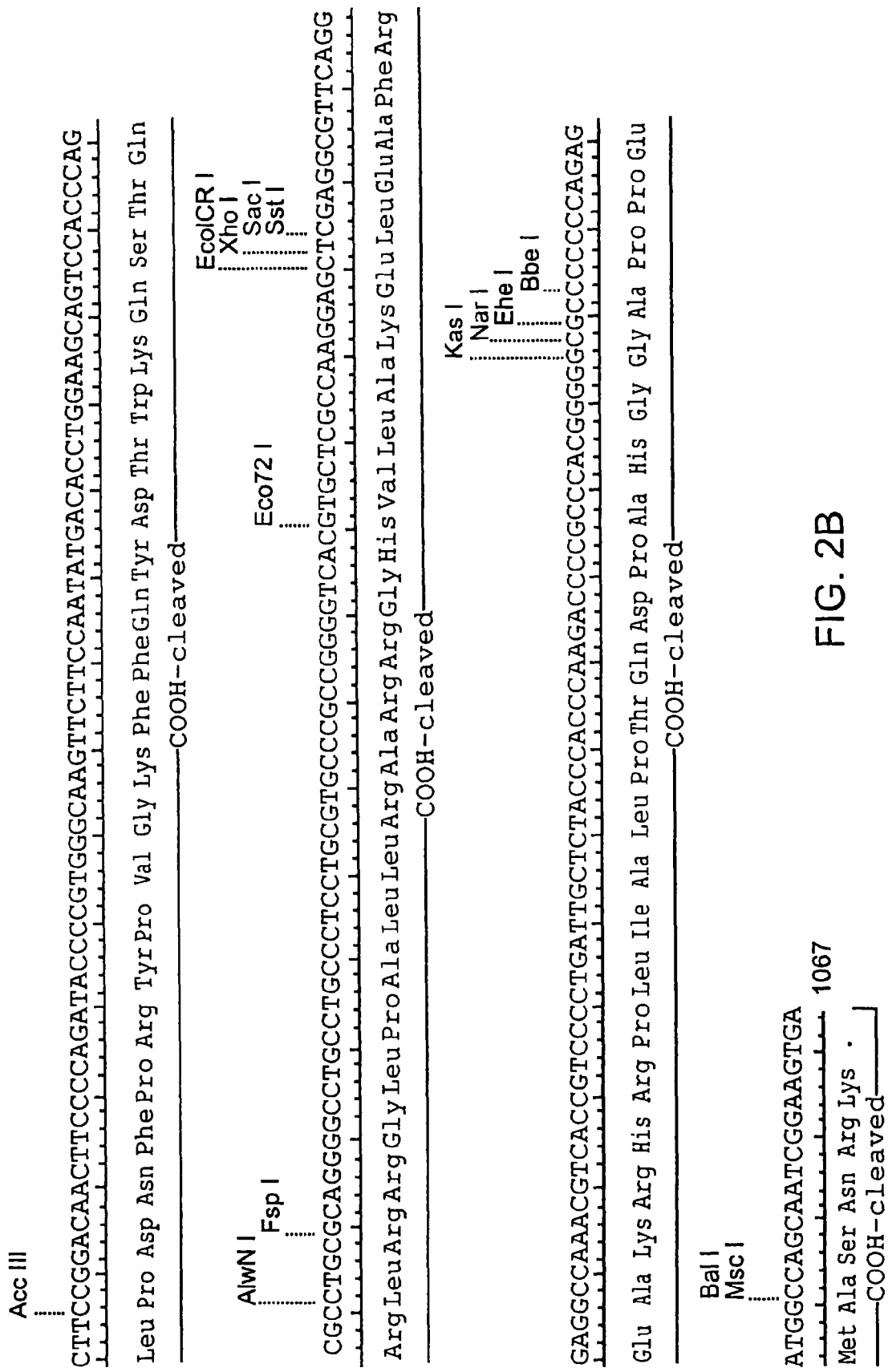
FIG. 2 is a map of the human IGF-II open reading frame (SEQ ID NO: 1) and its encoded protein (SEQ ID NO:2). Mature IGF-II lacks the signal peptide and COOH-cleaved regions.
Figure 3:
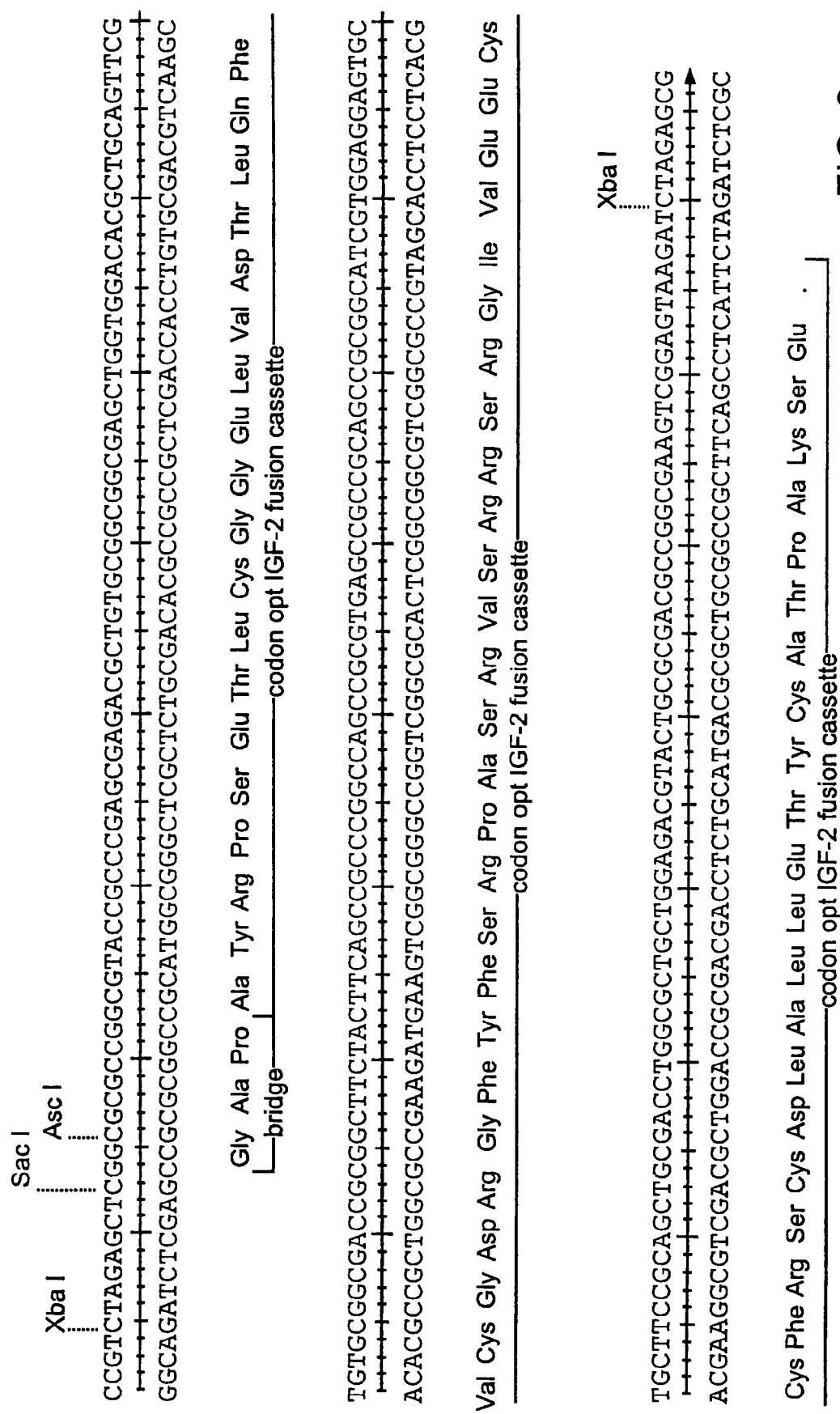
FIG. 3 is a *Leishmania* codon-optimized IGF-II depicted in the XbaI site of pIR1-SAT; the nucleic acid is SEQ ID NO:3 and the encoded protein is SEQ ID NO:4.
Figure 5:
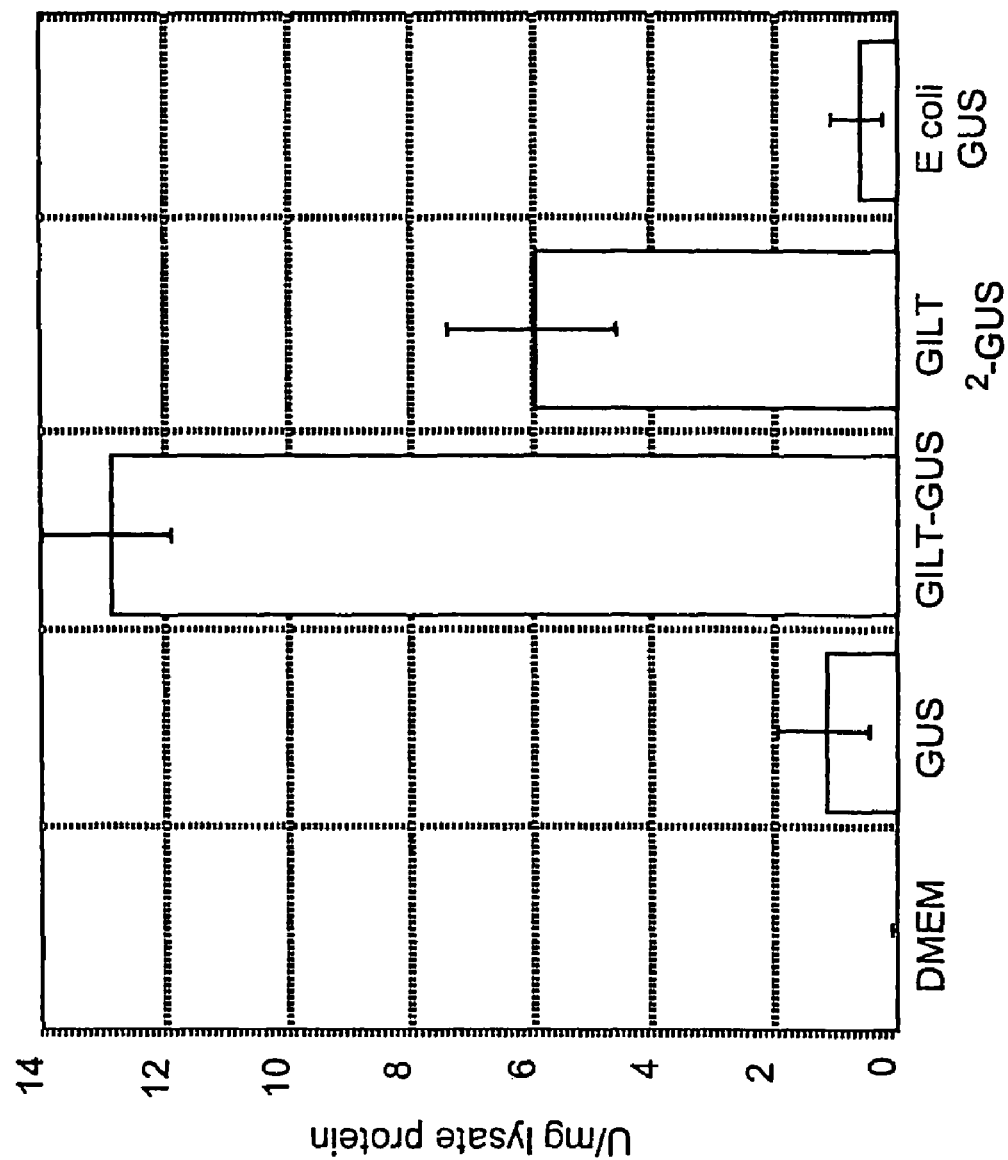
FIG. 5 depicts β-glucuronidase (GUS) activity in human mucopolysaccharidosis VII skin fibroblast GM4668 cells exposed to GUS, a GUS-IGF-II fusion protein (GILT-GUS), GILT-GUS with Δ1-7 and Y27L mutations in the IGF-II portion (GILT$^2$-GUS), or a negative control (DMEM).
Figure 6:
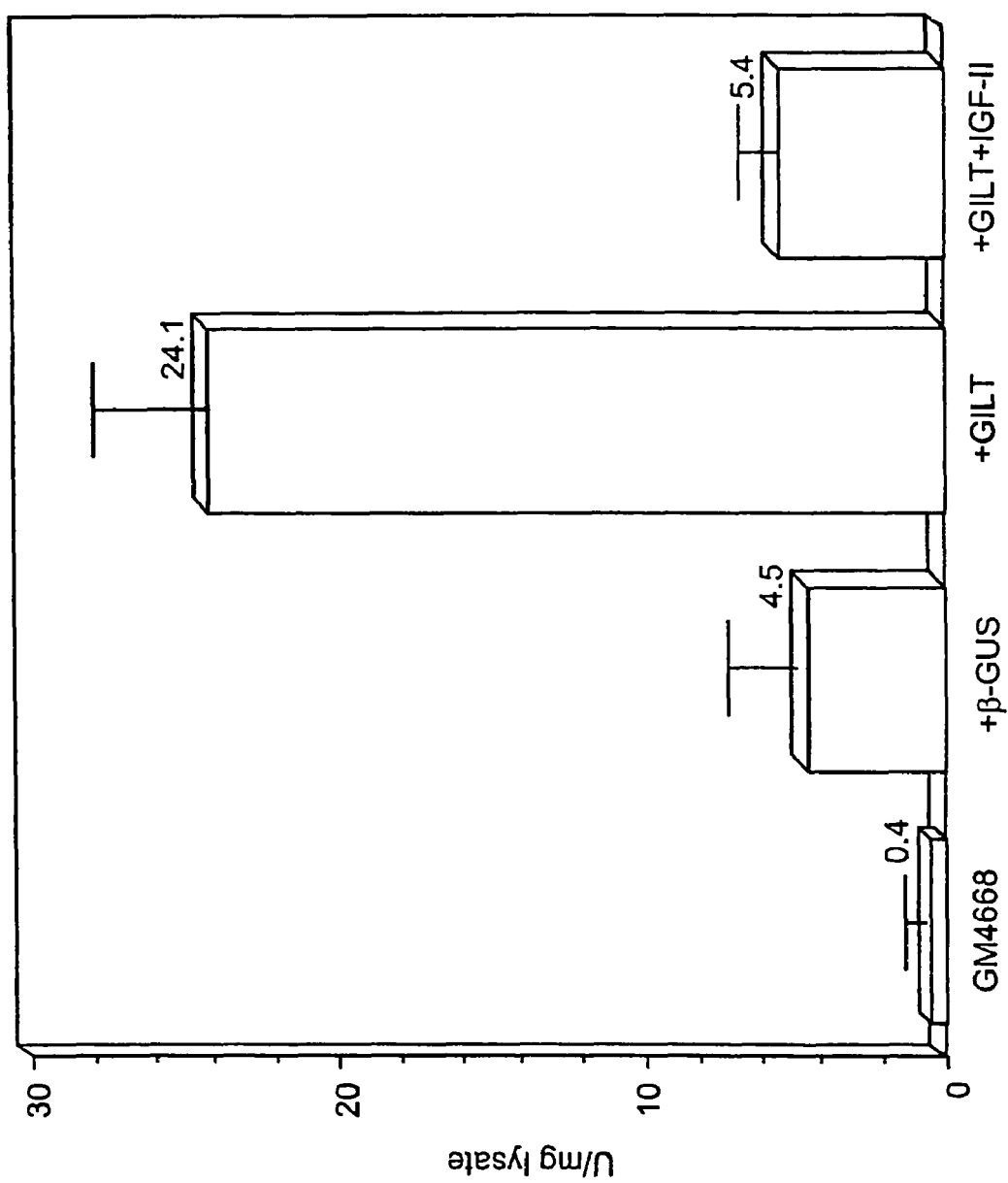
FIG. 6 depicts GUS activity in GM4668 cells exposed to GUS (+β-GUS), GUS-GILT (+GILT), GUS-GILT in the presence of excess IGF-II (+GILT+IGF-II), or a negative control (GM4668).

The coding sequence of human IGF-II is shown in FIG. 2. The protein is synthesized as a pre-pro-protein with a 24 amino acid signal peptide at the amino terminus and a 89 amino acid carboxy terminal region both of which are removed post-translationally, reviewed in (O'Dell et al. (1998) *Int. J. Biochem Cell Biol.* 30(7):767-71. The mature protein is 67 amino acids. A *Leishmania* codon optimized version of the mature IGF-II is shown in FIG. 3 (Langford et al. (1992) *Exp. Parasitol* 74(3):360-1). This cassette was constructed by annealing overlapping oligonucleotides whose sequences are shown in Table 3. Additional cassettes containing a deletion of amino acids 1-7 of the mature polypeptide (Δ1-7), alteration of residue 27 from tyrosine to leucine (Y27L) or both mutations (Δ1-7,Y27L) were made to produce IGF-II cassettes with specificity for only the desired receptor as described below. To make the wildtype IGF-II cassette, oligos GILT1-9 were annealed and ligated. To make the Y27L cassette, oligos 1, 12, 3, 4, 5, 16, 7, 8 and 9 were annealed and ligated. After ligation, the two cassettes were column purified. Wildtype and Y27L cassettes were amplified by PCR using oligos GILT 20 and 10 and the appropriate template. To incorporate the Δ1-7 deletion, the two templates were amplified using oligos GILT 11 and 10. The resulting 4 IGF-II cassettes (wildtype, Y27L, Δ1-7, and Y27LΔ1-7) were column purified, digested with XbaI, gel purified and ligated to XbaI cut Pir1-SAT.

Gene cassettes were then cloned between the XmaI site (not shown) upstream of XbaI in the vector and the AscI site in such a way as to preserve the reading frame. An overlapping DAM methylase site at the 3' XbaI site permitted use of the 5' XbaI site instead of the XmaI site for cloning. The AscI site adds a bridge of 3 amino acid residues.

TABLE 3

Oligonucleotides used in the construction of Pir-GILT vectors.

| NAME | SEQ ID NO: | SEQUENCE | POSITION |
|---|---|---|---|
| GILT 1 | 9 | GCGGCGGCGAGCTGGTGGACAC GCTGCAGTTCGTGTGCGGCGAC CGCGGC | 48-97 top strand |
| GILT 2 | 10 | TTCTACTTCAGCCGCCCGGCCA GCCGCGTGAGCCGCCGCAGCCG CGGCAT | 98-127 top strand |
| GILT 3 | 11 | CGTGGAGGAGTGCTGCTTCCGC AGCTGCGACCTGGCGCTGCTGG AGACGT | 148-197 top strand |
| GILT 4 | 12 | ACTGCGCGACGCCGGCGAAGTC GGAGTAAGATCTAGAGCG | 198-237 top strand |
| GILT 5 | 13 | AGCGTGTCCACCAGCTCGCCGC CGCACAGCGTCTCGCTCGGGCG GTACGC | 72-23 bottom |
| GILT 6 | 14 | GGCTGGCCGGGCGGCTGAAGTA GAAGCCGCGGTCGCCGCACACG AACTGC | 122-73 bottom |
| GILT 7 | 15 | GCTGCGGAAGCAGCACTCCTCC ACGATGCCGCGGCTGCGGCGGC TCACGC | 172-123 bottom |

TABLE 3-continued

Oligonucleotides used in the construction of Pir-GILT vectors.

| NAME | SEQ ID NO: | SEQUENCE | POSITION |
|---|---|---|---|
| GILT 8 | 16 | CTCCGACTTCGCCGGCGTCGCG CAGTACGTCTCCAGCAGCGCCA GGTCGCA | 223-173 bottom |
| GILT 9 | 17 | CCGTCTAGAGCTCGGCGCGCCG GCGTACCGCCCGAGCGAGACGC TGT | 1-47 top strand |
| GILT 10 | 18 | CGCTCTAGATCTTACTCCGACT TCG | 237-202 bottom |
| GILT 11 | 19 | CCGTCTAGAGCTCGGCGCGCCG CTGTGCGGCGGCGAGCTGGTGG AC | 1-67, Δ23-43 top |
| GILT 12 | 20 | TTCCTGTTCAGCCGCCCGGCCA GCCGCGTGAGCCGCCGCAGCCG CGGCAT | 98-147 (Y27L) top |
| GILT 16 | 21 | GGCTGGCCGGGCGGCTGAACAG GAAGCCGCGGTCGCCGCACACG AACTGC | 122-73 (Y27L) bot |
| GILT 20 | 22 | CCGTCTAGAGCTCGGCGCGCCG GCG | 1-25 top strand |

Figure 7:
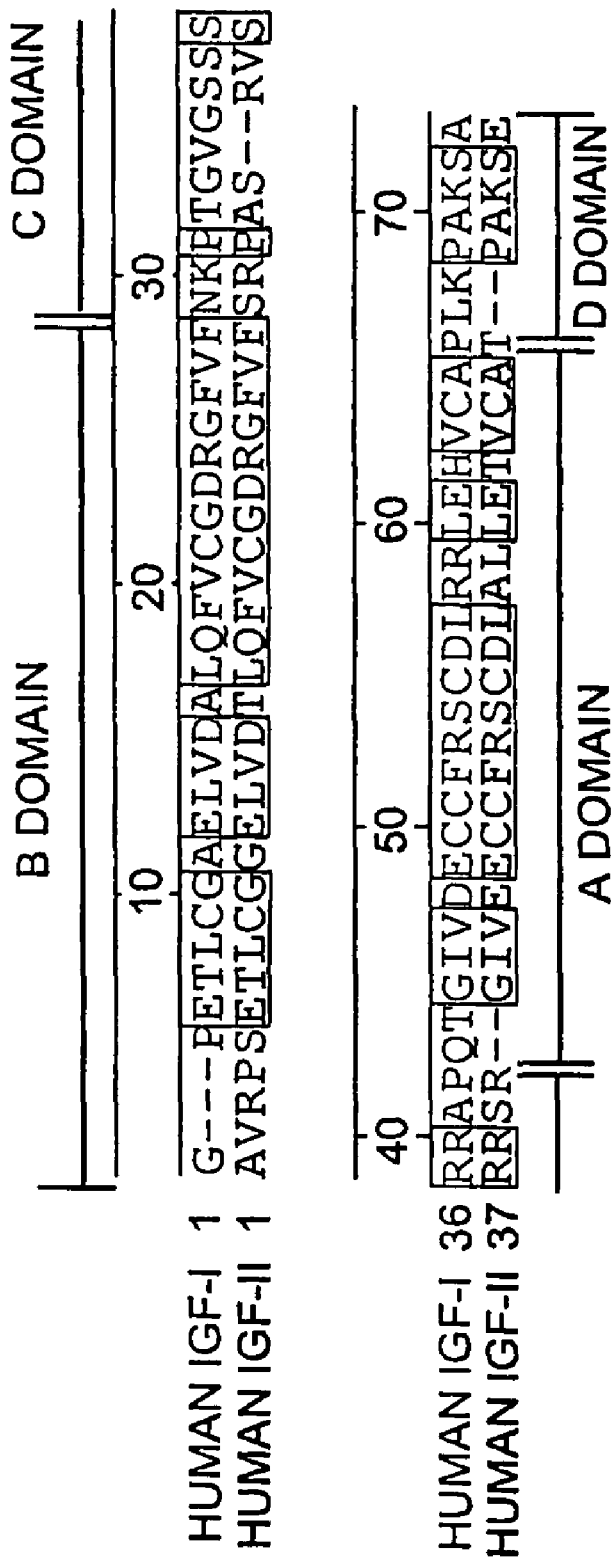
FIG. 7 is an alignment of human IGF-I (SEQ ID NO:7) and IGF-II (SEQ ID NO:8), showing the A, B, C, and D domains.

The purpose of incorporating the indicated mutations into the IGF-II cassette is to insure that the fusion proteins are targeted to the appropriate receptor. Human IGF-II has a high degree of sequence and structural similarity to IGF-I (see, for example FIG. 7) and the B and A chains of insulin (Terasawa et al. (1994) *Embo J.* 13(23):5590-7). Consequently, it is not surprising that these hormones have overlapping receptor binding specificities. IGF-II binds to the insulin receptor, the IGF-I receptor and the cation independent mannose 6-phosphate/IGF-II receptor (CIM6P/IGF-II). The CIM6P/IGF-II receptor is a dual activity receptor acting as a receptor for IGF-II and as a mannose 6-phosphate receptor involved in sorting of lysosomal hydrolases. For a number of years, these two activities were attributed to separate proteins until it was determined that both activities resided in a single protein (Morgan et al. (1987) *Nature* 329(6137):301-7); (Tong et al. (1988) *J. Biol. Chem.* 263(6):2585-8).

The most profound biological effects of IGF-II, such as its mitogenic effect, are mediated through the IGF-I receptor rather than the CIM6P/IGF-II receptor, reviewed in (Ludwig et al. (1995) *Trends in Cell Biology* 5:202-206) also see (Komer et al. (1995) *J. Biol. Chem.* 270(1):287-95). It is thought that the primary result of IGF-II binding to the CIM6P/IGF-II receptor is transport to the lysosome for subsequent degradation. This represents an important means of controlling IGF-II levels and explains why mice carrying null mutants of the CIM6P/IGF-II receptor exhibit perinatal lethality unless IGF-II is also deleted (Lau et al. (1994) *Genes Dev.* 8(24):2953-63); (Wang et al. (1994) *Nature* 372(6505):464-7); (Ludwig et al. (1996) *Dev. Biol.* 177(2):517-35). In methods of the present invention, it is desirable to have the IGF-II fusion proteins bind to the CIM6P/IGF-II receptor. The Y27L and Δ1-7 mutations reduce IGF-II binding to the IGF-I and insulin receptors without altering the affinity for the CIM6P/IGF-II receptor (Sakano et al. (1991) *J. Biol. Chem.* 266(31): 20626-35); (Hashimoto et al. (1995) *J. Biol. Chem.* 270(30): 18013-8). Therefore, according to the invention, these mutant forms of IGF-II should provide a means of targeting fusion proteins specifically to the CIM6P/IGF-II receptor.

In one experiment, 4 different IGF-II cassettes with the appropriate sequences, wild type, Δ1-7, Y27L and Δ1-7/Y27L are made. β-GUS cassettes are fused to IGF-II cassettes and these constructs are put into parasites. Alpha-galactosidase cassettes are also fused to the IGF-II cassettes. GUS fusions have been tested and shown to produce enzymatically active protein.

One preferred construct, shown in FIG. 4, includes the signal peptide of the *L. mexicana* secreted acid phosphatase, SAP-1, cloned into the XbaI site of a modified Pir1-SAT in which the single SalI site has been removed. Fused in-frame is the mature β-GUS sequence, connected to an IGF-II tag by a bridge of three amino acids.

Example 2

GILT Protein Preparation

*L. mexicana* expressing and secreting β-GUS were grown at 26° C. in 100 ml Standard Promastigote medium (M199 with 40 mM HEPES, pH 7.5, 0.1 mM adenine, 0.0005% hemin, 0.0001% biotin, 5% fetal bovine serum, 5% embryonic fluid, 50 units/ml penicillin, 50 μg/ml streptomycin and 50 μg/ml nourseothricin). After reaching a density of approximately $5\times10^6$ promastigotes/ml, the promastigotes were collected by centrifugation for 10 min. at 1000×g at room temperature; these promastigotes were used to inoculate 1 liter of low protein medium (M199 supplemented with 0.1 mM adenine, 0.0001% biotin, 50 units/ml penicillin and 50 μg/ml streptomycin) at room temperature. The 1 liter cultures were contained in 2 liter capped flasks with a sterile stir bar so that the cultures could be incubated at 26° C. with gentle stirring. The 1 liter cultures were aerated twice a day by moving them into a laminar flow hood, removing the caps and swirling vigorously before replacing the caps. When the cultures reached a density of $2\text{-}3\times10^7$ promastigotes/ml, the cultures were centrifuged as described above except the promastigote pellet was discarded and the media decanted into sterile flasks. The addition of 434 g $(NH_4)_2SO_4$ per liter precipitated active GUS protein from the medium; the salted out medium was stored at 4° C. overnight. Precipitated proteins were harvested either by centrifugation at 10,500×g for 30 min. or filtration through Gelman Supor-800 membrane; the proteins were resuspended in 10 mM Tris pH 8, 1 mM $CaCl_2$ and stored at −80° C. until dialysis. The crude preparations from several liters of medium were thawed, pooled, placed in dialysis tubing (Spectra/Por-7, MWCO 25,000), and dialyzed overnight against two 1 liter volumes of DMEM with bicarbonate (Dulbecco's Modified Eagle's Medium).

Example 3

GILT Uptake Assay

Skin fibroblast line GM4668 (human, NIGMS Human Genetic Mutant Cell Repository) is derived from a patient with mucopolysaccharidosis VII; the cells therefore have little or no β-GUS activity. GM4668 cells are therefore particularly useful for testing the uptake of GUS-GILT constructs into human cells. GM4668 cells were cultured in 12-well tissue culture plates in Dulbecco's modified Eagle's medium (DMEM) supplemented with 15% (v/v) fetal calf serum at 37° C. in 5% $CO_2$. Fibroblasts were cultured overnight in the presence of about 150 units of preparations of *Leishmania*-expressed human β-glucuronidase (GUS), GUS-IGF-II fusion protein (GUS-GILT), or mutant GUS-IGF-II fusion protein (GUSΔ-GILT) prepared as described in Example 2. Control wells contained no added enzyme (DMEM media blank). After incubation, media was removed from the wells and assayed in triplicate for GUS activity. Wells were washed five times with 1 ml of 37° C. phosphate-buffered saline, then incubated for 15 minutes at room temperature in 0.2 ml of lysis buffer (10 mM Tris, pH7.5, 100 mM NaCl, 5 mM EDTA, 2 mM 4-(2-aminoethyl)-benzenesulfonyl fluoride hydrochloride (AEBSF, Sigma), and 1% NP-40). Cell lysates were transferred to microfuge tubes, then spun at 13,000 rpm for 5 minutes to remove cell debris. Three 10 μL aliquots of lysate were assayed for protein concentration (Pierce Micro BCA protein assay, Pierce, Ill.).

Three 38 μL aliquots of lysate were assayed for GUS activity using a standard fluorometric assay adapted from (Wolfe et al. (1996) *Protocols for Gene Transfer in Neuroscience: Towards Gene Therapy of Neurological Disorders* 263-274). Assays are done in disposable fluorimeter cuvettes. 150 μl of reaction mix is added to each cuvette. 1 ml reaction mix is 860 μl H2O, 100 μM NaAcetate, 40 μl 25×β-GUS substrate mix. (25×β-GUS substrate mix is a suspension of 250 mg 4-methylumbelliferyl-β-D glucuronide in 4.55 ml ethanol stored at −20° C. in a dessicator. 38 μl of sample are added to the reaction mix and the reaction is incubated at 37° C. Reactions are terminated by addition of 2 ml stop solution (10.6 g $Na_2CO_3$, 12.01 g glycine, H2O to 500 ml, pH 10.5). Fluorescence output is then measured by fluorimeter.

Results of the uptake experiment indicate that the amount of cell-associated GUS-GILT is 10-fold greater that that of the unmodified GUS (FIG. 5). The double mutant construct is about 5-fold more effective than unmodified GUS. These results indicate that the GILT technology is an effective means of targeting a lysosomal enzyme for uptake. Uptake can also be verified using standard immunofluorescence techniques.

Example 4

Competition Experiments

To verify that the GILT-mediated uptake occurs via the IGF-II binding site on the cation-independent M6P receptor, competition experiments were performed using recombinant IGF-II. The experimental design was identical to that described above except that GM4668 fibroblasts were incubated with indicated proteins in DMEM minus serum +2% BSA for about 18 hours. Each β-GUS derivative was added at 150 Upper well. 2.85 μg IGF-II was added to each well for competition. This represents approximately a 100 fold molar excess over GILT-GUS, a concentration sufficient to compete for binding to the M6P/IGF-II receptor.

Results of the competition experiment are depicted in FIG. 6. In the absence of IGF-II over 24 units of GILT-GUS/mg lysate were detected. Upon addition of IGF-II, the amount of cell associated GILT-GUS fell to 5.4 U. This level is similar to the level of unmodified GUS taken up by the fibroblasts. Thus, the bulk of the GILT protein uptake can be competed by IGF-II indicating that the uptake is indeed occurring through a specific receptor-ligand interaction.

Example 5

Gene Product Expression in Serum Free Media

Expression products can also be isolated from serum free media. In general, the expression strain is grown in medium with serum, diluted into serum free medium, and allowed to grow for several generations, preferably 2-5 generations, before the expression product is isolated. For example, production of secreted targeted therapeutic proteins can be isolated from *Leishmania mexicana* promastigotes that are cultured initially in 50 ml 1×M199 medium in a 75 cm2 flask at 27° C. When the cell density reaches 1-3×10$^7$/ml, the culture is used to inoculate 1.2 L of M199 media. When the density of this culture reaches about 5×10$^6$/ml, the cells are harvested by centrifugation, resuspended in 180 ml of the supernatant and used to inoculate 12 L of "Zima" medium in a 16 L spinner flask. The initial cell density of this culture is typically about 5×10$^5$/ml. This culture is expanded to a cell density of about 1.0–1.7×10e$^7$ cells/ml. When this cell density is reached, the cells are separated from the culture medium by centrifugation and the supernatant is filtered at 4° C. through a 0.2μ filter to remove residual promastigotes. The filtered media was concentrated from 12.0 L to 500 ml using a tangential flow filtration device (MILLIPORE Prep/Scale-TFF cartridge).

Preferred growth media for this method are M199 and "Zima" growth media. However, other serum containing and serum free media are also useful. M199 growth media is as follows: (1 L batch)=200 ml 5×M199 (with phenol red pH indicator)+636 ml H$_2$O, 50.0 ml fetal bovine serum, 50.0 ml EF bovine embryonic fluid, 1.0 ml of 50 mg/ml nourseothricin, 2.0 ml of 0.25% hemin in 50% triethanolamine, 10 ml of 10 mM adenine in 50 mM Hepes pH 7.5, 40.0 ml of 1M Hepes pH 7.5, 1 ml of 0.1% biotin in 95% ethanol, 10.0 ml of penicillin/streptomycin. All sera used are inactivated by heat. The final volume=1 L and is filter sterilized. "Zima" modified M199 media is as follows: (20.0 L batch)=219.2 g M199 powder (–)phenol red+7.0 g sodium bicarbonate, 200.0 ml of 10 mM adenine in 50 mM Hepes pH 7.5, 800.0 ml Of Hepes free acid pH 7.5, 20.0 ml 0.1% biotin in 95% ethanol, 200.0 ml penicillin/streptomycin, Final volume=20.0 L and is filter sterilized.

Figure 8:
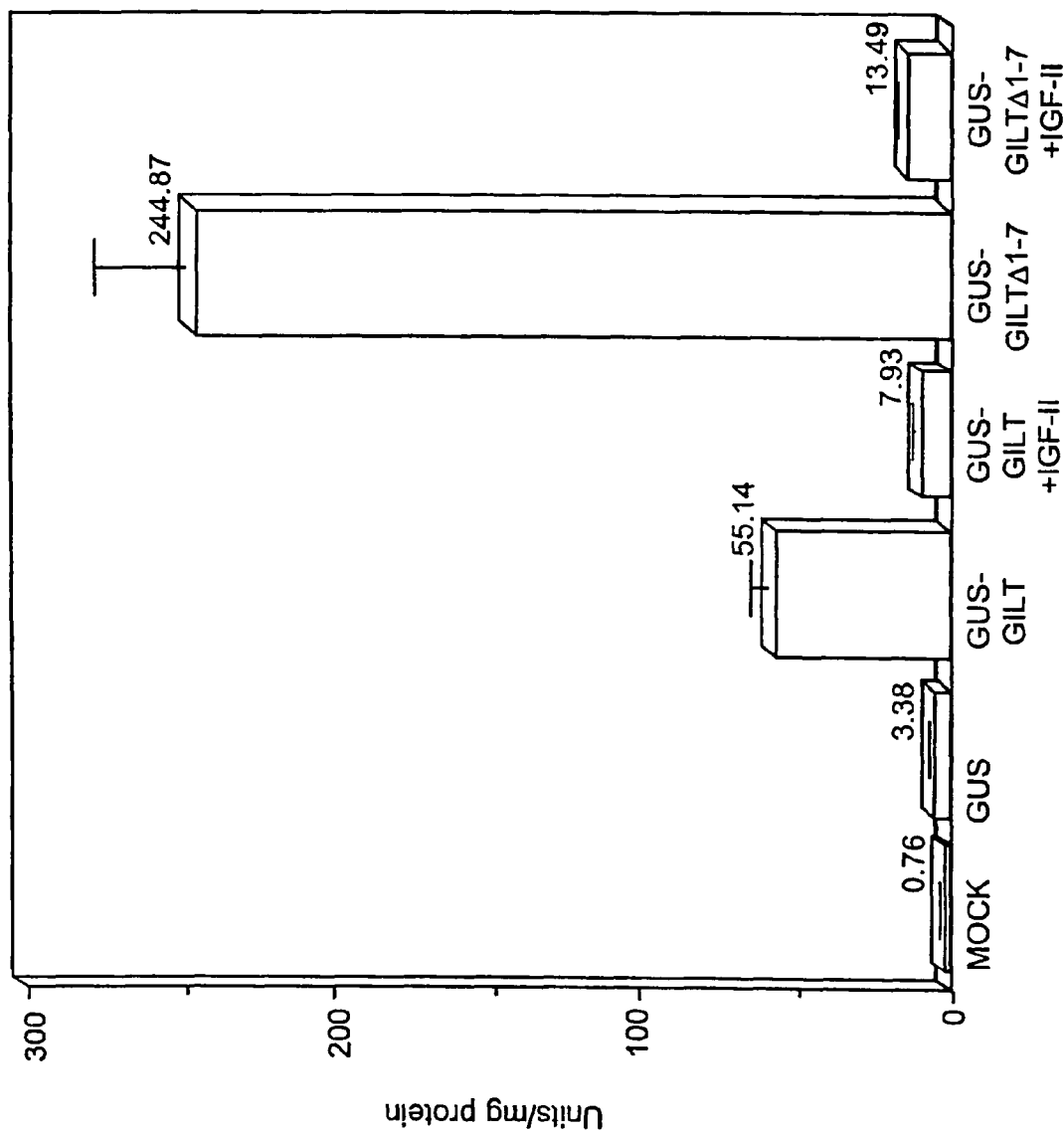
FIG. 8 depicts GUS in GM4668 cells exposed to GUS, GUS-GILT, GUS-GILT, GUS-GILT with a deletion of the seven amino-terminal residues (GUS-GILT Δ1-7), GUS-GILT in the presence of excess IGF-II, GUS-GILT Δ1-7 in the presence of excess IGF-II, or a negative control (Mock).
Figure 9A:
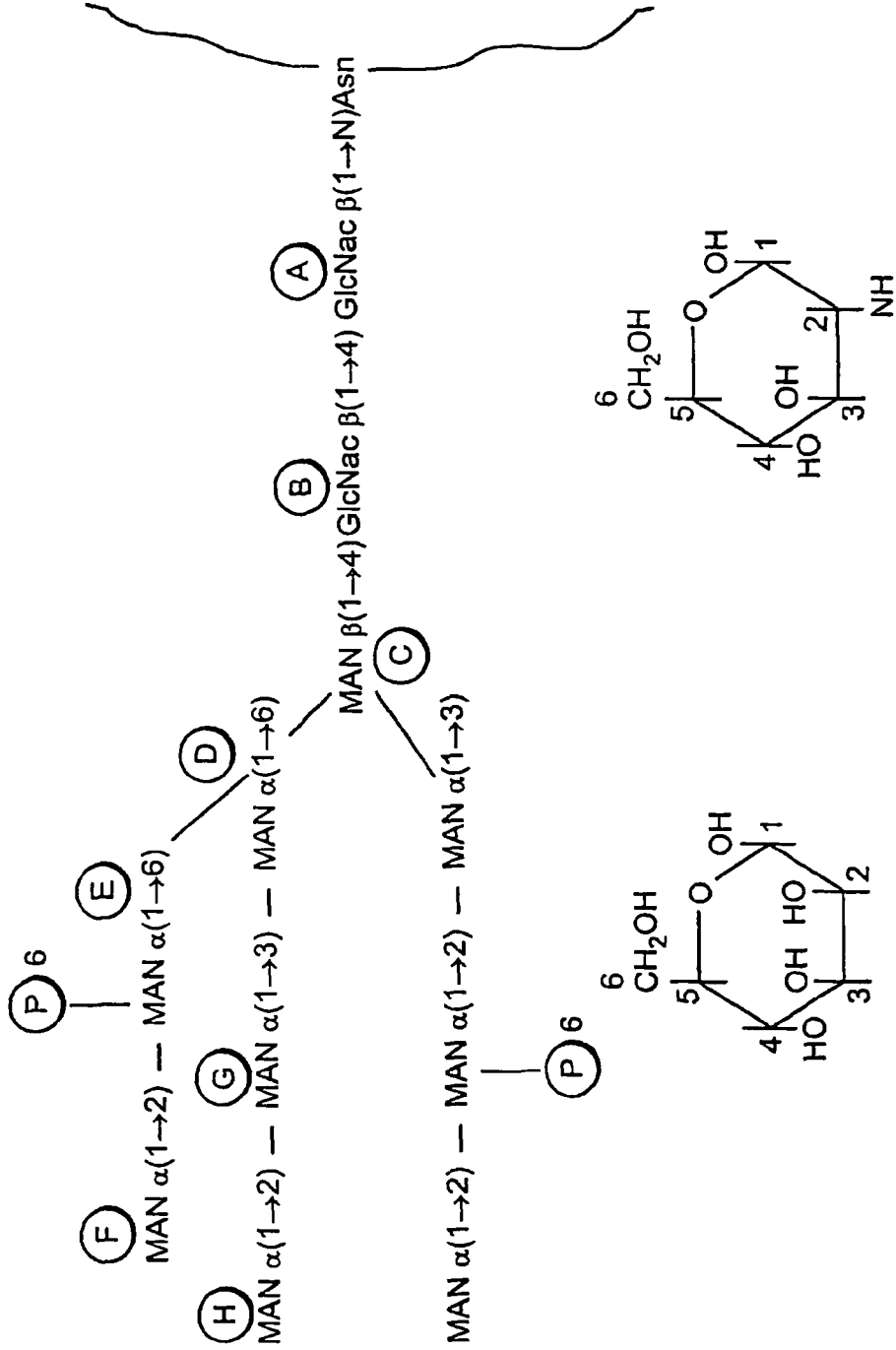
FIG. 9A depicts one form of a phosphorylated high mannose carbohydrate structure linked to a glycoprotein via an asparagine residue, and also depicts the structures of mannose and N-acetylglucosamine (GlcNAc).
Figure 9B:
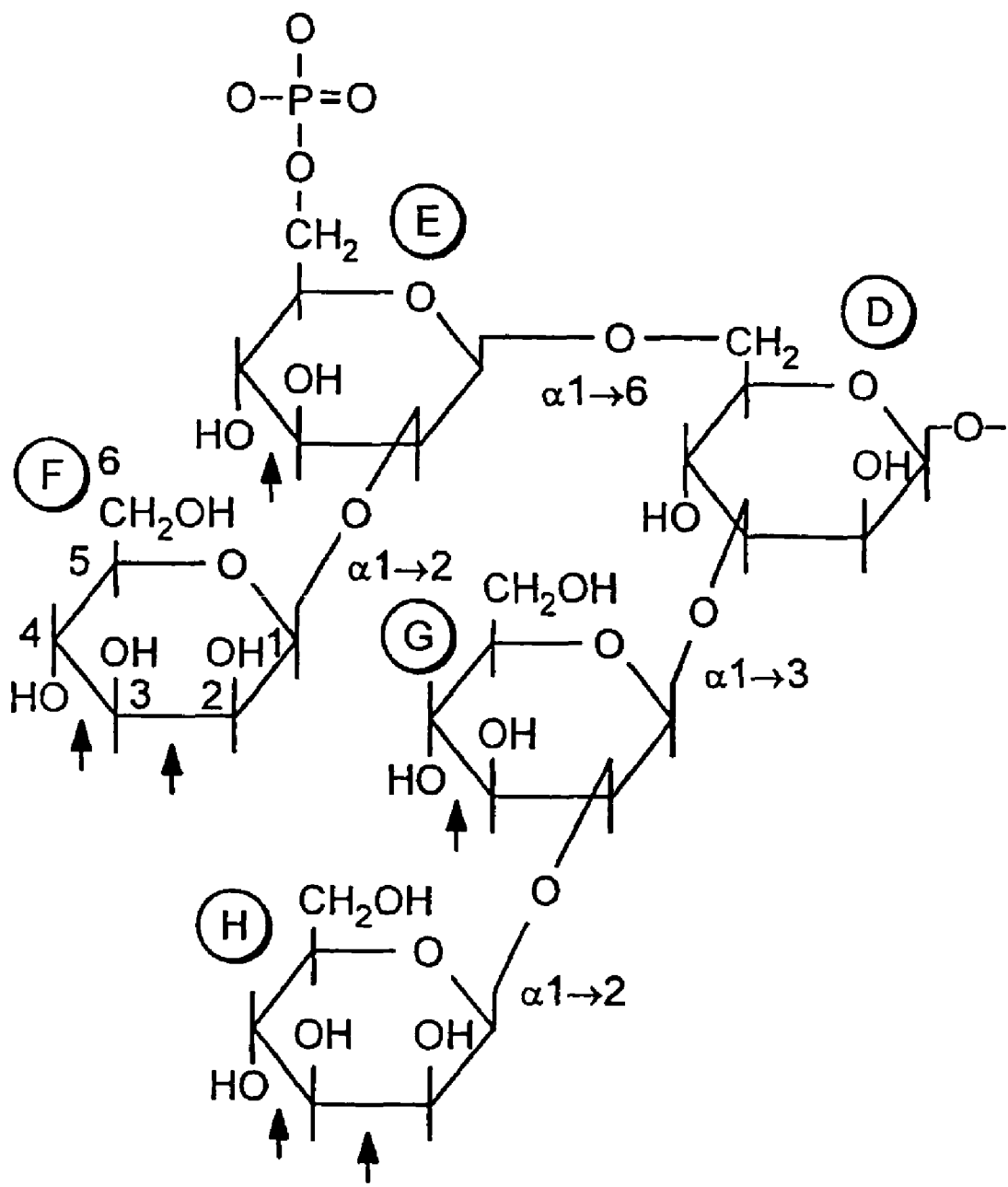
FIG. 9B depicts a portion of the high mannose carbohydrate structure at a higher level of detail, and indicates positions vulnerable to cleavage by periodate treatment. The positions of the sugar residues within the carbohydrate structure are labeled with circled, capital letters A-H; phosphate groups are indicated with a circled capital P.

The targeted therapeutic proteins are preferably purified by Concanavalin A (ConA) chromatography. For example, when a culture reaches a density of >1.0×10$^7$ promastigotes/ml, *L. mexicana* are removed by centrifugation, 10 min at 500×g. The harvested culture medium is passed through a 0.2 μm filter to remove particulates before being loaded directly onto a ConA-agarose column (4% cross-linked beaded agarose, Sigma). The ConA-agarose column is pretreated with 1 M NaCl, 20 mM Tris pH 7.4, 5 mM each of CaCl$_2$, MgCl$_2$ and MnCl$_2$ and then equilibrated with 5 volumes of column buffer (20 mM Tris pH 7.4, 1 mM CaCl$_2$, and 1 mM MnCl$_2$). A total of 179,800 units (nmol/hr) of GUS activity (in 2 L) in culture medium is loaded onto a 22 ml ConA agarose column. No activity is detectable in the flow through or wash. The GUS activity is eluted with column buffer containing 200 mM methyl mannopyranoside. Eluted fractions containing the activity peak are pooled and concentrated. Uptake and competition experiments were performed as described in Examples 3 and 4, except that the organisms were grown in serum-free medium and purified with ConA; about 350-600 units of enzyme were applied to the fibroblasts. Results are shown in FIG. 8.

Example 6

Competition Experiments Using Denatured IGF-II as Competitor

The experiment in Example 4 is repeated using either normal or denatured IGF-II as competitor. As in Example 4, the amount of cell-associated GUS-GILT is reduced when coincubated with normal IGF-II concentrations that are effective for competition but, at comparable concentrations, denatured IGF-II has little or no effect.

Example 7

Enzyme Assays

Assays for GUS activity are performed as described in Example 3 and/or as described below.

Glass assay tubes are numbered in triplicate, and 100 μL of 2×GUS reaction mix are added to each tube. 2×GUS reaction mix is prepared by adding 100 mg of 4-methylumbelliferyl-β-D glucuronide to 14.2 mL 200 mM sodium acetate, pH adjusted to 4.8 with acetic acid. Up to 100 μL of sample are added to each tube; water is added to a final reaction volume of 200 μL. The reaction tubes are covered with parafilm and incubated in a 37° C. water bath for 1-2 hours. The reaction is stopped by addition of 1.8 mL of stop buffer (prepared by dissolving 10.6 g of Na$_2$CO$_3$ and 12.01 g of glycine in a final volume of 500 mL of water, adjusting the pH to 10.5 and filter-sterilizing into a repeat-dispenser). A fluorimeter is then calibrated using 2 mL of stop solution as a blank, and the fluorescence is read from the remaining samples. A standard curve is prepared using 1, 2, 5, 10, and 20 μL of a 166 μM 4-methylumbelliferone standard in a final volume of 2 mL stop buffer.

The 4-methylumbelliferone standard solution is prepared by dissolving 2.5 mg 4-methylumbelliferone in 1 mL ethanol and adding 99 mL of sterile water, giving a concentration of approximately 200 nmol/mL. The precise concentration is determined spectrophotometrically. The extinction coefficient at 360 nm is 19,000 cm$^{-1}$ M$^{-1}$. For example, 100 μL is added to 900 μL of stop buffer, and the absorbance at 360 nm is read. If the reading is 0.337, then the concentration of the standard solution is 0.337×10 (dilution)/19,000=177 μM, which can then be diluted to 166 μM by addition of an appropriate amount of sterile water.

Example 8

Binding Uptake and Halflife Experiments

Binding of GUS-GILT proteins to the M6P/IGF-II receptor on fibroblasts are measured and the rate of uptake is assessed similar to published methods (York et al. (1999) *J. Biol. Chem.* 274(2):1164-71). GM4668 fibroblasts cultured in 12 well culture dishes as described above are washed in ice-cold media minus serum containing 1% BSA. Ligand, (either GUS, GUS-GILT or GUS-AGILT, or control proteins) is added to cells in cold media minus serum plus 1% BSA. Upon addition of ligand, the plates are incubated on ice for 30 minutes. After 30 minutes, ligand is removed and cells are washed quickly 5 times with ice cold media. Wells for the 0 time point receive 1 ml ice cold stripping buffer (0.2 M Acetic acid, pH 3.5, 0.5M NaCl). The plate is then floated in a 37° water bath and 0.5 ml prewarmed media is added to initiate uptake. At every stopping point, 1 ml of stripping buffer is added. When the experiment is over, aliquots of the stripping buffer are saved for fluorometric assay of β-glucuronidase activity as described in Example 3. Cells are then lysed as described above and the lysate assayed for β-glucuronidase activity. Alternatively, immunological methods can be used to test the lysate for the presence of the targeted therapeutic protein.

It is expected that GUS-GILT is rapidly taken up by fibroblasts in a matter of minutes once the temperature is shifted to 37° C. (York et al. (1999) *J. Biol. Chem.* 274(2): 1164-71) and that the enzyme activity persists in the cells for many hours.

Example 9

Protein Production in Mammalian Cells

CHO Cells

GUS-GILTΔ1-7 and GUSΔC18-GILTΔ1-7 were expressed in CHO cells using the system of Ulmasov et al. (2000) *PNAS* 97(26): 14212-14217. Appropriate gene cassettes were inserted into the Eco RI site of the pCXN vector, which was electroporated into CHO cells at 50 µF and 1,200 V in a 0.4-cm cuvette. Selection of colonies and amplification was mediated by 400 µg/mL G418 for 2-3 weeks. The CHO cells were propagated in MEM media supplemented with 15% FBS, 1.2 mM glutamine, 50 µg/mL proline, and 1 mM pyruvate. For enzyme production cells were plated in multifloor flasks in MEM. Once cells reached confluence, collection medium (Weymouth medium supplemented with 2% FBS, 1.2 mM glutamine, and 1 mM pyruvate) was applied to the cells. Medium containing the secreted recombinant enzyme was collected every 24-72 hours. A typical level of secretion for one GUS-GILTΔ1-7 cell line was 4000-5000 units/mL/24 hours.

A number of GUSΔC18-GILTΔ1-7 CHO lines were assayed for the amount of secreted enzyme produced. The six highest producers secreted between 8600 and 14900 units/mL/24 hours. The highest producing line was selected for collection of protein.

HEK 293 Cells

GUS-GILT cassettes were cloned into pCEP4 (Invitrogen) for expression in HEK 293 cells. Cassettes used included wild-type GUS-GILT; GUS-GILTΔ1-7; GUS-GILTY27L; GUSΔC18-GILTΔ1-7; GILTY27L, and GUS-GILTF19S/E12K.

HEK 293 cells were cultured to 50-80% confluency in 12-well plates containing DMEM medium with 4 mM glutamine and 10% FBS. Cells were transfected with pCEP-GUS-GILT DNA plasmids using FuGENE 6 (Roche) as described by the manufacturer. 0.5 µg DNA and 2 µL of FuGENE 6 were added per well. Cells were removed from wells 2-3 days post-transfection using trypsin, then cultured in T25 cm² culture flasks containing the above DMEM medium with 100 µg/mL hygromycin to select for a stable population of transfected cells. Media containing hygromycin were changed every 2-3 days. The cultures were expanded to T75 cm² culture flasks within 1-2 weeks. For enzyme production cells were plated in multifloor flasks in DMEM. Once cells reached confluence, collection medium (Weymouth medium supplemented with 2% FBS, 1.2 mM glutamine, and 1 mM pyruvate) was applied to the cells. This medium has been optimized for CHO cells, not for 293 cells; accordingly, levels of secretion with the HEK 293 lines may prove to be significantly higher in alternate media.

Levels of secreted enzyme are shown in Table 4.

TABLE 4

| Cell line | Recombinant Protein | Units/mL/24 hours |
|---|---|---|
| HEK293 2-1 | GUS-GILT | 3151 |
| HEK293 2-2 | GUSΔC18-GILTΔ1-7 | 10367 |
| HEK293 2-3 | GUS-GILTΔ1-7 | 186 |
| HEK293 4-4 | GILTY27L | 3814 |
| HEK293 3-5 | GUS-GILTF19S/E12K | 13223 |

TABLE 4-continued

| Cell line | Recombinant Protein | Units/mL/24 hours |
|---|---|---|
| HEK293 3-6 | GILTY27L | 7948 |
| CHO 15 | GUSΔC18-GILTΔ1-7 | 18020 |

Example 10

Purification of GUS-GILT Fusion Proteins

Chromoatography, including conventional chromatography and affinity chromatography, can be used to purify GUS-GILT fusion proteins.

Conventional Chromatography

One procedure for purifying GUS-GILT fusion proteins produced in *Leishmania* is described in Example 2. An alternative procedure is described in the following paragraph.

Culture supernatants from *Leishmania mexicana* cell lines expressing GUS-GILT fusions were harvested, centrifuged, and passed through a 0.21 filter to remove cell debris. The supernatants were concentrated using a tangential ultrafilter with a 100,000 molecular weight cutoff and stored at −80° C. Concentrated supernatants were loaded directly onto a column containing Concanavalin A (ConA) immobilized to beaded agarose. The column was washed with ConA column buffer (50 mM Tris pH 7.4, 1 mM CaCl$_2$, 1 mM MnCl$_2$) before mannosylated proteins including GUS-GILT fusions were eluted using a gradient of 0-0.2 M methyl-α-D-pyranoside in the ConA column buffer. Fractions containing glucuronidase activity (assayed as described in Example 7) were pooled, concentrated, and the buffer exchanged to SP column buffer (25 mM sodium phosphate pH 6, 20 mM NaCl, 1 mM EDTA) in preparation for the next column. The concentrated fractions were loaded onto an SP fast flow column equilibrated in the same buffer, and the column was washed with additional SP column buffer. The GUS-GILT fusions were eluted from the column in two steps: 1) a gradient of 0-0.15 M glucuronic acid in 25 mM sodium phosphate pH 6 and 10% glycerol, followed by 0.2 M glucuronic acid, 25 mM sodium phosphate pH 6, 10% glycerol. Fractions containing glucuronidase activity were pooled, and the buffer exchanged to 20 mM potassium phosphate pH 7.4. These pooled fractions were loaded onto an HA-ultrogel column equilibrated with the same buffer. The GUS-GILT fusion proteins were eluted with an increasing gradient of phosphate buffer, from 145-340 mM potassium phosphate pH 7.4. The fractions containing glucuronidase activity were pooled, concentrated, and stored at −80° C. in 20 mM Tris pH 8 with 25% glycerol.

A conventional chromatography method for purifying GUS-GILT fusion proteins produced in mammalian cells is described in the following paragraphs.

Mammalian cells overexpressing a GUS-GILT fusion protein are grown to confluency in Nunc Triple Flasks, then fed with serum-free medium (Waymouth MB 752/1) supplemented with 2% fetal bovine serum to collect enzyme for purification. The medium is harvested and the flasks are refed at 24 hour intervals. Medium from several flasks is pooled and centrifuged at 5000×g for 20 minutes at 4° C. to remove detached cells, etc. The supernatant is removed and aliquots are taken for a β-GUS assay. The medium can now be used directly for purification or frozen at −20° C. for later use.

1 L of secretion medium is thawed at 37° C. (if frozen), filtered through a 0.2μ filter, and transferred to a 4 L beaker. The volume of the medium is diluted 4-fold by addition of 3 L of dd water to reduce the salt concentration; the pH of the diluted medium is adjusted to 9.0 using 1 M Tris base. 50 mL of DEAE-Sephacel pre-equilibrated with 10 mM Tris pH 9.0 is added to the diluted medium and stirred slowly with a large stirring bar at 4° C. for 2 hours. (A small aliquot can be removed, microfuged, and the supernatant assayed to monitor binding.) When binding is complete, the resin is collected on a fritted glass funnel and washed with 750 mL of 10 mM Tris pH 9.0 in several batches. The resin is transferred to a 2.5 cm column and washed with an additional 750 mL of the same buffer at a flow rate of 120 mL/hour. The DEAE column is eluted with a linear gradient of 0-0.4 M NaCl in 10 mM Tris pH 9.0. The fractions containing the GUS-GILT fusion proteins are detected by 4-methylumbelliferyl-β-D glucuronide assay, pooled, and loaded onto a 600 mL column of Sephacryl S-200 equilibrated with 25 mM Tris pH 8, 1 mM β-glycerol phosphate, 0.15 M sodium chloride and eluted with the same buffer.

The fractions containing the GUS-GILT fusion proteins are pooled and dialyzed with 3×4 L of 25 mM sodium acetate pH 5.5, 1 mM β-glycerol phosphate, 0.025% sodium azide. The dialyzed enzyme is loaded at a flow rate of 36 mL/hour onto a 15 mL column of CM-Sepharose equilibrated with 25 mM sodium acetate pH 5.5, 1 mM β-glycerol phosphate, 0.025% sodium azide. It is then washed with 10 column volumes of this same buffer. The CM column is eluted with a linear gradient of 0-0.3 M sodium chloride in the equilibration buffer. The fractions containing the GUS-GILT fusion proteins are pooled and loaded onto a 2.4×70 cm (Bed volume=317 mL) column of Sephacryl S-300 equilibrated with 10 mM Tris pH 7.5, 1 mM β-glycerol phosphate, 0.15 M NaCl at a flow rate of 48 mL/hour. The fractions containing the fusion proteins are pooled; the pool is assayed for GUS activity and for protein concentration to determine specific activity. Aliquots are run on SDS-PAGE followed by Coomassie or silver staining to confirm purity. If a higher concentration of enzyme is required, Amicon Ultrafiltration Units with an XM-50 membrane (50,000 molecular weight cutoff) or Centricon C-30 units (30,000 molecular weight cutoff) can be used to concentrate the fusion protein. The fusion protein is stored at −80° C. in the 10 mM Tris pH 7.5, 1 mM sodium β-glycerol phosphate, 0.15 M NaCl buffer.

Affinity Chromatography

Affinity chromatography conditions are essentially as described in Islam et al. (1993) *J. Biol. Chem.* 268(30):22627-22633. Conditioned medium from mammalian cells overexpressing a GUS-GILT fusion protein (collected and centrifuged as described above for conventional chromatography) is filtered through a 0.22μ filter. Sodium chloride (crystalline) is added to a final concentration of 0.5M, and sodium azide is added to a final concentration of 0.025% by adding 1/400 volume of a 10% stock solution. The medium is applied to a 5 mL column of anti-human β-glucuronidase-Affigel 10 (pre-equilibrated with Antibody Sepharose Wash Buffer: 10 mM Tris pH 7.5, 10 mM potassium phosphate, 0.5 M NaCl, 0.025% sodium azide) at a rate of 25 mL/hour at 4° C. Fractions are collected and monitored for any GUS activity in the flow-through. The column is washed at 36 mL/hour with 10-20 column volumes of Antibody Sepharose Wash Buffer. Fractions are collected and monitored for GUS activity. The column is eluted at 36 mL/hour with 50 mL of 10 mM sodium phosphate pH 5.0+3.5 M $MgCl_2$. 4 mL fractions are collected and assayed for GUS activity. Fractions containing the fusion protein are pooled, diluted with an equal volume of P6 buffer (25 mM Tris pH 7.5, 1 mM β-glycerol phosphate, 0.15 mM NaCl, 0.025% sodium azide) and desalted over a BioGel P6 column (pre-equilibrated with P6 buffer) to remove the $MgCl_2$ and to change the buffer to P6 buffer for storage. The fusion protein is eluted with P6 buffer, fractions containing GUS activity are pooled, and the pooled fractions assayed for GUS activity and for protein. An SDS-PAGE gel stained with Coomassie Blue or silver stain is used to confirm purity. The fusion protein is stored frozen at −80° C. in P6 buffer for long-term stability.

Example 11

Uptake Experiments on Mammalian-Produced Proteins

Culture supernatants from HEK293 cell lines or CHO cell lines producing GUS or GUS-GILT constructs were harvested through a 0.2 μm filter to remove cells GM 4668 fibroblasts were cultured in 12-well tissue culture plates in DMEM supplemented with 15% (v/v) fetal calf serum at 37° C. in 5% $CO_2$. Cells were washed once with uptake medium (DMEM+2% BSA (Sigma A-7030)) at 37° C. Fibroblasts were then cultured (3-21 hours) with 1000-4000 units of enzyme per mL of uptake medium. In some experiments, competitors for uptake were added. Mannose-6-phosphate (Calbiochem 444100) was added to some media at concentrations from 2-8 mM and pure recombinant IGF-II (Cell Sciences OU100) was added to some media at 2.86 mM, representing a 10-100 fold molar excess depending on the quantity of input enzyme. Uptake was typically measured in triplicate wells.

After incubation, the media were removed from the wells and assayed in duplicate for GUS activity. Wells were washed five times with 1 mL of 37° C. phosphate-buffered saline, then incubated for 15 minutes at room temperature in 0.2 mL of lysis buffer (10 mM Tris, pH 7.5, 100 mM NaCl, 5 mM EDTA, and 1% NP-40). Cell lysates were transferred to microfuge tubes and spun at 13,000 rpm for 5 minutes to remove cell debris. Two 10 μL aliquots of lysate were assayed for GUS activity using a standard fluorometric assay. Three 10 μL aliquots of lysate were assayed for protein concentration (Pierce Micro BCA protein assay, Pierce, Ill.).

An initial experiment compared uptake of CHO-produced GUS-GILTΔ1-7 with CHO-produced GUSΔC18-GILTΔ1-7. As shown in Table 5, the GUSΔC18-GILTΔ1-7 protein, which was engineered to eliminate a potential protease cleavage site, has significantly higher levels of uptake levels that can be inhibited by IGF-II and by M6P. In contrast, the uptake of a recombinant GUS produced in mammalian cells lacking the IGF-II tag was unaffected by the presence of excess IGF-II but was completely abolished by excess M6P. In this experiment, uptake was performed for 18 hours.

TABLE 5

| Enzyme | Input units | Uptake (units/mg) | +IGF-II (units/mg) | % IGF-II inhibition | +M6P (units/mg) | % M6P inhibition |
|---|---|---|---|---|---|---|
| CHO GUS-GILTΔ1-7 | 982 | 310 ± 27 | 84 ± 20 | 73 | 223 ± 36 | 28 |
| CHO GUSΔC18-GILTΔ1-7 | 1045 | 704 ± 226 | 258 ± 50 | 63 | 412 ± 79 | 41 |
| CHO GUS | 732 | 352 ± 30 | 336 ± 77 | 5 | 1 ± 0.2 | 99.7 |

A subsequent experiment assessed the uptake of CHO- and HEK293-produced enzymes by human fibroblasts from MPSVII patients. In this experiment, uptake was for 21 hours.

TABLE 6

| Enzyme | Input units | Uptake (units/mg) | +IGF-II Uptake (units/mg) | % IGF-II inhibition |
|---|---|---|---|---|
| CHO GUSΔC18-GILTΔ1-7 | 2812 | 4081 ± 1037 | 1007 ± 132 | 75 |
| HEK GUS-GILT | 2116 | 1432 ± 196 | | |
| HEK GUSΔC18-GILTΔ1-7 | 3021 | 5192 ± 320 | 1207 ± 128 | 77 |
| HEK GUS-GILTY27L | 3512 | 1514 ± 203 | | |
| HEK GUS-GILTF19SE12K | 3211 | 4227 ± 371 | 388 ± 96 | 90.8 |
| HEK GUS-GILTF19S | 3169 | 4733 ± 393 | 439 ± 60 | 90.7 |

A further experiment assessed the uptake of selected enzymes in the presence of IGF-II, 8 mM M6P, or both inhibitors. Uptake was measured for a period of 22.5 hours.

TABLE 7

| Enzyme | Input units | Uptake (units/mg) | +IGF-II (units/mg) | % IGF-II inhibition | +M6P (units/mg) | % M6P inhibition | +IGF-II + M6P (units/mg) | % IGF-II + M6P inhibition |
|---|---|---|---|---|---|---|---|---|
| CHO GUSΔC18-GILTΔ1-7 | 1023 | 1580 ± 150 | 473 ± 27 | 70 | 639 ± 61 | 60 | 0 ± 1 | 100 |
| HEK GUS-GILTF19S E12K | 880 | 1227 ± 76 | 22 ± 2 | 98.2 | 846 ± 61 | 31 | 0 ± 3 | 100 |
| HEK GUS-GILTF19S | 912 | 1594 ± 236 | 217 ± 17 | 86 | 952 ± 96 | 60 | 15 ± 2 | 99.06 |

The experiments described above show that CHO and HEK293 production systems are essentially equivalent in their ability to secrete functional recombinant proteins. The experiments also show that the presence of excess IGF-II diminishes uptake of tagged proteins by 70-90+%, but does not markedly affect uptake of untagged protein (4.5%), indicating specific IGF-II-mediated uptake of the mammalian-produced protein. Unlike *Leishmania*-produced proteins, the enzymes produced in mammalian cells are expected to contain M6P. The presence of two ligands on these proteins capable of directing uptake through the M6P/IGF-II receptor implies that neither excess IGF-II nor excess M6P should completely abolish uptake. Furthermore, since the two ligands bind to discrete locations on the receptor, binding to the receptor via one ligand should not be markedly affected by the presence of an excess of the other competitor.

Example 12

In Vivo Therapy

Initially, GUS minus mice can be used to assess the effectiveness of GUS-GILT and derivatives thereof in enzyme replacement therapy. GUS minus mice are generated by heterozygous matings of B6.C—H-2$^{bm1}$/ByBIR-gus$^{mps}$/+ mice as described by Birkenmeier et al. (1989) *J. Clin. Invest* 83(4):1258-6. Preferably, the mice are tolerant to human β-GUS. The mice may carry a transgene with a defective copy of human β-GUS to induce immunotolerance to the human protein (Sly et al. (2001) *PNAS* 98:2205-2210). Alternatively, human β-GUS (e.g. as a GUS-GILT protein) can be administered to newborn mice to induce immunotolerance. However, because the blood-brain barrier is not formed until about day 15 in mice, it is simpler to determine whether GILT-GUS crosses the blood-brain barrier when initiating injections in mice older than 15 days; transgenic mice are therefore preferable.

The initial experiment is to determine the tissue distribution of the targeted therapeutic protein. At least three mice receive a CHO-produced GILT-tagged β-GUS protein referred to herein as GUSΔC18-GILTΔ1-7, in which GUSΔ18, a β-GUS protein omitting the last eighteen amino acids of the protein, is fused to the N-terminus of Δ1-7 GILT, an IGF-II protein missing the first seven amino acids of the mature protein. Other mice receive either β-GUS, a buffer control, or a GUSΔC18-GILTΔ1-7 protein treated with periodate and sodium borohydride as described in Example 14. Generally, preferred doses are in the range of 0.5-7 mg/kg body weight. In one example, the enzyme dose is 1 mg/kg body weight administered intravenously, and the enzyme concentration is about 1-3 mg/mL. In addition, at least three mice receive a dose of 5 mg/kg body weight of GUSΔC18-GILTΔ1-7 protein treated with periodate and sodium borohydride. After 24 hours, the mice are sacrificed and the following organs and tissues are isolated: liver, spleen, kidney, brain, lung, muscle, heart, bone, and blood. Portions of each tissue are homogenized and the β-GUS enzyme activity per mg protein is determined as described in Sly et al. (2001) *PNAS* 98:2205-2210. Portions of the tissues are prepared for histochemistry and/or histopathology carried out by published methods (see, e.g., Vogler et al. (1990) *Am J. Pathol.* 136:207-217).

Further experiments include multiple injection protocols in which the mice receive weekly injections at a dose of 1 mg/kg body weight. In addition, measurement of the half-life of the periodate-modified enzyme is determined in comparison with untreated enzyme as described in Example 14.

Two other assay formats can be used. In one format, 3-4 animals are given a single injection of 20,000 U of enzyme in 100 µl enzyme dilution buffer (150 mM NaCl, 10 mM Tris, pH7.5). Mice are killed 72-96 hours later to assess the efficacy of the therapy. In a second format, mice are given weekly injections of 20,000 units over 3-4 weeks and are killed 1 week after the final injection. Histochemical and histopathologic analysis of liver, spleen and brain are carried out by published methods (Birkenmeier et al. (1991) *Blood* 78(11): 3081-92; Sands et al. (1994) *J. Clin. Invest* 93(6):2324-31; Daly et al. (1999) *Proc. Natl. Acad. Sci. USA* 96(5):2296-300). In the absence of therapy, cells (e.g. macrophages and Kupffer cells) of GUS minus mice develop large intracellular storage compartments resulting from the buildup of waste products in the lysosomes. It is anticipated that in cells in mice treated with GUS-GILT constructs, the size of these compartments will be visibly reduced or the compartments will shrink until they are no longer visible with a light microscope.

Similarly, humans with lysosomal storage diseases will be treated using constructs targeting an appropriate therapeutic portion to their lysosomes. In some instances, treatment will take the form of regular (e.g. weekly) injections of a GILT protein. In other instances, treatment will be achieved through administration of a nucleic acid to permit persistent in vivo expression of a GILT protein, or through administration of a cell (e.g. a human cell, or a unicellular organism) expressing the GILT protein in the patient. For example, the GILT protein can be expressed in situ using a *Leishmania* vector as described in U.S. Pat. No. 6,020,144, issued Feb. 1, 2000; U.S. Provisional Application No. 60/250,446; and U.S. Provisional Application No. 60/290,281, "Protozoan Expression Systems for Lysosomal Storage Disease Genes", filed May 11, 2001.

Targeted therapeutic proteins of the invention can also be administered, and their effects monitored, using methods (enzyme assays, histochemical assays, neurological assays, survival assays, reproduction assays, etc.) previously described for use with GUS. See, for example, Vogler et al. (1993) *Pediatric Res.* 34(6):837-840; Sands et al. (1994) *J. Clin. Invest.* 93:2324-2331; Sands et al. (1997) *J. Clin. Invest.* 99:1596-1605; O'Connor et al. (1998) *J. Clin. Invest.* 101: 1394-1400; and Soper et al. (1999) 45(2): 180-186.

Example 13

The objective of these experiments is to evaluate the efficacy of GILT-modified alpha-galactosidase A (α-GAL A) as an enzyme replacement therapy for Fabry's disease.

Fabry's disease is a lysosomal storage disease resulting from insufficient activity of α-GAL A, the enzyme responsible for removing the terminal galactose from GL-3 and other neutral sphingolipids. The diminished enzymatic activity occurs due to a variety of missense and nonsense mutations in the x-linked gene. Accumulation of GL-3 is most prevalent in lysosomes of vascular endothelial cells of the heart, liver, kidneys, skin and brain but also occurs in other cells and tissues. GL-3 buildup in the vascular endothelial cells ultimately leads to heart disease and kidney failure.

Enzyme replacement therapy is an effective treatment for Fabry's disease, and its success depends on the ability of the therapeutic enzyme to be taken up by the lysosomes of cells in which GL-3 accumulates. The Genzyme product, Fabrazyme, is recombinant α-GAL A produced in DUKX B11 CHO cells that has been approved for treatment of Fabry's patients in Europe due to its demonstrated efficacy.

The ability of Fabrazyme to be taken up by cells and transported to the lysosome is due to the presence of mannose 6-phosphate (M6P) on its N-linked carbohydrate. Fabrazyme is delivered to lysosomes through binding to the mannose-6-phosphate/IGF-II receptor (M6P/IGF-Iir), present on the cell surface of most cell types, and subsequent receptor mediated endocytosis. Fabrazyme reportedly has three N-linked glycosylation sites at ASN residues 108, 161, and 184. The predominant carbohydrates at these positions are fucosylated biantennary bisialylated complex, monophosphorylated mannose-7 oligomannose, and biphosphorylated mannose-7 oligomannose, respectively.

The glycosylation independent lysosomal targeting (GILT) technology of the present invention directly targets therapeutic proteins to the lysosome via a different interaction with the M6P/IGF-Iir. A targeting ligand is derived from mature human IGF-II, which also binds with high affinity to the M6P/IGF-Iir. In current applications, the IGF-II tag is provided as a c-terminal fusion to the therapeutic protein, although other configurations are feasible including cross-linking. The competency of GILT-modified enzymes for uptake into cells has been established using GILT-modified β-glucuronidase, which is efficiently taken up by fibroblasts in a process that is competed with excess IGF-II. Advantages of the GILT modification are increased binding to the M6P/IGF-II receptor, enhanced uptake into lysosomes of target cells, altered or improved pharmacokinetics, and expanded, altered or improved range of tissue distribution. The improved range of tissue distributions could include delivery of GILT-modified α-GAL A across the blood-brain barrier since IGF proteins demonstrably cross the blood-brain barrier.

Another advantage of the GILT system is the ability to produce uptake-competent proteins in non-mammalian expression systems where M6P modifications do not occur. In certain embodiments, GILT-modified protein will be produced primarily in CHO cells. In certain others, the GILT tag will be placed at the c-terminus of α-GAL A although the invention is not so limited.

Example 14

Underglycosylated Therapeutic Proteins

The efficacy of a targeted therapeutic can be increased by extending the serum half-life of the targeted therapeutic. Hepatic mannose receptors and asialoglycoprotein receptors eliminate glycoproteins from the circulation by recognizing specific carbohydrate structures (Lee et al. (2002) *Science* 295(5561):1898-1901; Ishibashi et al. (1994) *J. Biol. Chem.* 269(45):27803-6). In some embodiments, the present invention permits targeting of a therapeutic to lysosomes and/or across the blood brain barrier in a manner dependent not on a carbohydrate, but on a polypeptide or an analog thereof.

Actual underglycosylation of these proteins is expected to greatly increase their half-life in the circulation, by minimizing their removal from the circulation by the mannose and asialoglycoprotein receptors. Similarly, functional deglycosylation (e.g. by modifying the carbohydrate residues on the therapeutic protein, as by periodate/sodium borohydride treatment) achieves similar effects by interfering with recognition of the carbohydrate by one or more clearance pathways. Nevertheless, because targeting of the protein relies, in most embodiments, on protein-receptor interactions rather than carbohydrate-receptor interactions, modification or elimination of glycosylation should not adversely affect targeting of the protein to the lysosome and/or across the blood brain barrier.

Any lysosomal enzyme using a peptide targeting signal such as IGF-II can be chemically or enzymatically deglycosylated or modified to produce a therapeutic with the desirable properties of specific lysosomal targeting plus long serum half-life. In the case of some lysosomal storage diseases where it might be important to deliver the therapeutic to macrophage or related cell types via mannose receptor, fully glycosylated therapeutics can be used in combination with underglycosylate targeted therapeutics to achieve targeting to the broadest variety of cell types.

Proteins Underglycosylated when Synthesized

In some cases it will be preferable to produce the targeted therapeutic protein initially in a system that does not produce a fully glycosylated protein. For example, a targeted therapeutic protein can be produced in *E. coli*, thereby generating a completely unglycosylated protein. Alternatively, an unglycosylated protein is produced in mammalian cells treated with tunicamycin, an inhibitor of Dol-PP-GlcNAc formation. If, however, a particular targeted therapeutic does not fold correctly in the absence of glycosylation, it is preferably produced initially as a glycosylated protein, and subsequently deglycosylated or rendered functionally underglycosylated.

Underglycosylated targeted therapeutic proteins can also by prepared by engineering a gene encoding the targeted therapeutic protein so that an amino acid that normally serves as an acceptor for glycosylation is changed to a different amino acid. For example, an asparagine residue that serves as an acceptor for N-linked glycosylation can be changed to a glutamine residue, or another residue that is not a glycosylation acceptor. This conservative change is most likely to have a minimal impact on enzyme structure while eliminating glycosylation at the site. Alternatively, other amino acids in the vicinity of the glycosylation acceptor can be modified, disrupting a recognition motif for glycosylation enzymes without necessarily changing the amino acid that would normally be glycosylated.

In the case of GUS, removal of any one of 4 potential glycosylation sites lessens the amount of glycosylation while retaining ample enzyme activity (Shipley et al. (1993) *J. Biol. Chem.* 268(16):12193-8). Removal of some sets of two glycosylation sites from GUS still permits significant enzyme activity. Removal of all four glycosylation sites eliminates enzyme activity, as does treatment of cells with tunicamycin, but deglycosylation of purified enzyme results in enzymatically active material. Therefore, loss of activity associated with removal of the glycosylation sites is likely due to incorrect folding of the enzyme.

Other enzymes, however, fold correctly even in the absence of glycosylation. For example, bacterial β-glucuronidase is naturally unglycosylated, and can be targeted to a mammalian lysosome and/or across the blood brain barrier using the targeting moieties of the present invention. Such enzymes can be synthesized in an unglycosylated state, rather than, for example, synthesizing them as glycosylated proteins and subsequently deglycosylating them.

Deglycosylation

If the targeted therapeutic is produced in a mammalian cell culture system, it is preferably secreted into the growth medium, which can be harvested, permitting subsequent purification of the targeted therapeutic by, for example, chromatographic purification protocols, such as those involving ion exchange, gel filtration, hydrophobic chromatography, ConA chromatography, affinity chromatography or immunoaffinity chromatography.

Chemical deglycosylation of glycoproteins can be achieved in a number of ways, including treatment with trifluoromethane sulfonic acid (TFMS), or treatment with hydrogen fluoride (HF).

Chemical deglycosylation by TFMS (Sojar et al. (1989) *J. Biol. Chem.* 264(5):2552-9; Sojar et al. (1987) *Methods Enzmmol.* 138:341-50): 1 mg GILT-GUS is dried under vacuum overnight. The dried protein is treated with 150 µl TFMS at 0° C. for 0.5-2 hours under nitrogen with occasional shaking. The reaction mix is cooled to below –20° C. in a dry ice-ethanol bath and the reaction is neutralized by the gradual addition of a prechilled (–20° C.) solution of 60% pyridine in water. The neutralized reaction mix is then dialyzed at 4° C. against several changes of $NH_4HCO_3$ at pH 7.0. Chemical deglycosylation with TFMS can result in modifications to the treated protein including methylation, succinimide formation and isomerization of aspartate residues (Douglass et al. (2001) *J. Protein Chem.* 20(7):57'-6).

Chemical deglycosylation by HF (Sojar et al. (1987) *Methods Enzymol.* 138:341-50): The reaction is carried out in a closed reaction system such as can be obtained from Peninsula Laboratories, Inc. 10 mg GILT-GUS is vacuum dried and placed in a reaction vessel which is then connected to the HF apparatus. After the entire HF line is evacuated, 10 mL anhydrous HF is distilled over from the reservoir with stirring of the reaction vessel. The reaction is continued for 1-2 hours at 0° C. Afterwards, a water aspirator removes the HF over 15-30 minutes. Remaining traces of HF are removed under high vacuum. The reaction mixture is dissolved in 2 mL 0.2M NaOH to neutralize any remaining HF and the pH is readjusted to 7.5 with cold 0.2M HCl.

Enzymatic deglycosylation (Thotakura et al. (1987) *Methods Enzymol.* 138:350-9): N-linked carbohydrates can be removed completely from glycoproteins using protein N-glycosidase (PNGase) A or F. In one embodiment, a glycoprotein is denatured prior to treatment with a glycosidase to facilitate action of the enzyme on the glycoprotein; the glycoprotein is subsequently refolded as discussed in the "In vitro refolding" section above. In another embodiment, excess glycosidase is used to treat a native glycoprotein to promote effective deglycosylation.

In the case of a targeted therapeutic protein that is actually underglycosylated, it is possible that the reduced glycosylation will reveal protease-sensitive sites on the targeted therapeutic protein, which will diminish the half-life of the protein. N-linked glycosylation is known to protect a subset of lysosomal enzymes from proteolysis (Kundra et al. (1999) *J. Biol. Chem.* 274(43):31039-46). Such protease-sensitive sites are preferably engineered out of the protein (e.g. by site-directed mutagenesis). As discussed below, the risk of revealing either a protease-sensitive site or a potential epitope can be minimized by incomplete deglycosylation or by modifying the carbohydrate structure rather than omitting the carbohydrate altogether.

Modification of Carbohydrate Structure or Partial Deglycosylation

In some embodiments, the therapeutic protein is partially deglycosylated. For example, the therapeutic protein can be treated with an endoglycosidase such as endoglycosidase H, which cleaves N-linked high mannose carbohydrate but not complex type carbohydrate leaving a single GlcNAc residue linked to the asparagine. A therapeutic protein treated in this way will lack high mannose carbohydrate, reducing interaction with the hepatic mannose receptor. Even though this receptor recognizes terminal GlcNAc, the probability of a productive interaction with the single GlcNAc on the protein surface is not as great as with an intact high mannose structure. If the therapeutic protein is produced in mammalian cells, any complex carbohydrate present on the protein will remains unaffected by the endoH treatment and may be terminally sialylated, thereby diminishing interactions with hepatic carbohydrate recognizing receptors. Such a protein is therefore likely to have increased half-life. At the same time, steric hinderance by the remaining carbohydrate should shield potential epitopes on the protein surface from the immune system and diminish access of proteases to the protein surface (e.g. in the protease-rich lysosomal environment).

In other embodiments, glycosylation of a therapeutic protein is modified, e.g. by oxidation, reduction, dehydration, substitution, esterification, alkylation, sialylation, carbon-carbon bond cleavage, or the like, to reduce clearance of the therapeutic protein from the blood. In some preferred embodiments, the therapeutic protein is not sialylated. For example, treatment with periodate and sodium borohydride is effective to modify the carbohydrate structure of most glycoproteins. Periodate treatment oxidizes vicinal diols, cleaving the carbon-carbon bond and replacing the hydroxyl groups with aldehyde groups; borohydride reduces the aldehydes to hydroxyls. Many sugar residues include vicinal diols and, therefore, are cleaved by this treatment. As shown in FIG. 9A, a protein may be glycosylated on an asparagine residue with a high mannose carbohydrate that includes N-acetylglucosamine residues near the asparagine and mannose residues elsewhere in the structure. As shown in FIG. 9B, the terminal mannose residues have three consecutive carbons with hydroxyl groups; both of the carbon-carbon bonds involved are cleaved by periodate treatment. Some nonterminal mannose residues also include a vicinal diol, which would similarly be cleaved. Nevertheless, while this treatment converts cyclic carbohydrates into linear carbohydrates, it does not completely remove the carbohydrate, minimizing risks of exposing potentially protease-sensitive or antigenic polypeptide sites.

The half-life of lysosomal enzyme β-glucuronidase is known to increase more than tenfold after sequential treatment with periodate and sodium borohydride (Houba et al. (1996) *Bioconjug. Chem.* 7(5):606-11; Stahl et al (1976) *PNAS* 73:4045-4049; Achord et al. (1977) *Pediat. Res.* 11:816-822; Achord et al. (1978) *Cell* 15(1):269-78). Similarly, ricin has been treated with a mixture of periodate and sodium cyanoborohydride (Thorpe et al. (1985) *Eur. J. Biochem.* 147:197). After injection into rats, the fraction of ricin adsorbed by the liver decreased from 40% (untreated ricin) to 20% (modified ricin) of the injected dose with chemical treatment. In contrast the amount of ricin in the blood increased from 20% (untreated ricin) to 45% (treated ricin). Thus, the treated ricin enjoyed a wider tissue distribution and longer half-life in the circulation.

A β-glucuronidase construct (or other glycoprotein) coupled to a targeting moiety of the invention when deglycosylated or modified by sequential treatment with periodate and sodium borohydride should enjoy a similar (e.g. more than twofold, more than fourfold, or more than tenfold) increase in halflife while still retaining a high affinity for the cation-independent M6P receptor, permitting targeting of the construct to the lysosome of all cell types that possess this receptor. The construct is also predicted to cross the blood brain barrier efficiently. In contrast, if a β-glucuronidase preparation that relies on M6P for lysosomal targeting is deglycosylated or treated with periodate and sodium borohydride, it will enjoy an elevated serum half-life but will be unable to target the lysosome since the M6P targeting signal will have been modified by the treatment.

Carbohydrate modification by sequential treatment with periodate and sodium borohydride can be performed as follows: Purified GILT-GUS is incubated with 40 mM $NaIO_4$ in 50 mM sodium acetate pH 4.5 for 2 hours at 4° C. The reaction is stopped by addition of excess ethylene glycol and unreacted reagents are removed by passing the reaction mix over Sephadex G-25M equilibrated with PBS pH 7.5. This treatment is followed by incubation with 40 mM $NaBH_4$ in PBS at pH 7.5 and 37° C. for three hours and then for one hour at 4° C. Passing the reaction mixture over a Sephadex G-25M column eluted with PBS at pH 7.5 terminates the reaction.

Another protocol for periodate and sodium borohydride treatment is described in Hickman et al. (1974) *BBRC* 57:55-61. The purified protein is dialyzed into 0.01 M sodium phosphate pH 6.0, 0.15 M NaCl. Sodium periodate is added to a final concentration of 0.01 M and the reaction proceeds at 4° C. in the dark for at least six hours. Treatment of β-hexosaminidase with periodate under these conditions is sufficient to prevent uptake of the protein by fibroblasts; uptake is normally dependent on M6P moieties on the β-hexosaminidase with the M6P receptor on the fibroblast cell surface. Thus, periodate oxidation modifies M6P sufficiently to abolish its ability to interact with the M6P receptor.

Alternatively, the carbohydrate can be modified by treatment with periodate and cyanoborohydride in a one step reaction as disclosed in Thorpe et al. (1985) *Eur. J. Biochem.* 147:197-206.

The presence of carbohydrate in a partially deglycosylated protein or a protein with a modified glycosylation pattern should shield potential polypeptide epitopes that might be uncovered by complete absence of glycosylation. In the event that a therapeutic protein does provoke an immune response, immunosuppressive therapies can be used in conjunction with the therapeutic protein (Brooks (1999) *Molecular Genetics and Metabolism* 68:268-275). For example, it has been reported that about 15% of Gaucher disease patients treated with alglucerase developed immune responses (Beutler, et al., in *The Metabolic and Molecular Bases of Inherited Disease,* $8^{th}$ ed. (2001), Scriver et al., eds., pp. 3635-3668). Fortunately, many (82/142) of the patients that produced antibody against alglucerase became tolerized by the normal treatment regimen (Rosenberg et al., (1999) *Blood* 93:2081-2088). Thus, to benefit the small minority of patients who may develop an immune response, a patient receiving a therapeutic protein also receives an immunosuppressive therapy in some embodiments of the invention.

Testing

To verify that a protein is underglycosylated, it can be tested by exposure to ConA. An underglycosylated protein is expected to demonstrate reduced binding to ConA-sepharose when compared to the corresponding fully glycosylated protein.

An actually underglycosylated protein can also be resolved by SDS-PAGE and compared to the corresponding fully-glycosylated protein. For example, chemically deglycosylated GUS-GILT can be compared to untreated (glycosylated) GUS-GILT and to enzymatically deglycosylated GUS-GILT prepared with PNGase A. The underglycosylated protein is expected to have a greater mobility in SDS-PAGE when compared to the fully glycosylated protein.

Underglycosylated targeted therapeutic proteins display uptake that is dependent on the targeting domain. Underglycosylated proteins should display reduced uptake (and, preferably, substantially no uptake) that is dependent on mannose or M6P. These properties can be experimentally verified in cell uptake experiments.

For example, a GUS-GILT protein synthesized in mammalian cells and subsequently treated with periodate and borohydride can be tested for functional deglycosylation by testing M6P-dependent and mannose-dependent uptake. To demonstrate that M6P-dependent uptake has been reduced, uptake assays are performed using GM4668 fibroblasts. In the absence of competitor, treated and untreated enzyme will each display significant uptake. The presence of excess IGF-II substantially reduces uptake of treated and untreated enzyme, although untreated enzyme retains residual uptake via a M6P-dependent pathway. Excess M6P reduces the uptake of untreated enzyme, but is substantially less effective at reducing the uptake of functionally deglycosylated protein. For treated and untreated enzymes, the simultaneous presence of both competitors should substantially abolish uptake.

Uptake assays to assess mannose-dependent uptake are performed using J774-E cells, a mouse macrophage-like cell line bearing mannose receptors but few, if any, M6P receptors (Diment et al. (1987) *J. Leukocyte Biol.* 42:485-490). The cells are cultured in DMEM, low glucose, supplemented with 10% FBS, 4 mM glutamine, and antibiotic, antimycotic solution (Sigma, A-5955). Uptake assays with these cells are performed in a manner identical to assays performed with fibroblasts. In the presence of excess M6P and IGF-II, which will eliminate uptake due to any residual M6P/IGF-II receptor, fully glycosylated enzyme will display significant uptake due to interaction with the mannose receptor. Underglycosylated enzyme is expected to display substantially reduced uptake under these conditions. The mannose receptor-dependent uptake of fully glycosylated enzyme can be competed by the addition of excess (100 µg/mL) mannan.

Pharmacokinetics of deglycosylated GUS-GILT can be determined by giving intravenous injections of 20,000 enzyme units to groups of three MPSVII mice per timepoint. For each timepoint 50 µL of blood is assayed for enzyme activity.

INCORPORATION BY REFERENCE

The disclosure of each of the patent documents, scientific publications, and Protein Data Bank records disclosed herein, and U.S. Provisional Application No. 60/250,446, filed Nov. 30, 2000; U.S. Provisional Application 60/287,531, filed Apr. 30, 2001; U.S. Provisional Application 60/290,281, filed May 11, 2001; U.S. Provisional Application 60/304,609, filed Jul. 10, 2001; U.S. Provisional Application No. 60/329,461, filed Oct. 15, 2001; International Patent Application Serial No. PCT/US01/44935, filed Nov. 30, 2001; U.S. Provisional Application No. 60/351,276, filed Jan. 23, 2002; U.S. Ser. Nos. 10/136,841 and 10/136,639, filed Apr. 30, 2002, U.S. Ser. No. 60/384,452, filed May 29, 2002; U.S. Ser. No. 60/386,019, filed Jun. 5, 2002; and U.S. Ser. No. 60/408,816, filed Sep. 6, 2002, are incorporated by reference into this application in their entirety.

---

The invention claimed is:

1. A method of targeting a therapeutic enzyme to a lysosome, the method comprising:
  (a) providing a targeted therapeutic comprising a therapeutic enzyme and a lysosomal-targeting domain that binds the cation-independent mannose-6-phosphate receptor in a mannose-6-phosphate-independent manner; wherein the lysosomal-targeting domain comprises a mature human IGF-II;
  (b) contacting the targeted therapeutic with a cell deficient in a lysosomal enzyme, wherein the cell expresses the cation-independent mannose-6-phosphate receptor on the surface, thereby targeting the therapeutic enzyme to the lysosome as a result of the binding between the lysosomal-targeting domain and the cation-independent mannose-6-phosphate receptor.

2. The method of claim 1, wherein the therapeutic enzyme is a lysosomal enzyme.

3. The method of claim 2, wherein the lysosomal enzyme is human acid-α1,4-glucosidase.

4. A method of targeting a therapeutic enzyme to a lysosome, the method comprising:
  a) providing a targeted therapeutic comprising a therapeutic enzyme and a lysosomal-targeting domain that binds the cation-independent mannose-6-phosphate receptor in a mannose-6-phosphate-independent manner;

wherein the lysosomal-targeting domain comprises a mutein of mature human IGF-II having an amino acid sequence at least 70% identical to mature human IGF-II;

b) contacting the targeted therapeutic with a cell deficient in a lysosomal enzyme, wherein the cell expresses the cation-independent mannose-6-phosphate receptor on the surface, thereby targeting the therapeutic enzyme to the lysosome as a result of the binding between the lysosomal-targeting domain and the cation-independent mannose-6-phosphate receptor.

5. The method of claim 4, wherein the mutein comprises a deletion or a replacement of amino acids 1-7 of mature human IGF-II.

6. The method of claim 5, wherein the mutein comprises a replacement of amino acids 1-7 of mature human IGF-II with one or more amino acid residues.

7. The method of claim 4, wherein the mutein is a fragment of mature human IGF-II.

8. The method of claim 4, wherein the therapeutic enzyme is a lysosomal enzyme.

9. The method of claim 8, wherein the lysosomal enzyme is human acid-α1,4-glucosidase.

10. A method of treating a lysosomal storage disease comprising administering to a subject in need of treatment a targeted therapeutic comprising a lysosomal enzyme and a lysosomal-targeting domain that binds the cation-independent mannose-6-phosphate receptor in a mannose-6-phosphate-independent manner, wherein the lysosomal-targeting domain comprises a mature human IGF-II.

11. The method of claim 10, wherein the lysosomal enzyme is human acid-α1,4-glucosidase.

12. A method of treating a lysosomal storage disease comprising administering to a subject in need of treatment a targeted therapeutic comprising a lysosomal enzyme and a lysosomal-targeting domain that binds the cation-independent mannose-6-phosphate receptor in a mannose-6-phosphate-independent manner, wherein the lysosomal-targeting domain comprises a mutein of mature human IGF-II having an amino acid sequence at least 70% identical to mature human IGF-II.

13. The method of claim 12, wherein the mutein comprises a deletion or a replacement of amino acids 1-7 of mature human IGF-II.

14. The method of claim 13, wherein the mutein comprises a replacement of amino acids 1-7 of mature human IGF-II with one or more amino acid residues.

15. The method of claim 12, wherein the lysosomal enzyme is human acid-α1,4-glucosidase.

* * * * *

SEQUENCE LISTING

<160> NUMBER OF SEQ ID NOS: 22

<210> SEQ ID NO 1
<211> LENGTH: 543
<212> TYPE: DNA
<213> ORGANISM: Homo sapiens
<220> FEATURE:
<221> NAME/KEY: CDS
<222> LOCATION: (1)..(540)
<223> OTHER INFORMATION:

<400> SEQUENCE: 1

```
atg gga atc cca atg ggg aag tcg atg ctg gtg ctt ctc acc ttc ttg      48
Met Gly Ile Pro Met Gly Lys Ser Met Leu Val Leu Leu Thr Phe Leu
1               5                   10                  15 gcc ttc gcc tcg tgc tgc att gct gct tac cgc ccc agt gag acc ctg      96
Ala Phe Ala Ser Cys Cys Ile Ala Ala Tyr Arg Pro Ser Glu Thr Leu
                20                  25                  30 tgc ggc ggg gag ctg gtg gac acc ctc cag ttc gtc tgt ggg gac cgc     144
Cys Gly Gly Glu Leu Val Asp Thr Leu Gln Phe Val Cys Gly Asp Arg
            35                  40                  45 ggc ttc tac ttc agc agg ccc gca agc cgt gtg agc cgt cgc agc cgt     192
Gly Phe Tyr Phe Ser Arg Pro Ala Ser Arg Val Ser Arg Arg Ser Arg
        50                  55                  60 ggc atc gtt gag gag tgc tgt ttc cgc agc tgt gac ctg gcc ctc ctg     240
Gly Ile Val Glu Glu Cys Cys Phe Arg Ser Cys Asp Leu Ala Leu Leu
65                  70                  75                  80
```

-continued

```
gag acg tac tgt gct acc ccc gcc aag tcc gag agg gac gtg tcg acc      288
Glu Thr Tyr Cys Ala Thr Pro Ala Lys Ser Glu Arg Asp Val Ser Thr
                85                  90                  95 cct ccg acc gtg ctt ccg gac aac ttc ccc aga tac ccc gtg ggc aag      336
Pro Pro Thr Val Leu Pro Asp Asn Phe Pro Arg Tyr Pro Val Gly Lys
            100                 105                 110 ttc ttc caa tat gac acc tgg aag cag tcc acc cag cgc ctg cgc agg      384
Phe Phe Gln Tyr Asp Thr Trp Lys Gln Ser Thr Gln Arg Leu Arg Arg
        115                 120                 125 ggc ctg cct gcc ctc ctg cgt gcc cgc cgg ggt cac gtg ctc gcc aag      432
Gly Leu Pro Ala Leu Leu Arg Ala Arg Arg Gly His Val Leu Ala Lys
    130                 135                 140 gag ctc gag gcg ttc agg gag gcc aaa cgt cac cgt ccc ctg att gct      480
Glu Leu Glu Ala Phe Arg Glu Ala Lys Arg His Arg Pro Leu Ile Ala
145                 150                 155                 160 cta ccc acc caa gac ccc gcc cac ggg ggc gcc ccc cca gag atg gcc      528
Leu Pro Thr Gln Asp Pro Ala His Gly Gly Ala Pro Pro Glu Met Ala
                165                 170                 175 agc aat cgg aag tga                                                   543
Ser Asn Arg Lys
        180

<210> SEQ ID NO 2
<211> LENGTH: 180
<212> TYPE: PRT
<213> ORGANISM: Homo sapiens

<400> SEQUENCE: 2

Met Gly Ile Pro Met Gly Lys Ser Met Leu Val Leu Leu Thr Phe Leu
1               5                   10                  15

Ala Phe Ala Ser Cys Cys Ile Ala Ala Tyr Arg Pro Ser Glu Thr Leu
            20                  25                  30

Cys Gly Gly Glu Leu Val Asp Thr Leu Gln Phe Val Cys Gly Asp Arg
        35                  40                  45

Gly Phe Tyr Phe Ser Arg Pro Ala Ser Arg Val Ser Arg Arg Ser Arg
    50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ser Thr
                85                  90                  95

Pro Pro Thr Val Leu Pro Asp Asn Phe Pro Arg Tyr Pro Val Gly Lys
            100                 105                 110

Phe Phe Gln Tyr Asp Thr Trp Lys Gln Ser Thr Gln Arg Leu Arg Arg
        115                 120                 125

Gly Leu Pro Ala Leu Leu Arg Ala Arg Arg Gly His Val Leu Ala Lys
    130                 135                 140

Glu Leu Glu Ala Phe Arg Glu Ala Lys Arg His Arg Pro Leu Ile Ala
145                 150                 155                 160

Leu Pro Thr Gln Asp Pro Ala His Gly Gly Ala Pro Pro Glu Met Ala
                165                 170                 175

Ser Asn Arg Lys
        180

<210> SEQ ID NO 3
<211> LENGTH: 237
<212> TYPE: DNA
<213> ORGANISM: Artificial Sequence
<220> FEATURE:
```

-continued

<223> OTHER INFORMATION: Leishmania codon optimized IGF-II
<220> FEATURE:
<221> NAME/KEY: CDS
<222> LOCATION: (14)..(223)
<223> OTHER INFORMATION:

<400> SEQUENCE: 3
ccgtctagag ctc ggc gcg ccg gcg tac cgc ccg agc gag acg ctg tgc 49
Gly Ala Pro Ala Tyr Arg Pro Ser Glu Thr Leu Cys
1 5 10 ggc ggc gag ctg gtg gac acg ctg cag ttc gtg tgc ggc gac cgc ggc 97
Gly Gly Glu Leu Val Asp Thr Leu Gln Phe Val Cys Gly Asp Arg Gly
15 20 25 ttc tac ttc agc cgc ccg gcc agc cgc gtg agc cgc cgc agc cgc ggc 145
Phe Tyr Phe Ser Arg Pro Ala Ser Arg Val Ser Arg Arg Ser Arg Gly
30 35 40 atc gtg gag gag tgc tgc ttc cgc agc tgc gac ctg gcg ctg ctg gag 193
Ile Val Glu Glu Cys Cys Phe Arg Ser Cys Asp Leu Ala Leu Leu Glu
45 50 55 60 acg tac tgc gcg acg ccg gcg aag tcg gag taagatctag agcg 237
Thr Tyr Cys Ala Thr Pro Ala Lys Ser Glu
65 70

<210> SEQ ID NO 4
<211> LENGTH: 70
<212> TYPE: PRT
<213> ORGANISM: Artificial Sequence
<220> FEATURE:
<223> OTHER INFORMATION: Leishmania codon optimized IGF-II

<400> SEQUENCE: 4

Gly Ala Pro Ala Tyr Arg Pro Ser Glu Thr Leu Cys Gly Gly Glu Leu
1 5 10 15

Val Asp Thr Leu Gln Phe Val Cys Gly Asp Arg Gly Phe Tyr Phe Ser
20 25 30

Arg Pro Ala Ser Arg Val Ser Arg Arg Ser Arg Gly Ile Val Glu Glu
35 40 45

Cys Cys Phe Arg Ser Cys Asp Leu Ala Leu Leu Glu Thr Tyr Cys Ala
50 55 60

Thr Pro Ala Lys Ser Glu
65 70

<210> SEQ ID NO 5
<211> LENGTH: 2169
<212> TYPE: DNA
<213> ORGANISM: Artificial Sequence
<220> FEATURE:
<223> OTHER INFORMATION: A recombinant DNA sequence incorporating a
signal peptide sequence, the mature human beta-glucuronidase
sequence, a bridge of three amino acids, and an IGF-II sequence
<220> FEATURE:
<221> NAME/KEY: CDS
<222> LOCATION: (1)..(2166)
<223> OTHER INFORMATION:

<400> SEQUENCE: 5 atg gcc tct agg ctc gtc cgt gtg ctg gcg gcc gcc atg ctg gtt gca 48
Met Ala Ser Arg Leu Val Arg Val Leu Ala Ala Ala Met Leu Val Ala
1 5 10 15 gcg gcc gtg tcg gtc gac gcg ctg cag ggc ggg atg ctg tac ccc cag 96
Ala Ala Val Ser Val Asp Ala Leu Gln Gly Gly Met Leu Tyr Pro Gln
20 25 30 gag agc ccg tcg cgg gag tgc aag gag ctg gac ggc ctc tgg agc ttc 144
Glu Ser Pro Ser Arg Glu Cys Lys Glu Leu Asp Gly Leu Trp Ser Phe

```
                  35                  40                  45
cgc gcc gac ttc tct gac aac cga cgc cgg ggc ttc gag gag cag tgg       192
Arg Ala Asp Phe Ser Asp Asn Arg Arg Arg Gly Phe Glu Glu Gln Trp
 50                  55                  60 tac cgg cgg ccg ctg tgg gag tca ggc ccc acc gtg gac atg cca gtt       240
Tyr Arg Arg Pro Leu Trp Glu Ser Gly Pro Thr Val Asp Met Pro Val
 65                  70                  75                  80 ccc tcc agc ttc aat gac atc agc cag gac tgg cgt ctg cgg cat ttt       288
Pro Ser Ser Phe Asn Asp Ile Ser Gln Asp Trp Arg Leu Arg His Phe
                 85                  90                  95 gtc ggc tgg gtg tgg tac gaa cgg gag gtg atc ctg ccg gag cga tgg       336
Val Gly Trp Val Trp Tyr Glu Arg Glu Val Ile Leu Pro Glu Arg Trp
            100                 105                 110 acc cag gac ctg cgc aca aga gtg gtg ctg agg att ggc agt gcc cat       384
Thr Gln Asp Leu Arg Thr Arg Val Val Leu Arg Ile Gly Ser Ala His
        115                 120                 125 tcc tat gcc atc gtg tgg gtg aat ggg gtc gac acg cta gag cat gag       432
Ser Tyr Ala Ile Val Trp Val Asn Gly Val Asp Thr Leu Glu His Glu
    130                 135                 140 ggg ggc tac ctc ccc ttc gag gcc gac atc agc aac ctg gtc cag gtg       480
Gly Gly Tyr Leu Pro Phe Glu Ala Asp Ile Ser Asn Leu Val Gln Val
145                 150                 155                 160 ggg ccc ctg ccc tcc cgg ctc cga atc act atc gcc atc aac aac aca       528
Gly Pro Leu Pro Ser Arg Leu Arg Ile Thr Ile Ala Ile Asn Asn Thr
                165                 170                 175 ctc acc ccc acc acc ctg cca cca ggg acc atc caa tac ctg act gac       576
Leu Thr Pro Thr Thr Leu Pro Pro Gly Thr Ile Gln Tyr Leu Thr Asp
            180                 185                 190 acc tcc aag tat ccc aag ggt tac ttt gtc cag aac aca tat ttt gac       624
Thr Ser Lys Tyr Pro Lys Gly Tyr Phe Val Gln Asn Thr Tyr Phe Asp
        195                 200                 205 ttt ttc aac tac gct gga ctg cag cgg tct gta ctt ctg tac acg aca       672
Phe Phe Asn Tyr Ala Gly Leu Gln Arg Ser Val Leu Leu Tyr Thr Thr
    210                 215                 220 ccc acc acc tac atc gat gac atc acc gtc acc acc agc gtg gag caa       720
Pro Thr Thr Tyr Ile Asp Asp Ile Thr Val Thr Thr Ser Val Glu Gln
225                 230                 235                 240 gac agt ggg ctg gtg aat tac cag atc tct gtc aag ggc agt aac ctg       768
Asp Ser Gly Leu Val Asn Tyr Gln Ile Ser Val Lys Gly Ser Asn Leu
                245                 250                 255 ttc aag ttg gaa gtg cgt ctt ttg gat gca gaa aac aaa gtc gtg gcg       816
Phe Lys Leu Glu Val Arg Leu Leu Asp Ala Glu Asn Lys Val Val Ala
            260                 265                 270 aat ggg act ggg acc cag ggc caa ctt aag gtg cca ggt gtc agc ctc       864
Asn Gly Thr Gly Thr Gln Gly Gln Leu Lys Val Pro Gly Val Ser Leu
        275                 280                 285 tgg tgg ccg tac ctg atg cac gaa cgc cct gcc tat ctg tat tca ttg       912
Trp Trp Pro Tyr Leu Met His Glu Arg Pro Ala Tyr Leu Tyr Ser Leu
    290                 295                 300 gag gtg cag ctg act gca cag acg tca ctg ggg cct gtg tct gac ttc       960
Glu Val Gln Leu Thr Ala Gln Thr Ser Leu Gly Pro Val Ser Asp Phe
305                 310                 315                 320 tac aca ctc cct gtg ggg atc cgc act gtg gct gtc acc aag agc cag      1008
Tyr Thr Leu Pro Val Gly Ile Arg Thr Val Ala Val Thr Lys Ser Gln
                325                 330                 335 ttc ctc atc aat ggg aaa cct ttc tat ttc cac ggt gtc aac aag cat      1056
Phe Leu Ile Asn Gly Lys Pro Phe Tyr Phe His Gly Val Asn Lys His
            340                 345                 350 gag gat gcg gac atc cga ggg aag ggc ttc gac tgg ccg ctg ctg gtg      1104
```

```
                Glu Asp Ala Asp Ile Arg Gly Lys Gly Phe Asp Trp Pro Leu Leu Val
                            355                 360                 365 aag gac ttc aac ctg ctt cgc tgg ctt ggt gcc aac gct ttc cgt acc      1152
Lys Asp Phe Asn Leu Leu Arg Trp Leu Gly Ala Asn Ala Phe Arg Thr
        370                 375                 380 agc cac tac ccc tat gca gag gaa gtg atg cag atg tgt gac cgc tat      1200
Ser His Tyr Pro Tyr Ala Glu Glu Val Met Gln Met Cys Asp Arg Tyr
385                 390                 395                 400 ggg att gtg gtc atc gat gag tgt ccc ggc gtg ggt ctg gcg ctg ccg      1248
Gly Ile Val Val Ile Asp Glu Cys Pro Gly Val Gly Leu Ala Leu Pro
                405                 410                 415 cag ttc ttc aac aac gtt tct ctg cat cac cac atg cag gtg atg gaa      1296
Gln Phe Phe Asn Asn Val Ser Leu His His His Met Gln Val Met Glu
            420                 425                 430 gaa gtg gtg cgt agg gac aag aac cac ccc gcg gtc gtg atg tgg tct      1344
Glu Val Val Arg Arg Asp Lys Asn His Pro Ala Val Val Met Trp Ser
        435                 440                 445 gtg gcc aac gag cct gcg tcc cac cta gaa tct gct ggc tac tac ttg      1392
Val Ala Asn Glu Pro Ala Ser His Leu Glu Ser Ala Gly Tyr Tyr Leu
    450                 455                 460 aag atg gtg atc gct cac acc aaa tcc ttg gac ccc tcc cgg cct gtg      1440
Lys Met Val Ile Ala His Thr Lys Ser Leu Asp Pro Ser Arg Pro Val
465                 470                 475                 480 acc ttt gtg agc aac tct aac tat gca gca gac aag ggg gct ccg tat      1488
Thr Phe Val Ser Asn Ser Asn Tyr Ala Ala Asp Lys Gly Ala Pro Tyr
                485                 490                 495 gtg gat gtg atc tgt ttg aac agc tac tac tct tgg tat cac gac tac      1536
Val Asp Val Ile Cys Leu Asn Ser Tyr Tyr Ser Trp Tyr His Asp Tyr
            500                 505                 510 ggg cac ctg gag ttg att cag ctg cag ctg gcc acc cag ttt gag aac      1584
Gly His Leu Glu Leu Ile Gln Leu Gln Leu Ala Thr Gln Phe Glu Asn
        515                 520                 525 tgg tat aag aag tat cag aag ccc att att cag agc gag tat gga gca      1632
Trp Tyr Lys Lys Tyr Gln Lys Pro Ile Ile Gln Ser Glu Tyr Gly Ala
    530                 535                 540 gaa acg att gca ggg ttt cac cag gat cca cct ctg atg ttc act gaa      1680
Glu Thr Ile Ala Gly Phe His Gln Asp Pro Pro Leu Met Phe Thr Glu
545                 550                 555                 560 gag tac cag aaa agt ctg cta gag cag tac cat ctg ggt ctg gat caa      1728
Glu Tyr Gln Lys Ser Leu Leu Glu Gln Tyr His Leu Gly Leu Asp Gln
                565                 570                 575 aaa cgc aga aaa tat gtg gtt gga gag ctc att tgg aat ttt gcc gat      1776
Lys Arg Arg Lys Tyr Val Val Gly Glu Leu Ile Trp Asn Phe Ala Asp
            580                 585                 590 ttc atg act gaa cag tca ccg acg aga gtg ctg ggg aat aaa aag ggg      1824
Phe Met Thr Glu Gln Ser Pro Thr Arg Val Leu Gly Asn Lys Lys Gly
        595                 600                 605 atc ttc act cgg cag aga caa cca aaa agt gca gcg ttc ctt ttg cga      1872
Ile Phe Thr Arg Gln Arg Gln Pro Lys Ser Ala Ala Phe Leu Leu Arg
    610                 615                 620 gag aga tac tgg aag att gcc aat gaa acc agg tat ccc cac tca gta      1920
Glu Arg Tyr Trp Lys Ile Ala Asn Glu Thr Arg Tyr Pro His Ser Val
625                 630                 635                 640 gcc aag tca caa tgt ttg gaa aac agc ccg ttt act ggc gcg ccg gcg      1968
Ala Lys Ser Gln Cys Leu Glu Asn Ser Pro Phe Thr Gly Ala Pro Ala
                645                 650                 655 tac cgc ccg agc gag acg ctg tgc ggc ggc gag ctg gtg gac acg ctg      2016
Tyr Arg Pro Ser Glu Thr Leu Cys Gly Gly Glu Leu Val Asp Thr Leu
            660                 665                 670
```

-continued

```
cag ttc gtg tgc ggc gac cgc ggc ttc tac ttc agc cgc ccg gcc agc    2064
Gln Phe Val Cys Gly Asp Arg Gly Phe Tyr Phe Ser Arg Pro Ala Ser
        675                 680                 685 cgc gtg agc cgc cgc agc cgc ggc atc gtg gag gag tgc tgc ttc cgc    2112
Arg Val Ser Arg Arg Ser Arg Gly Ile Val Glu Glu Cys Cys Phe Arg
690                 695                 700 agc tgc gac ctg gcg ctg ctg gag acg tac tgc gcg acg ccg gcg aag    2160
Ser Cys Asp Leu Ala Leu Leu Glu Thr Tyr Cys Ala Thr Pro Ala Lys
705                 710                 715                 720 tcg gag taa                                                        2169
Ser Glu
```

<210> SEQ ID NO 6
<211> LENGTH: 722
<212> TYPE: PRT
<213> ORGANISM: Artificial Sequence
<220> FEATURE:
<223> OTHER INFORMATION: A recombinant DNA sequence incorporating a
      signal peptide sequence, the mature human beta-glucuronidase
      sequence, a bridge of three amino acids, and an IGF-II sequence

<400> SEQUENCE: 6

```
Met Ala Ser Arg Leu Val Arg Val Leu Ala Ala Ala Met Leu Val Ala
1               5                   10                  15

Ala Ala Val Ser Val Asp Ala Leu Gln Gly Gly Met Leu Tyr Pro Gln
            20                  25                  30

Glu Ser Pro Ser Arg Glu Cys Lys Glu Leu Asp Gly Leu Trp Ser Phe
        35                  40                  45

Arg Ala Asp Phe Ser Asp Asn Arg Arg Gly Phe Glu Glu Gln Trp
    50                  55                  60

Tyr Arg Arg Pro Leu Trp Glu Ser Gly Pro Thr Val Asp Met Pro Val
65                  70                  75                  80

Pro Ser Ser Phe Asn Asp Ile Ser Gln Asp Trp Arg Leu Arg His Phe
                85                  90                  95

Val Gly Trp Val Trp Tyr Glu Arg Glu Val Ile Leu Pro Glu Arg Trp
            100                 105                 110

Thr Gln Asp Leu Arg Thr Arg Val Val Leu Arg Ile Gly Ser Ala His
        115                 120                 125

Ser Tyr Ala Ile Val Trp Val Asn Gly Val Asp Thr Leu Glu His Glu
    130                 135                 140

Gly Gly Tyr Leu Pro Phe Glu Ala Asp Ile Ser Asn Leu Val Gln Val
145                 150                 155                 160

Gly Pro Leu Pro Ser Arg Leu Arg Ile Thr Ile Ala Ile Asn Asn Thr
                165                 170                 175

Leu Thr Pro Thr Thr Leu Pro Pro Gly Thr Ile Gln Tyr Leu Thr Asp
            180                 185                 190

Thr Ser Lys Tyr Pro Lys Gly Tyr Phe Val Gln Asn Thr Tyr Phe Asp
        195                 200                 205

Phe Phe Asn Tyr Ala Gly Leu Gln Arg Ser Val Leu Leu Tyr Thr Thr
    210                 215                 220

Pro Thr Thr Tyr Ile Asp Asp Ile Thr Val Thr Thr Ser Val Glu Gln
225                 230                 235                 240

Asp Ser Gly Leu Val Asn Tyr Gln Ile Ser Val Lys Gly Ser Asn Leu
                245                 250                 255

Phe Lys Leu Glu Val Arg Leu Leu Asp Ala Glu Asn Lys Val Val Ala
            260                 265                 270

Asn Gly Thr Gly Thr Gln Gly Gln Leu Lys Val Pro Gly Val Ser Leu
```

-continued

```
                275                 280                 285
Trp Trp Pro Tyr Leu Met His Glu Arg Pro Ala Tyr Leu Tyr Ser Leu
    290                 295                 300
Glu Val Gln Leu Thr Ala Gln Thr Ser Leu Gly Pro Val Ser Asp Phe
305                 310                 315                 320
Tyr Thr Leu Pro Val Gly Ile Arg Thr Val Ala Val Thr Lys Ser Gln
                325                 330                 335
Phe Leu Ile Asn Gly Lys Pro Phe Tyr Phe His Gly Val Asn Lys His
                340                 345                 350
Glu Asp Ala Asp Ile Arg Gly Lys Gly Phe Asp Trp Pro Leu Leu Val
                355                 360                 365
Lys Asp Phe Asn Leu Leu Arg Trp Leu Gly Ala Asn Ala Phe Arg Thr
            370                 375                 380
Ser His Tyr Pro Tyr Ala Glu Glu Val Met Gln Met Cys Asp Arg Tyr
385                 390                 395                 400
Gly Ile Val Val Ile Asp Glu Cys Pro Gly Val Gly Leu Ala Leu Pro
                405                 410                 415
Gln Phe Phe Asn Asn Val Ser Leu His His His Met Gln Val Met Glu
                420                 425                 430
Glu Val Val Arg Arg Asp Lys Asn His Pro Ala Val Val Met Trp Ser
            435                 440                 445
Val Ala Asn Glu Pro Ala Ser His Leu Glu Ser Ala Gly Tyr Tyr Leu
    450                 455                 460
Lys Met Val Ile Ala His Thr Lys Ser Leu Asp Pro Ser Arg Pro Val
465                 470                 475                 480
Thr Phe Val Ser Asn Ser Asn Tyr Ala Ala Asp Lys Gly Ala Pro Tyr
                485                 490                 495
Val Asp Val Ile Cys Leu Asn Ser Tyr Tyr Ser Trp Tyr His Asp Tyr
                500                 505                 510
Gly His Leu Glu Leu Ile Gln Leu Gln Leu Ala Thr Gln Phe Glu Asn
            515                 520                 525
Trp Tyr Lys Lys Tyr Gln Lys Pro Ile Ile Gln Ser Glu Tyr Gly Ala
    530                 535                 540
Glu Thr Ile Ala Gly Phe His Gln Asp Pro Pro Leu Met Phe Thr Glu
545                 550                 555                 560
Glu Tyr Gln Lys Ser Leu Leu Glu Gln Tyr His Leu Gly Leu Asp Gln
                565                 570                 575
Lys Arg Arg Lys Tyr Val Val Gly Glu Leu Ile Trp Asn Phe Ala Asp
                580                 585                 590
Phe Met Thr Glu Gln Ser Pro Thr Arg Val Leu Gly Asn Lys Lys Gly
                595                 600                 605
Ile Phe Thr Arg Gln Arg Gln Pro Lys Ser Ala Ala Phe Leu Leu Arg
            610                 615                 620
Glu Arg Tyr Trp Lys Ile Ala Asn Glu Thr Arg Tyr Pro His Ser Val
625                 630                 635                 640
Ala Lys Ser Gln Cys Leu Glu Asn Ser Pro Phe Thr Gly Ala Pro Ala
                645                 650                 655
Tyr Arg Pro Ser Glu Thr Leu Cys Gly Gly Glu Leu Val Asp Thr Leu
                660                 665                 670
Gln Phe Val Cys Gly Asp Arg Gly Phe Tyr Phe Ser Arg Pro Ala Ser
            675                 680                 685
Arg Val Ser Arg Arg Ser Arg Gly Ile Val Glu Glu Cys Cys Phe Arg
    690                 695                 700
```

-continued

Ser Cys Asp Leu Ala Leu Leu Glu Thr Tyr Cys Ala Thr Pro Ala Lys
705                 710                 715                 720

Ser Glu

<210> SEQ ID NO 7
<211> LENGTH: 70
<212> TYPE: PRT
<213> ORGANISM: Homo sapiens

<400> SEQUENCE: 7

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 8
<211> LENGTH: 67
<212> TYPE: PRT
<213> ORGANISM: Homo sapiens

<400> SEQUENCE: 8

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 9
<211> LENGTH: 50
<212> TYPE: DNA
<213> ORGANISM: Artificial Sequence
<220> FEATURE:
<223> OTHER INFORMATION: Oligonucleotide GILT 1

<400> SEQUENCE: 9
gcggcggcga gctggtggac acgctgcagt tcgtgtgcgg cgaccgcggc          50

<210> SEQ ID NO 10
<211> LENGTH: 50
<212> TYPE: DNA
<213> ORGANISM: Artificial Sequence
<220> FEATURE:
<223> OTHER INFORMATION: Oligonucleotide GILT 2

<400> SEQUENCE: 10
ttctacttca gccgcccggc cagccgcgtg agccgccgca gccgcggcat          50

<210> SEQ ID NO 11
<211> LENGTH: 50

<212> TYPE: DNA
<213> ORGANISM: Artificial Sequence
<220> FEATURE:
<223> OTHER INFORMATION: Oligonucleotide GILT 3

<400> SEQUENCE: 11
cgtggaggag tgctgcttcc gcagctgcga cctggcgctg ctggagacgt          50

<210> SEQ ID NO 12
<211> LENGTH: 40
<212> TYPE: DNA
<213> ORGANISM: Artificial Sequence
<220> FEATURE:
<223> OTHER INFORMATION: Oligonucleotide GILT 4

<400> SEQUENCE: 12
actgcgcgac gccggcgaag tcggagtaag atctagagcg                    40

<210> SEQ ID NO 13
<211> LENGTH: 50
<212> TYPE: DNA
<213> ORGANISM: Artificial Sequence
<220> FEATURE:
<223> OTHER INFORMATION: Oligonucleotide GILT 5

<400> SEQUENCE: 13
agcgtgtcca ccagctcgcc gccgcacagc gtctcgctcg ggcggtacgc          50

<210> SEQ ID NO 14
<211> LENGTH: 50
<212> TYPE: DNA
<213> ORGANISM: Artificial Sequence
<220> FEATURE:
<223> OTHER INFORMATION: Oligonucleotide GILT 6

<400> SEQUENCE: 14
ggctggccgg gcggctgaag tagaagccgc ggtcgccgca cacgaactgc          50

<210> SEQ ID NO 15
<211> LENGTH: 50
<212> TYPE: DNA
<213> ORGANISM: Artificial Sequence
<220> FEATURE:
<223> OTHER INFORMATION: Oligonucleotide GILT 7

<400> SEQUENCE: 15
gctgcggaag cagcactcct ccacgatgcc gcggctgcgg cggctcacgc          50

<210> SEQ ID NO 16
<211> LENGTH: 51
<212> TYPE: DNA
<213> ORGANISM: Artificial Sequence
<220> FEATURE:
<223> OTHER INFORMATION: Oligonucleotide GILT 8

<400> SEQUENCE: 16
ctccgacttc gccggcgtcg cgcagtacgt ctccagcagc gccaggtcgc a        51

<210> SEQ ID NO 17
<211> LENGTH: 47
<212> TYPE: DNA
<213> ORGANISM: Artificial Sequence
<220> FEATURE:
<223> OTHER INFORMATION: Oligonucleotide GILT 9

<400> SEQUENCE: 17

-continued

```
ccgtctagag ctcggcgcgc cggcgtaccg cccgagcgag acgctgt           47

<210> SEQ ID NO 18
<211> LENGTH: 25
<212> TYPE: DNA
<213> ORGANISM: Artificial Sequence
<220> FEATURE:
<223> OTHER INFORMATION: Oligonucleotide GILT 10

<400> SEQUENCE: 18
cgctctagat cttactccga cttcg                                   25

<210> SEQ ID NO 19
<211> LENGTH: 46
<212> TYPE: DNA
<213> ORGANISM: Artificial Sequence
<220> FEATURE:
<223> OTHER INFORMATION: Oligonucleotide GILT 11

<400> SEQUENCE: 19
ccgtctagag ctcggcgcgc cgctgtgcgg cggcgagctg gtggac            46

<210> SEQ ID NO 20
<211> LENGTH: 50
<212> TYPE: DNA
<213> ORGANISM: Artificial Sequence
<220> FEATURE:
<223> OTHER INFORMATION: Oligonucleotide GILT 12

<400> SEQUENCE: 20
ttcctgttca gccgcccggc cagccgcgtg agccgccgca gccgcggcat        50

<210> SEQ ID NO 21
<211> LENGTH: 50
<212> TYPE: DNA
<213> ORGANISM: Artificial Sequence
<220> FEATURE:
<223> OTHER INFORMATION: Oligonucleotide GILT 16

<400> SEQUENCE: 21
ggctggccgg gcggctgaac aggaagccgc ggtcgccgca cacgaactgc        50

<210> SEQ ID NO 22
<211> LENGTH: 25
<212> TYPE: DNA
<213> ORGANISM: Artificial Sequence
<220> FEATURE:
<223> OTHER INFORMATION: Oligonucleotide GILT 20

<400> SEQUENCE: 22
ccgtctagag ctcggcgcgc cggcg                                   25
```